US011155603B2

(12) United States Patent
Popel et al.

(10) Patent No.: US 11,155,603 B2
(45) Date of Patent: *Oct. 26, 2021

(54) MIMETIC PEPTIDES DERIVED FROM COLLAGEN TYPE IV AND THEIR USE FOR TREATING ANGIOGENESIS- AND LYMPHANGIOGENESIS- DEPENDENT DISEASES

(71) Applicant: THE JOHNS HOPKINS UNIVERSITY, Baltimore, MD (US)

(72) Inventors: Aleksander S. Popel, Lutherville, MD (US); Elena V. Rosca, Baltimore, MD (US); Jacob E. Koskimaki, Baltimore, MD (US); Corban G. Rivera, Baltimore, MD (US); Niranjan B. Pandey, White Marsh, MD (US); Amir P. Tamiz, Silver Spring, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/989,411

(22) Filed: Aug. 10, 2020

(65) Prior Publication Data
US 2020/0362017 A1 Nov. 19, 2020

Related U.S. Application Data

(60) Continuation of application No. 16/131,754, filed on Sep. 14, 2018, now Pat. No. 10,774,131, which is a continuation of application No. 15/395,648, filed on Dec. 30, 2016, now Pat. No. 10,106,597, which is a continuation of application No. 14/708,829, filed on May 11, 2015, now abandoned, which is a division of application No. 13/992,998, filed as application No. PCT/US2011/064475 on Dec. 12, 2011, now Pat. No. 9,056,923.

(60) Provisional application No. 61/546,314, filed on Oct. 12, 2011, provisional application No. 61/421,706, filed on Dec. 10, 2010.

(51) Int. Cl.
C07K 14/78 (2006.01)
A61K 38/00 (2006.01)
A61P 35/00 (2006.01)
C07K 7/00 (2006.01)

(52) U.S. Cl.
CPC .............. C07K 14/78 (2013.01); A61K 38/00 (2013.01); A61P 35/00 (2018.01); C07K 7/00 (2013.01)

(58) Field of Classification Search
CPC ......... A61K 38/00; A61P 35/00; C07K 14/78; C07K 7/00
See application file for complete search history.

(56) References Cited

U.S. PATENT DOCUMENTS

| | | |
|---|---|---|
| 5,001,116 A | 3/1991 | Folkman |
| 5,192,744 A | 3/1993 | Bouck |
| 5,504,074 A | 4/1996 | D'Amato |
| 5,593,990 A | 1/1997 | D'Amato |
| 5,629,327 A | 5/1997 | D'Amato |
| 5,646,136 A | 7/1997 | Petrow |
| 5,712,291 A | 1/1998 | D'Amato |
| 5,721,226 A | 2/1998 | Frye |
| 5,762,918 A | 6/1998 | Thorpe |
| 5,795,885 A | 8/1998 | Zasloff |
| 5,981,471 A | 11/1999 | Papathanassiu |
| 6,071,948 A | 6/2000 | D'Amato |
| 6,090,794 A | 7/2000 | Martuza |
| 6,150,407 A | 11/2000 | Tuse |
| 2002/0086007 A1 | 7/2002 | Sim et al. |
| 2007/0259817 A1 | 11/2007 | Brooks et al. |
| 2008/0287342 A1 | 11/2008 | Yu et al. |
| 2010/0331263 A1 | 12/2010 | Volpert et al. |

FOREIGN PATENT DOCUMENTS

| | | |
|---|---|---|
| CA | 2396235 | 1/2001 |
| WO | WO2004067762 | 8/2004 |
| WO | WO2007033215 | 3/2007 |
| WO | WO2008085828 | 7/2008 |

OTHER PUBLICATIONS

Abraham et al (2007) Synthesis of the next-generation therapeutic antibodies that combine cell targeting and antibody-catalyzed prodrug activation. Proc Natl Acad Sci;104(13):5584-9.
Arnaoutova et al (2009) The endothelial cell tube formation assay on basement membrane turns 20: state of the science and the art. Angiogenesis;12(3):267-74.
Avraamides et al. (2008) Integrins in angiogenesis and lymphangiogenesis. Nat Rev Cancer. Aug. 2008, 8(8):604-17.
Berendsen (1998), A Glimpae of the Holy Grail?, Science, 282, pp. 642-643.
Bhujwalla et al. (2001) Vascular differences detected by MRI for metastatic versus nonmetastatic breast and prostate cancer xenografts. Neoplasia. 3(2):143-53.

(Continued)

Primary Examiner — James H Alstrum-Acevedo
Assistant Examiner — Erinne R Dabkowski
(74) Attorney, Agent, or Firm — Morgan, Lewis & Bockius LLP

(57) ABSTRACT

Mimetic peptides having anti-angiogenic and anti-tumorigenic properties and methods of their use for treating cancer, ocular diseases, such as age-related macular degeneration, and other-angiogenesis-dependent diseases are disclosed. More particularly, active non-cysteine analogs (mimetics), which exhibit anti-angiogenic activity in endothelial cell proliferation, migration, adhesion, and tube formation assays, anti-migratory activity in human breast cancer cells in vitro, anti-angiogenic and anti-tumori-genic activity in vivo in breast cancer xenograft models, and age-related macular degeneration models are disclosed. The presently disclosed mimetic peptides also exhibit anti-lymphangiogenic and directly anti-tumorigenic properties.

11 Claims, 25 Drawing Sheets
Specification includes a Sequence Listing.

(56) References Cited

OTHER PUBLICATIONS

Bhutia et al. (2008) Targeting tumors with peptides from natural sources. Trends Biotechnol. 26(4):210-7.
Bradley et al. (2011) Cilengitide (EMD 121974, NSC 707544) in asymptomatic metastatic castration resistant prostate cancer patients: a randomized phase II trial by the prostate cancer clinical trials consortium. Invest New Drugs., 29(6):1432-40.
Bradley et al., Limits of Cooperativity in a Structurally Modular Protein: Response of the Notch Ankyrin Domain to Analogous Alanine Substitutions in Each Repeat, J. Mol. Biol (2002) 324, 373-386.
Carmeliet et al (2000) Angiogenesis in cancer and other diseases. Nature. 407(6801):249-57.
Carmeliet et al (2005) Angiogenesis in life, disease and medicine. Nature. 438(7070):932-6.
Carmeliet et al (2011) Molecular mechanisms and clinical applications of angiogenesis. Nature. 473(7347):298-307.
Christiansen, (2011) Lymphangiogenesis and Cancer, Genes & Cancer vol. 2 No. 12.
Cunnick, (2008) Lymphangiogenesis and lymph node metastasis in breast cancer, Molecular Cancer, 7:23.
Eikesdal et al (2008) Identification of amino acids essential for the antiangiogenic activity of tumstatin and its use in combination antitumor activity. Proc Natl Acad Sci., 105(39):15040-5.
Elkin et al (2001) Tail vein assay of cancer metastasis. Curr Protoc Cell Biol.; Chapter 19: Unit 19.2.
Folkman et al (1971) Tumor angiogenesis: therapeutic implications; Tumor angiogenesis: therapeutic Implications.
Folkman et al (2002) Role of angiogenesis in tumor growth and metastasis. Semin Oncol, (6 Suppl 16):15-8.
Folkman et al (2006) Angiogenesis. Annu Rev Med. 57:1-18.
Gautier et al (2010) Biochemical and structural analysis of the binding determinants of a vascular endothelial growth factor receptor peptidic antagonist. J Med Chem.; 53(11):4428-40.
Gentilucci et al (2010) Chemical modifications designed to improve peptide stability: incorporation of non-natural amino adds, pseudo-peptide bonds, and cyclization. Curr Pharm Des.;16(28).3185-203.
Haviv et al (2005) Thrombospondin-1 mimetic peptide inhibitors of angiogenesis and tumor growth: design, synthesis, and optimization of pharmacokinetics and biological activities. J Med Chem, 48(8):2838-46.
Holopainen et al. (2011) Perspectives on lymphangiogenesis and angiogenesis in cancer. J Surg Oncol., 103(6):484-8.
Hruby et al. (1993) Design, synthesis, and conformation of superpotent and prolonged acting melanotropins. Ann N Y Acad Sci., 680:51-63.
Ingber et al. (1988) Inhibition of angiogenesis through modulation of collagen metabolism. Lab Invest., 59(1):44-51.
International Search Report for PCT/US2011/0644 75 dated Jul. 19, 2012.
Kalluri et al (2002) Discovery of type IV collagen non-collagenous domains as novel integrin ligands and endogenous inhibitors of angiogenesis. Cold Spring Harb Symp Quant Biol.;67;255-66.
Kamphaus et al (2000) Canstatin, a novel matrix-derived inhibitor of angiogenesis and tumor growth. J Biol Chem.; 275(2):1209-15.
Karagiannis et al (2007) Identification of novel short peptides derived from the alpha 4, alpha 5, and alpha 6 fibrils of type IV collagen with anti-angiogenic properties. Biochem Biophys Res Commun. 354(2):434-9.
Karagiannis et al (2008) A systematic methodology for proteome-wide identification of peptides inhibiting the proliferation and migration of endothelial cells, PNAS; 105(37): 13775-80.
Kenny et al (2008) Phase I trial of the positron-emitting Arg-Gly-Asp (RGD) peptide radioligand 18F-AH111585 in breast cancer patients. J Nucl Med., 49(6):879-86.
Koskimaki et al (2009) Peptides derived from type IV collagen, CXC chemokines, and thrombospondin-1 domain-containing proteins inhibit neovascularization and suppress tumor growth in MlJA-MB-231 breast cancer xenografts, Neoplasia., 11(12):1285-91.
Koskimaki et al. (2010) Pentastatin-1, a collagen IV derived 2-mer peptide, suppresses tumor growth in a small cell lung cancer xenograft model. BMC Cancer., 10:29.
Lee et al (2011) Small peptides derived from somatotropin domain-containing proteins inhibit blood and lymphatic endothelial cell proliferation, migration, adhesion and tube formation. Int J Biochem Cell Biol;43 (12):1812-21.
Leung et al (1989) Vascular endothelial growth factor is a secreted angiogenic rnitogen. Science.; 246 (4935):1306-9.
Li et al. (2008) Structure-activity relationship studies of permeability modulating peptide AT-1002. Bioorg Med Chem Lett. 18(16):4584-6.
Ma et al (2003) Unnatural amino acids in drug discovery. CHIMICA OGGI 21(6):65-68.
Marneros et al (2001) The role of collagen-derived proteolytic fragments in angiogenesis. Matrix Biol. 20(5-6):337-45.
Mechanisms of Carcinogenesis, 2010, International Agency for Research on Cancer, Section 3, p. 190, col. 1, first paragraph.
Mirochnik et al. (2008) Short pigment epithelial-derived factor-derived peptide inhibits angiogenesis and tumor growth. Clin cancer Res. 15(5):1655-63.
Mumprecht (2009) Lymphangiogenesis and cancer metastasis, J. Cell. Mol. Med. vol. 13, No. 8A, pp. 1405-1416.
Nabors et al (2010) A phase 1 trial of ABT-510 concurrent with standard chemoradiation for patients with newly diagnosed glioblastoma. Arch Neural, 67(3):313-9.
Naveen S. Vasudev, Anti-angiogenic therapy for cancer: current progress, unresolved questions and future directions, Angiogenesis (2014) 17:471-494.
NCBI, GenBank Accession No. CAA57698.1, Apr. 18, 2005.
Ngo et al. (1994) "Computational complexity, protein structure prediction, and the Levinthal paradox", The Protein Folding Problem and Tertiary Structure Prediction; pp. 491-495.
Ogan et al. (1988) Albumin labeled with Gd-DTPA: an intravascular contrast-enhancing agent for magnetic resonance blood pool imaging: preparation and characterization. Invest Radiol. 23(12):961.
Okamoto et al (1997) Transgenic mice with increased expression of vascular endothelial growth factor in the retina: a new model of intraretinal and subretinal neovascuiarization. Am J Pathol. 151(1 ):281-91.
Pernot et al (2011) Stability of peptides and therapeutic success in cancer. Expert Opin Drug Metab Toxicol. 7(7):793-802.
Raman et al (2006) Characterizing vascular parameters in hypoxic regions; a combined magnetic resonance and optical imaging study of a human prostate cancer model. Cancer Res. 66(20);9929-36.
Reardon et al. (2008) Randomized phase II study of cilengitide, an integrin-targeting arginine-glycine-aspartic acid peptide, in recurrent glioblastoma multiforme. J Clin Oncol. 26(34):5610-7.
Rivera et al (2011) Novel peptide-specific quantitative structure-activity relationship (QSAR) analysis applied to collagen IV peptides with antiangiogenic activity. J Med Chem. 13:54(19);6492-500.
Rosca et al., (2011) "Anti-angiogenic peptides for cancer therapeutics", Curr Pharm Biotechnol., vol. 12, No. 8, pp. 1101-1116.
Rosca et al., (2011) "Development of a biomimetic peptide derived from collagen IV with anti-angiogenic activity in breast cancer", Cancer Biology & Therapy, vol. 12, Issue 9, pp. 808-817.
Rudinger (1976) Peptide Hormones, JA Parsons, Ed., pp. 1-7.
Saladin et al (2009) Current trends in the clinical development of peptide therapeutics. IDrugs. 12 (12):779-84.
Senger et al (1983) Tumor cells secrete a vascular permeability factor that promotes accumulation of ascites fluid. Science; 219(4587):983-5.
Sigma, 2004, pp. 1-2.
Sundramoorthy et al (2002) Crystal structure of NC1 domains. Structural basis for type IV collagen assembly in basement membranes. J Biol Chem. 23;277(34):31142-53.
Supplementary European Search Report dated Apr. 9, 2014 for EP Application No. 11847661.3.
Than et al (2002) The 1.9-A crystal structure of the noncollagenous (NC1) domain of human placenta collagen IV shows stabilization via a novel type of covalent Met-Lys cross-link. Proc Natl Acad Sci U S A.;99 l (10):6607-12.

(56) References Cited

OTHER PUBLICATIONS

Tobe et al. (1998) Evolution of neovascularization in mice with overexpression of vascular endothelial growth factor in photoreceptors. Invest Ophthalmol Vis Sci., 39(1):180-8.

Vanacore et al (2004) The alpha1.alpha2 network of collagen IV. Reinforced stabilization of the noncollagenous domain-1 by noncovalent forces and the absence of Met-Lys cross-links. J Biol Chem; 279(43):44723-30. Epub Aug. 5, 2004.

Voet et al, (1995) Biochemistry, John Wiley & Sons Inc., pp. 235-241.

Xu et al (2001) Proteolytic exposure of a cryptic site within collagen type IV is required for angiogenesis and tumor growth in vivo. J Cell Biol.154(5)1 069-79.

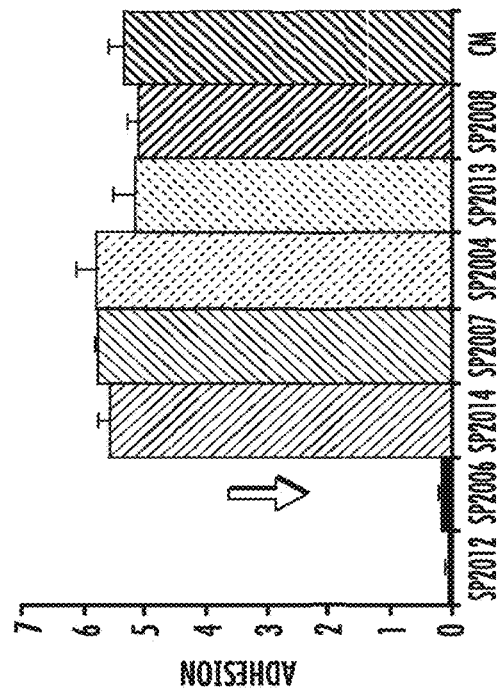
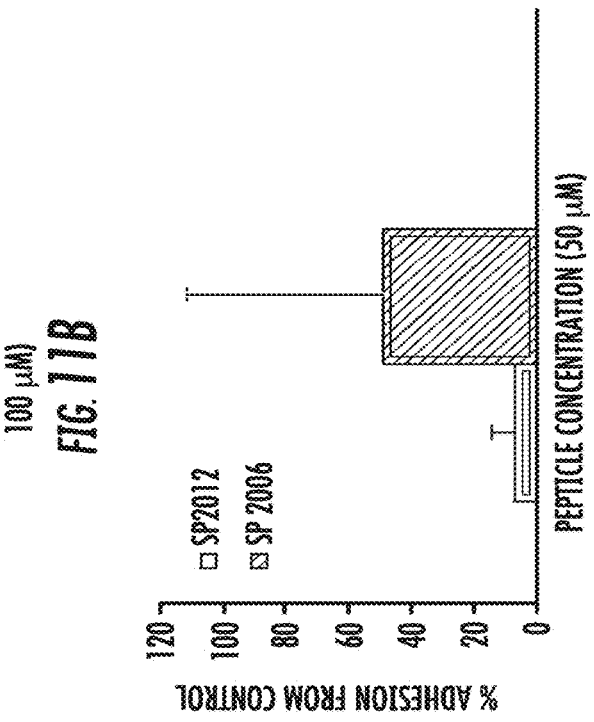
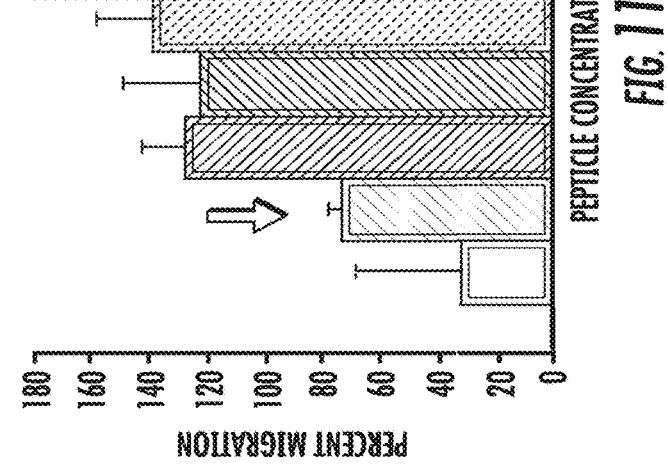

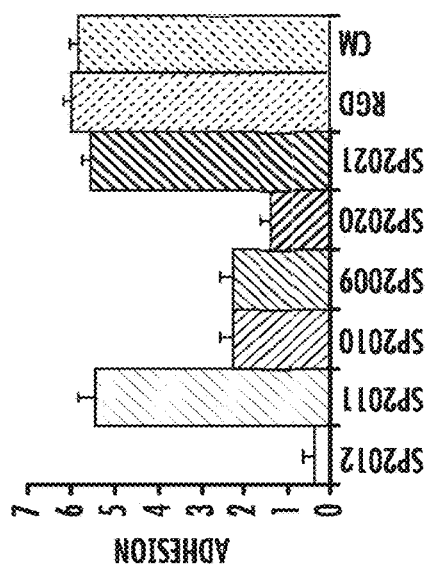
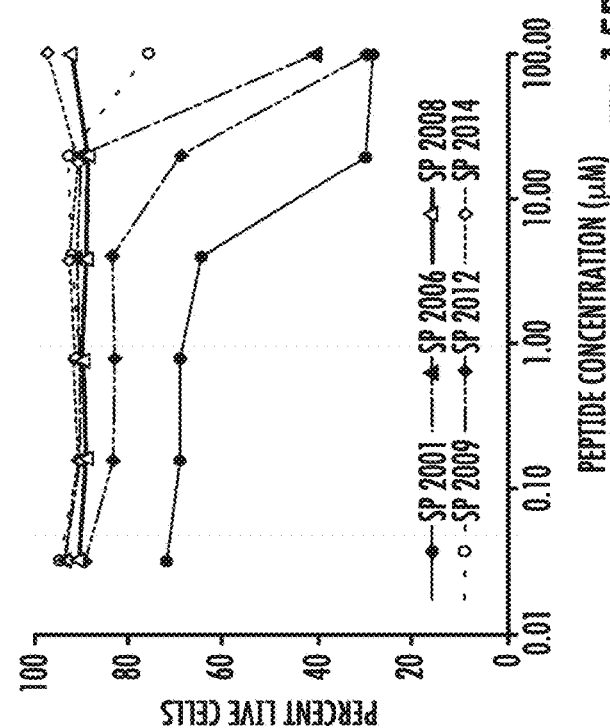
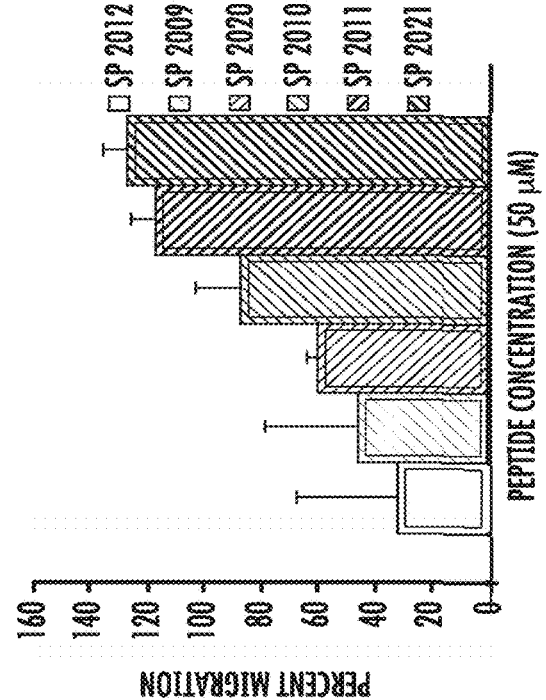
FIG. 15A, FIG. 15B, FIG. 15C, FIG. 15D

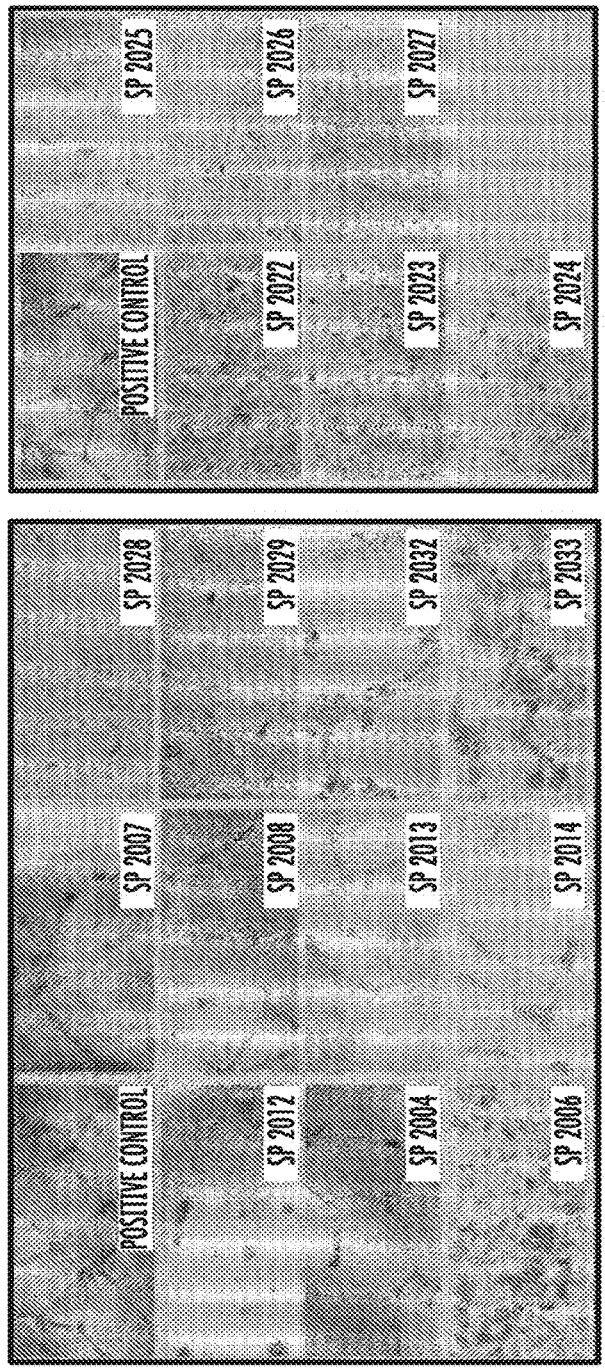
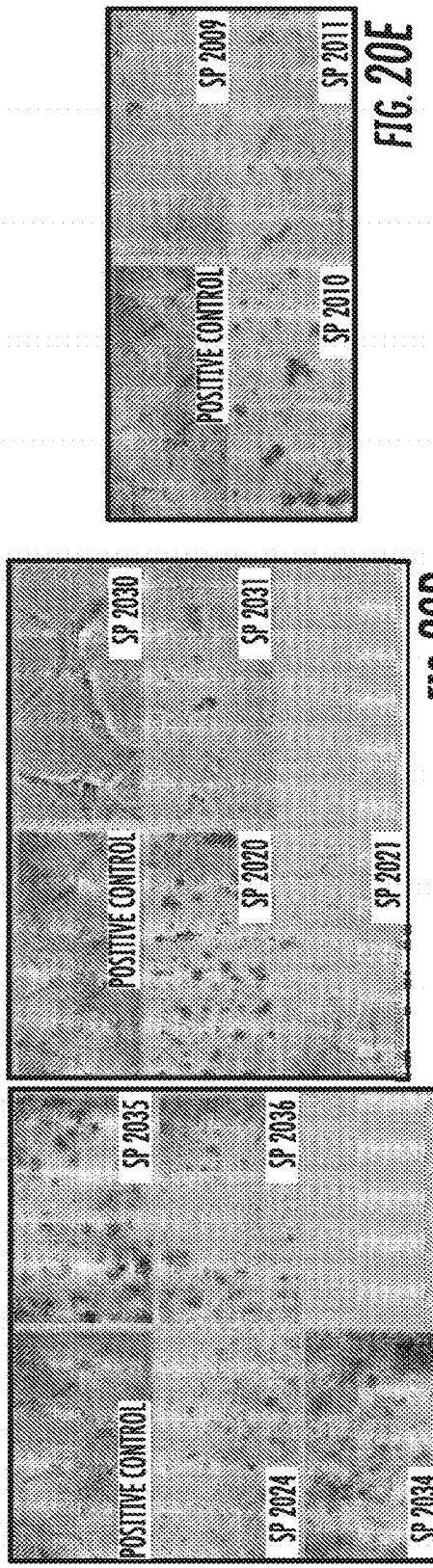
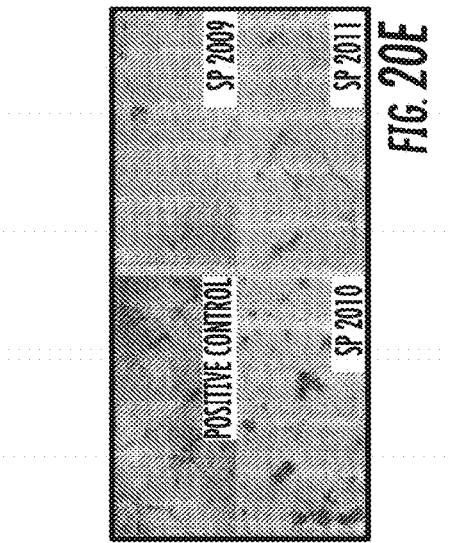
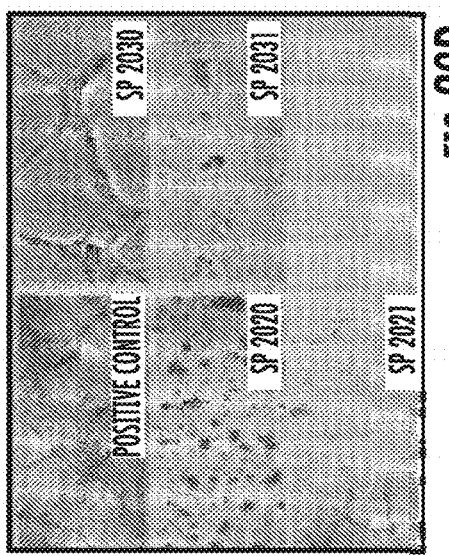

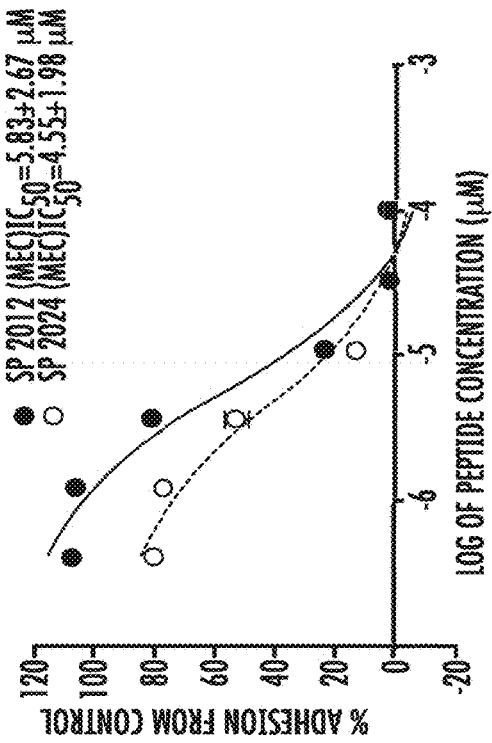
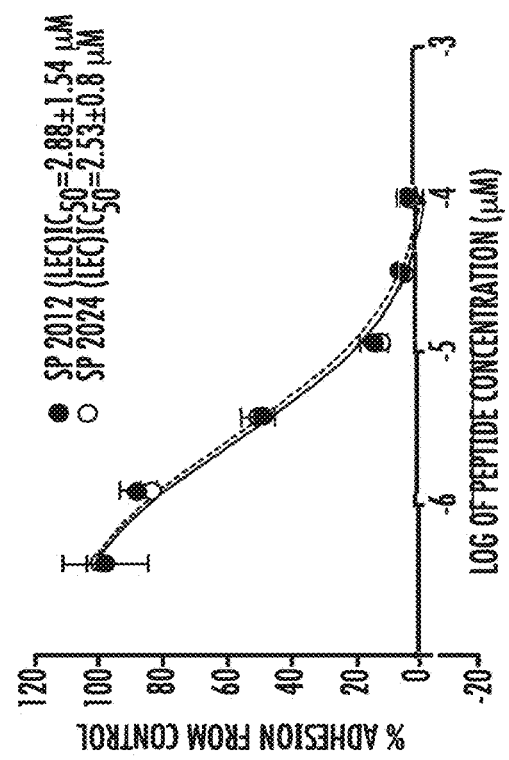
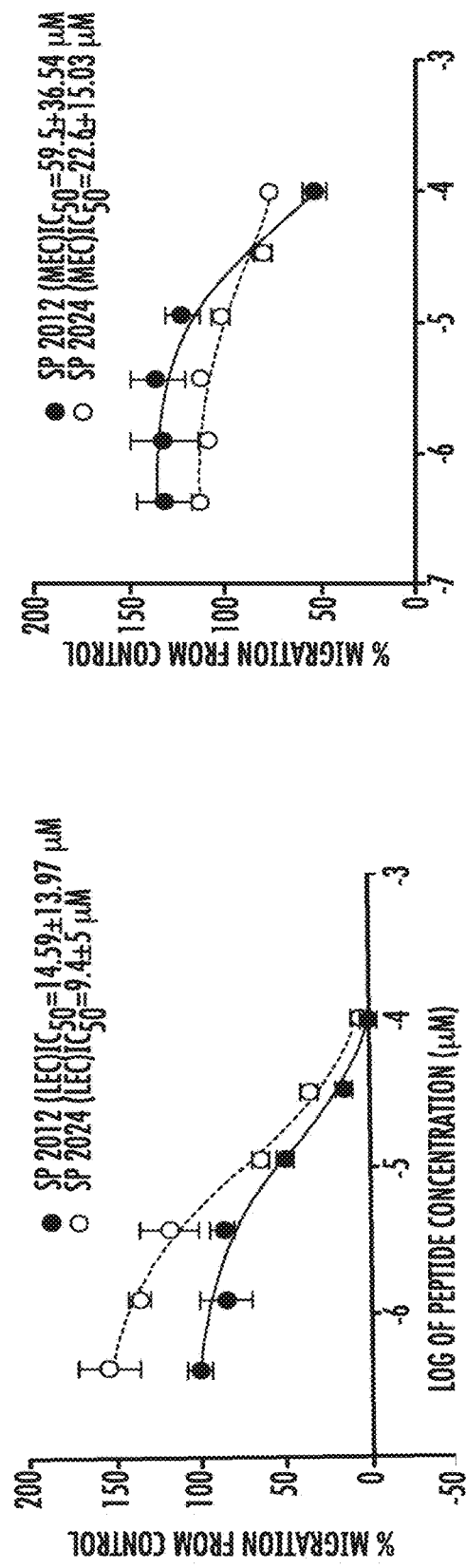
FIG. 21A
FIG. 21B
FIG. 21C
FIG. 21D

US 11,155,603 B2

MIMETIC PEPTIDES DERIVED FROM COLLAGEN TYPE IV AND THEIR USE FOR TREATING ANGIOGENESIS- AND LYMPHANGIOGENESIS- DEPENDENT DISEASES

CROSS REFERENCE TO RELATED APPLICATIONS

This application is a Continuation of U.S. application Ser. No. 15/395,648 filed Dec. 30, 2016, which is a Continuation of U.S. application Ser. No. 14/708,829 filed May 11, 2015, which is a Divisional of U.S. application Ser. No. 13/992,998, filed on Aug. 7, 2013 (and Patented as U.S. Pat. No. 9,056,923 on Jun. 16, 2015), which is a 35 U.S.C. § 371 National Stage Entry of International Application No. PCT/US2011/064475 having an international filing date of Dec. 12, 2011, which claims the benefit of U.S. Provisional Application No. 61/421,706 filed Dec. 10, 2010, and U.S. Provisional Application No. 61/546,314 filed Oct. 12, 2011. Each of the aforementioned applications is incorporated herein by reference in its entirety.

FEDERALLY SPONSORED RESEARCH OR DEVELOPMENT

This invention was made with government support under R21 CA131931 and R01 CA138264 awarded by the National Institutes of Health. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "ASX-005C3-SequenceListing_ST25". The sequence listing is about 13 kb in size, and was created on or about Sep. 13, 2018. It is hereby incorporated by reference in its entirety.

BACKGROUND

Cancer is a major public health problem in the United States and other parts of the world. Currently, 1 in 4 deaths in the United States is due to cancer. Angiogenesis plays a critical role in tumor growth and metastasis in most types of cancer. In particular, its importance has been demonstrated in breast cancer, the most commonly diagnosed female malignancy in the United States. Anti-angiogenic therapeutics, either as a monotherapy or in combination with other therapeutics, are promising and are being intensely investigated in both preclinical and clinical studies. Anti-VEGF therapeutics showed early promise in clinical trials; however, although an anti-VEGF antibody bevacizumab (Genentech/Roche) was approved by the FDA for breast cancer in 2008 in combination with chemotherapy, in November 2011, the FDA revoked the breast cancer indication because it has not demonstrated an overall survival benefit. Accordingly, the development of anti-angiogenic therapies to treat breast and other cancers, as well as, ocular proliferative diseases, such as age-related macular degeneration, is ongoing. Lymphangiogenesis also plays an important role in cancer metastasis (Holopainen et al., 2011). To date no peptide drugs have been approved for the treatment of cancer or other angiogenesis- and lymphangiogenesis-dependent diseases.

Peptides have been employed as therapeutics for multiple diseases and recently have been investigated in clinical applications to target tumors either for imaging or therapy (Folkman, 2010; Senger et al., 1983; Leung et al., 1989; Carmeliet, 2005; Carmeliet and Jain, 2000; Carmeliet and Jain, 2011; Rosca et al., 2011). Mimetic peptides are peptides that biologically mimic active determinants on biomolecules. In general, peptides are attractive tools as therapeutics due to their specific target binding, ability to penetrate cells and ease of modification giving flexibility for different applications. (Carmeliet and Jain, 2000; Folkman, 2006) Some of the properties that make peptides attractive candidates, however, also contribute to their disadvantages. Although peptides can interact specifically with cellular receptors, sometimes these interactions may be of low affinity. In addition, the use of peptides as therapeutic agents is currently limited due to their short half-life and reduced bioavailability. Attempts to modify a peptide in order to increase its bioavailability include substitution with non-natural amino acids, pegylation of the peptide, and delivery of the peptide in a nano- or micro-particle.

SUMMARY

The presently disclosed subject matter provides peptide compositions, methods, and kits for treating a disease, disorder, or dysfunction that is related to angiogenesis, lymphangiogenesis, vascular permeability or tumorigenesis. The presently disclosed peptide compositions and methods, in some aspects, inhibit angiogenesis, lymphangiogenesis, vascular permeability or tumorigenesis which play a critical role in multiple diseases or disorders. Accordingly, in some aspects, the compositions and methods of the presently disclosed subject matter allow the prevention or reduction of blood vessel, lymphatic vessel, or tumor formation involving a cell, tissue or organ.

More particularly, in some aspects, the presently disclosed subject matter provides compositions and methods of treating at least one cell with an isolated peptide comprising the amino acid sequence LRRFSTXPXXXXNINNVXNF (SEQ ID No:1), wherein X is any naturally occurring or non-naturally occurring amino acid.

In one aspect, the presently disclosed subject matter provides an isolated peptide comprising the amino acid sequence LRRFSTXPXXXXNINNVXNF (SEQ ID No:1), wherein X is any amino acid and wherein the peptide does not comprise LRRFSTMPFMFCNINNVCNF (SEQ ID No:19).

In another aspect, the presently disclosed subject matter provides an isolated peptide comprising the amino acid sequence LRRFSTXPXXXXNINNVXNF (SEQ ID No:1), wherein X at position 7 is M, A, or G; X at position 9 is F, A, Y, or G; X at position 10 is M, A, G, dA, or Nle; X at position 11 is F, A, Y, G, or 4-C1Phe; X at position 12 and position 18 are Abu, G, S, A, V, T, I, L or AllyGly; and wherein the peptide does not comprise LRRFSTMPFMFC-NINNVCNF (SEQ ID No:19).

In a further aspect, the presently disclosed subject matter provides an isolated peptide comprising at least one of the following amino acid sequences:

LRRFSTMPFMFAbuNINNVAbuNF; (SEQ ID No: 3)

LRRFSTMPAMFAbuNINNVAbuNF; (SEQ ID No: 4)

-continued

LRRFSTMPFAFAbuNINNVAbu NF; (SEQ ID No: 5)

LRRFSTMPFMAAbuNINNVAbuNF; (SEQ ID No: 6)

LRRFSTMPFN1eFAbuNINNVAbuNF; (SEQ ID No: 7)

LRRFSTMPFM4-C1PheAbuNINNVAbuNF; (SEQ ID No. 8)

LRRFSTMPFMFGNINNVGNF; (SEQ ID No: 2)

LRRFSTMPFMFSNINNVSNF; (SEQ ID No: 9)

LRRFSTMPFMFANINNVANF; (SEQ ID No: 10)

LRRFSTMPFMFVNINNVVNF; (SEQ ID No: 14)

LRRFSTMPFMFTNINNVTNF; (SEQ ID No: 12)

LRRFSTMPFMFAllyGlyNINNVAllyGlyNF; (SEQ ID No: 13)

LRRFSTMPFMFININNVINF; (SEQ ID No: 11)

LRRFSTMPFdAFININNVINF; (SEQ ID No. 15)

LRRFSTAPFMFININNVINF;
and (SEQ ID No. 16)

LRRFSTAPFAFININNVINF. (SEQ ID No. 17)

In another aspect, the presently disclosed subject matter provides compositions and kits comprising a pharmaceutically acceptable carrier and an effective amount of at least one of the peptide sequences disclosed herein. The compositions and kits prevent or reduce blood vessel, lymphatic vessel, or tumor formation involving a cell, tissue, or organ. The compositions and kits may also inhibit vascular permeability involving a cell, tissue, or organ.

In a further aspect, the presently disclosed subject matter provides a method for inhibiting angiogenesis, lymphangiogenesis, vascular permeability and/or tumorigenesis involving a cell. The method comprises contacting a cell with a presently disclosed isolated peptide in an amount sufficient to inhibit angiogenesis, lymphangiogenesis, vascular permeability, and/or tumorigenesis of the cell or involving the cell. The contacting of the cell may result in an inhibition of adhesion, migration, proliferation, and/or tube formation of the cell.

Certain aspects of the presently disclosed subject matter provide for the use of the isolated peptides in the treatment of a disease associated with angiogenesis, lymphangiogenesis, vascular permeability, and/or tumorigenesis. The presently disclosed subject matter provides a method of treating a subject suffering from a disease related to angiogenesis, lymphangiogenesis, vascular permeability, and/or tumorigenesis or preventing or delaying a subject from getting a disease related to angiogenesis, lymphangiogenesis, vascular permeability, and/or tumorigenesis. The method comprises administering to the subject an isolated peptide of the present invention in an amount sufficient to treat, delay, or prevent the disease in the subject. The disease may be a cancer or the disease may be related to ocular angiogenesis or other angiogenesis-, tumorigenesis-, vascular permeability-, or lymphangiogenesis-dependent diseases.

The method of the presently disclosed subject matter can be practiced in vivo as either a therapeutic method of treating a disease or disorder involving angiogenesis, lymphangiogenesis, vascular permeability, or tumorigenesis or as a prophylactic method to prevent angiogenesis, lymphangiogenesis, vascular permeability, or tumorigenesis. Likewise, the method can be practiced in vitro as a research tool to study the effects of angiogenesis, lymphangiogenesis, vascular permeability or tumorigenesis. The method also can be practiced ex vivo for therapeutic or research purposes.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
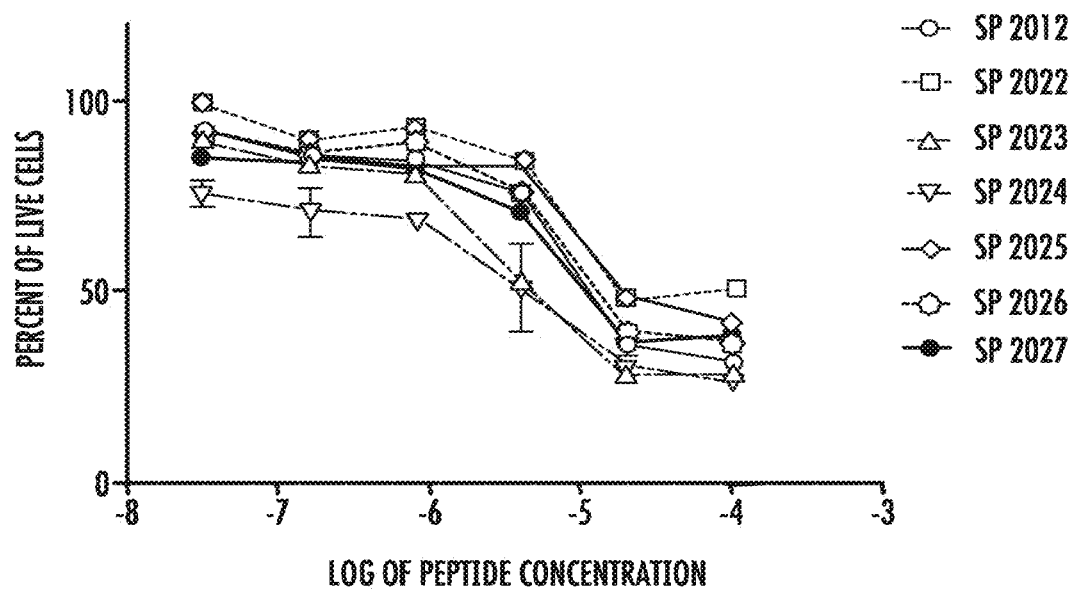
Figure 2:
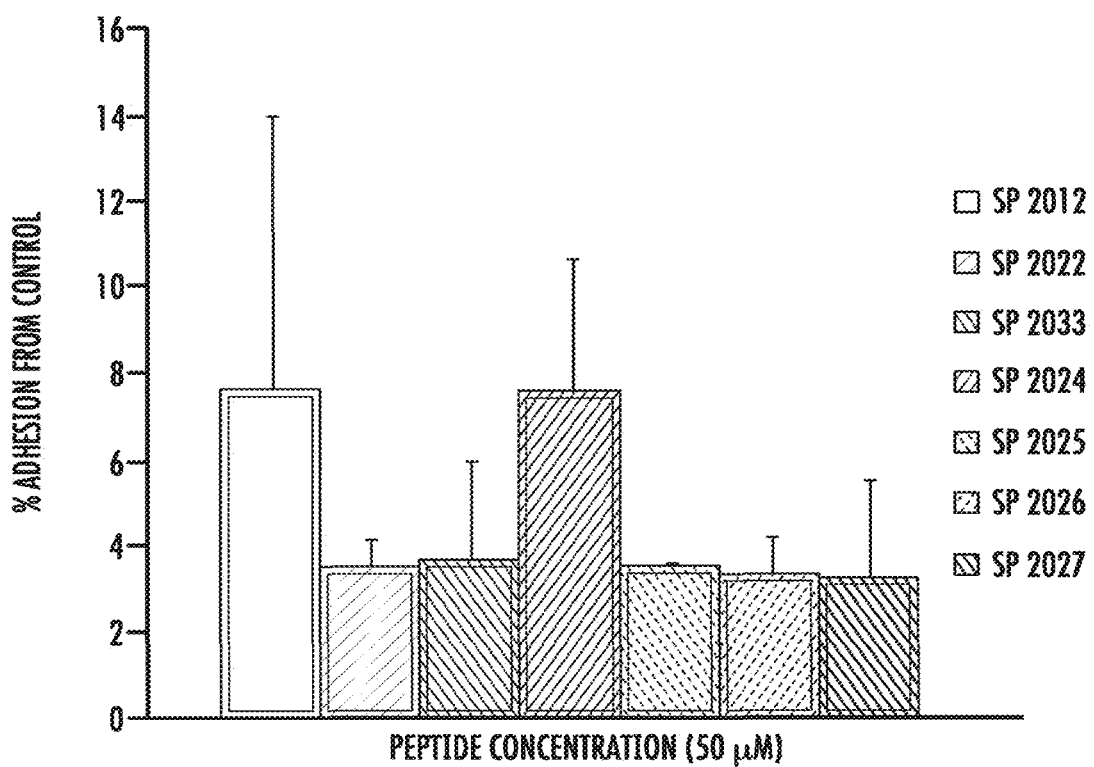
Figure 3:
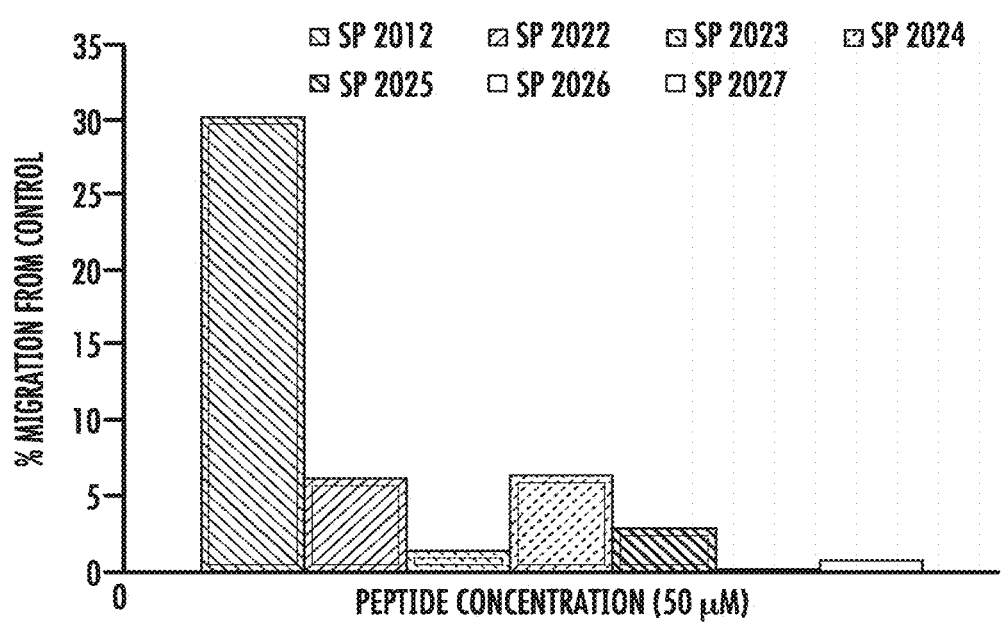
Figure 4A:
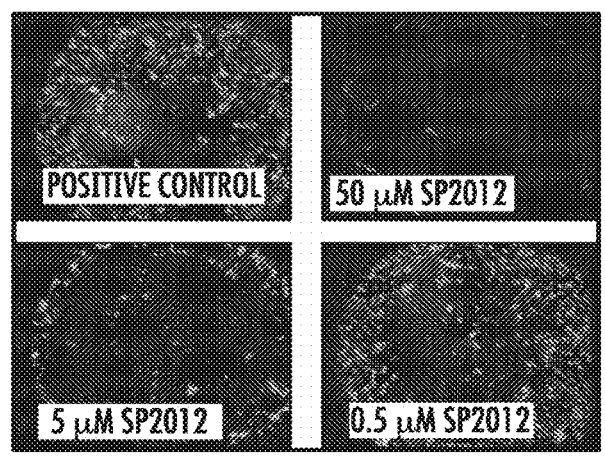
Figure 4B:
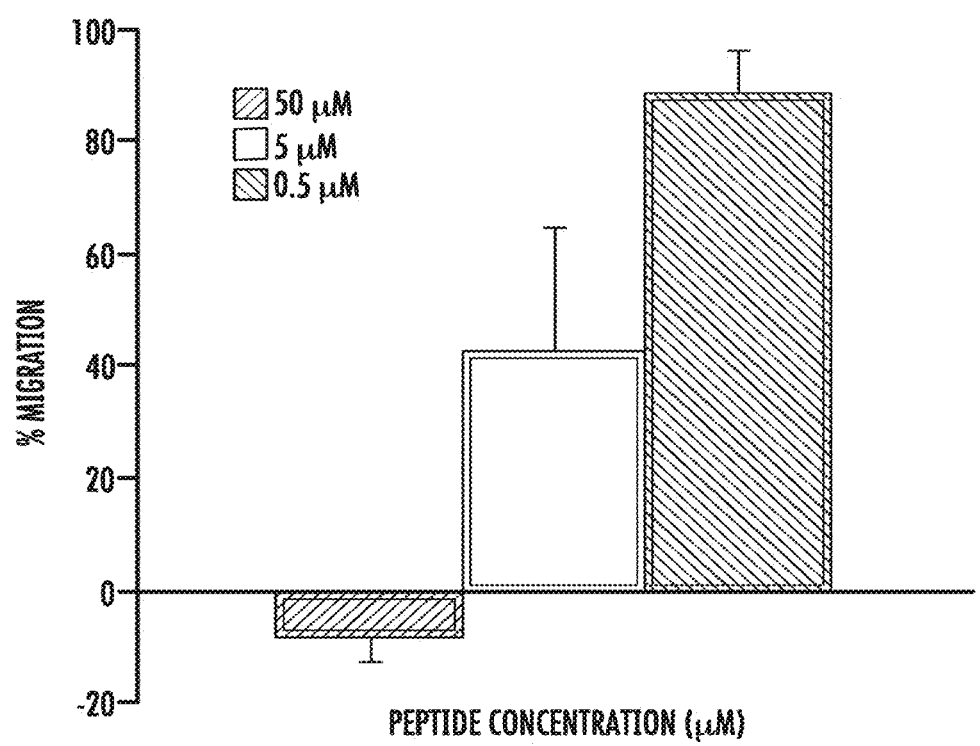
Figure 5A:
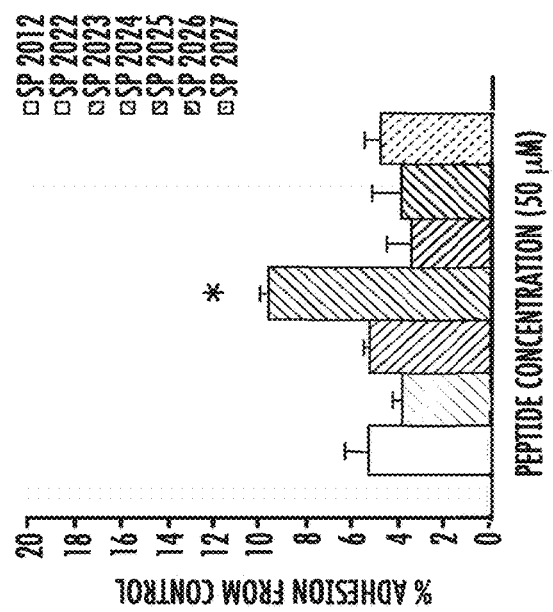
Figure 5B:
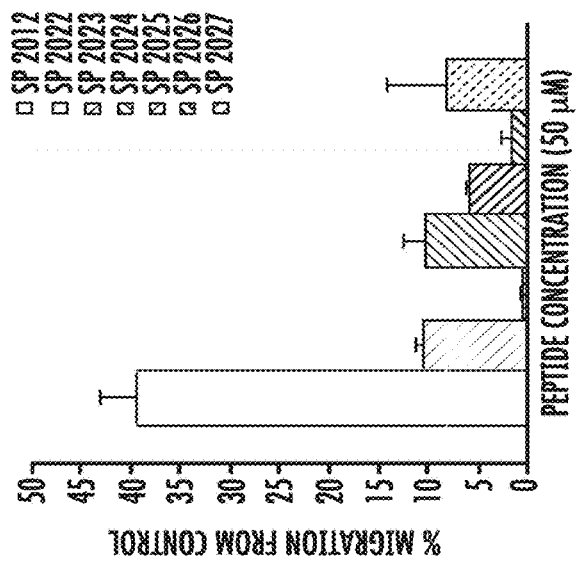
Figure 5C:
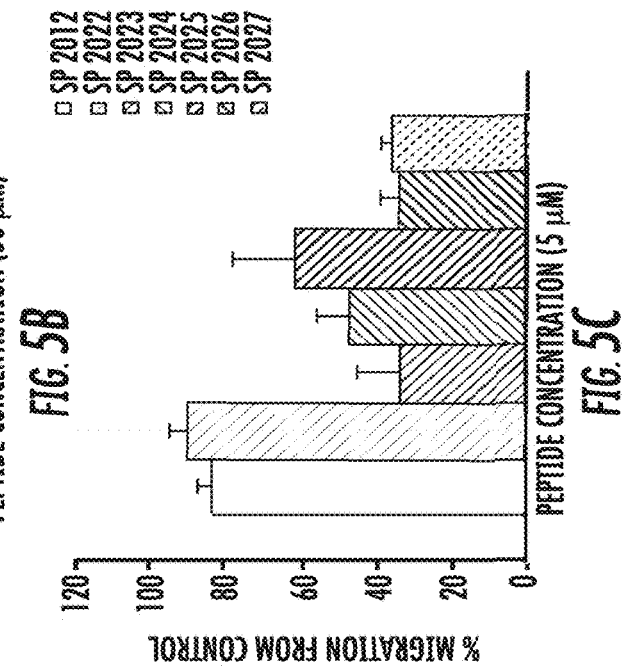
Figure 6A:
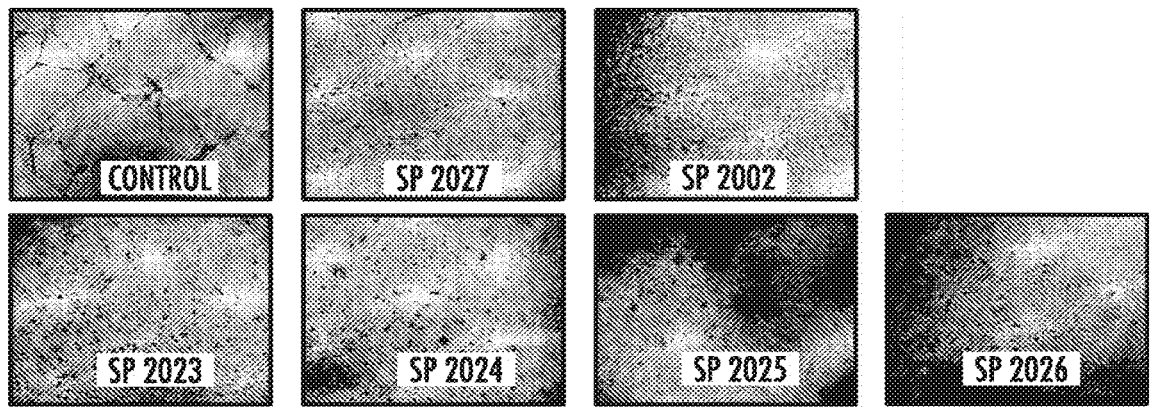
Figure 6B:
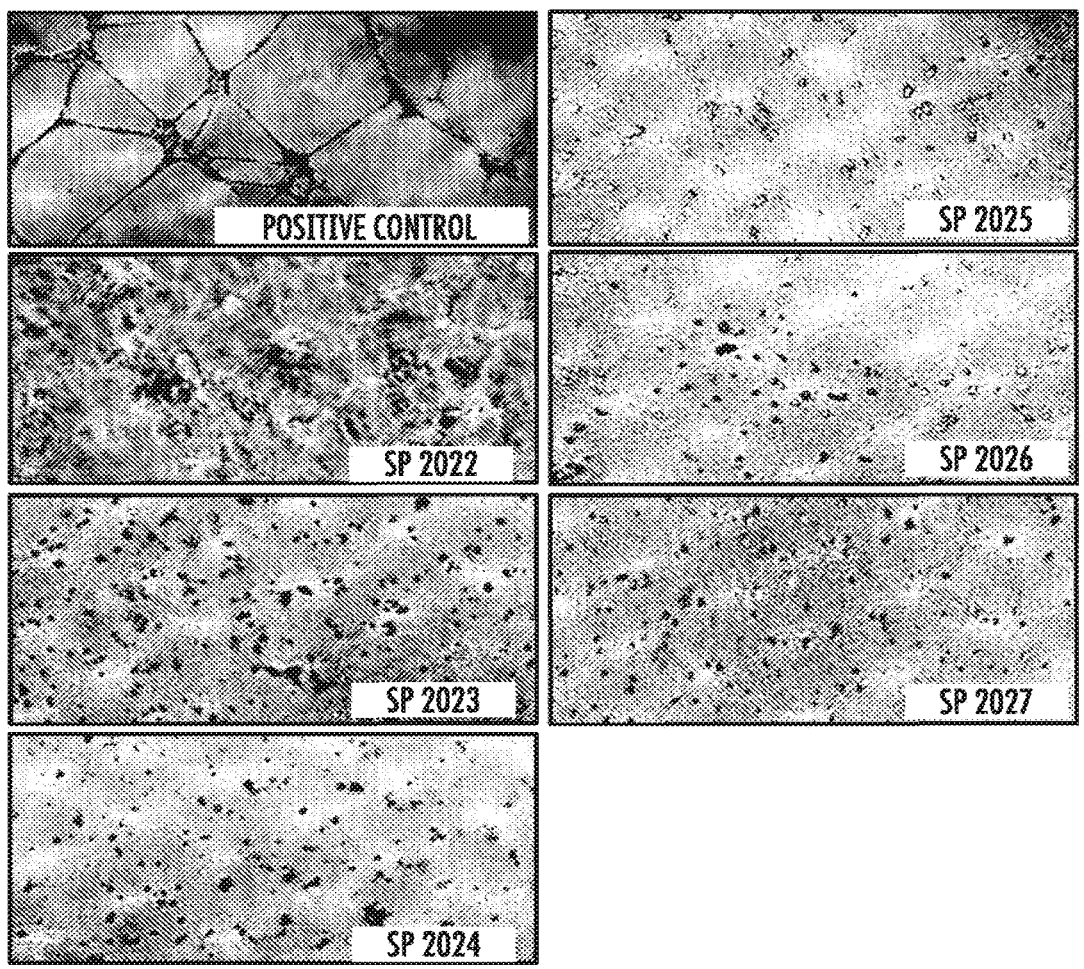
Figure 7:
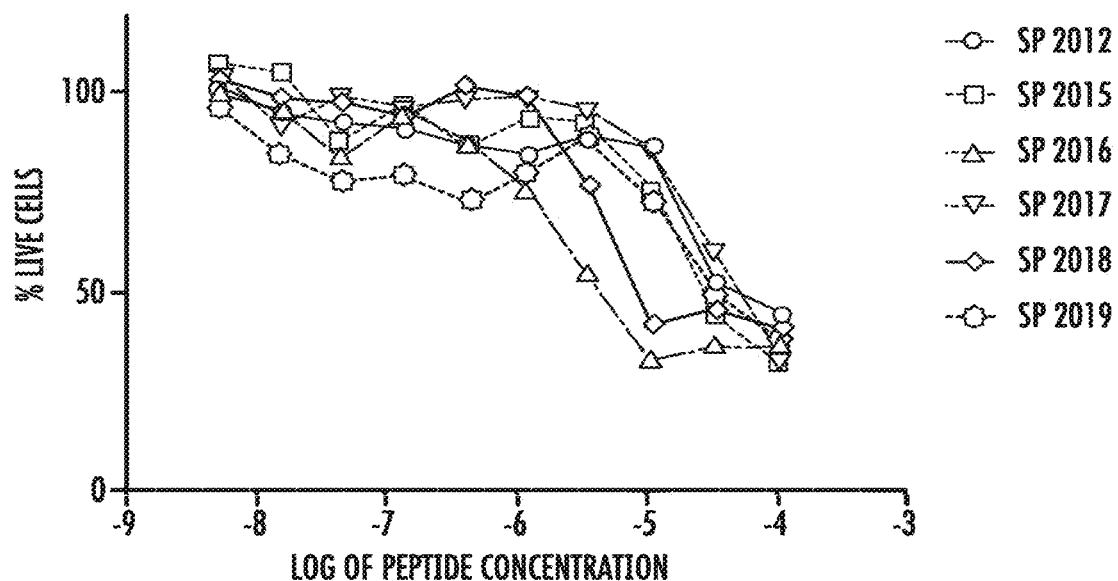
Figure 8:
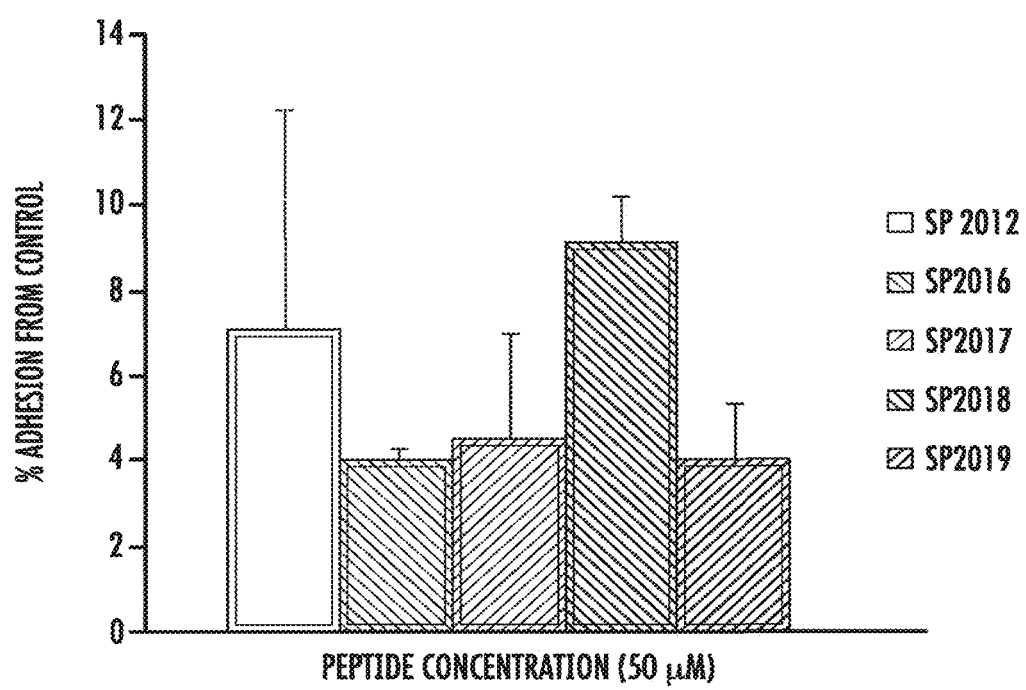
Figure 9:
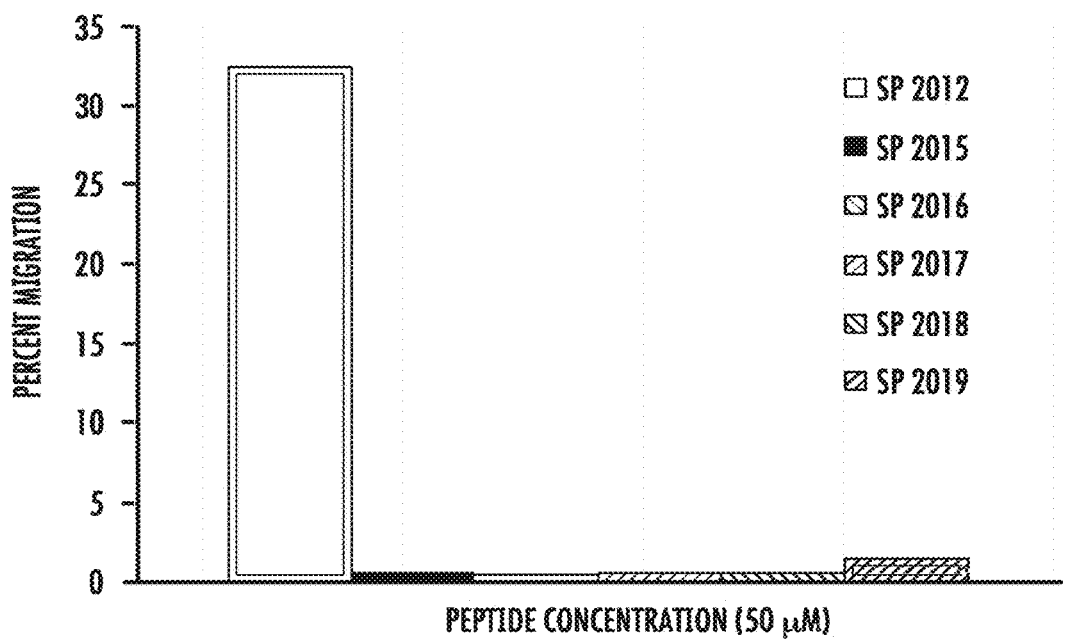
Figure 10:
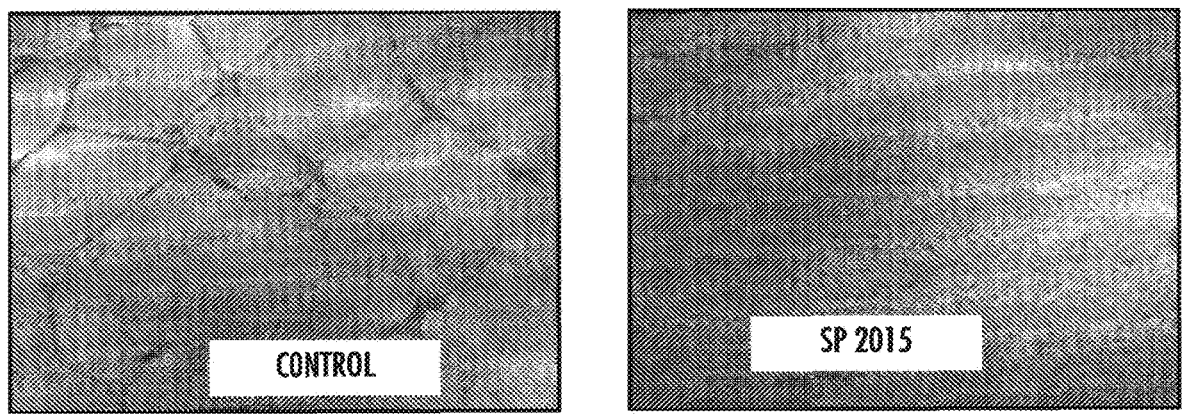
Figure 12A:
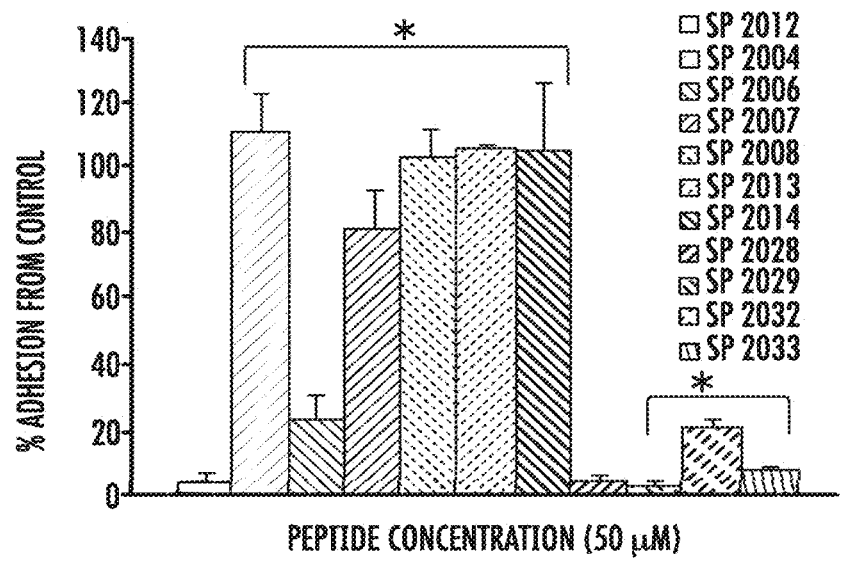
Figure 12B:
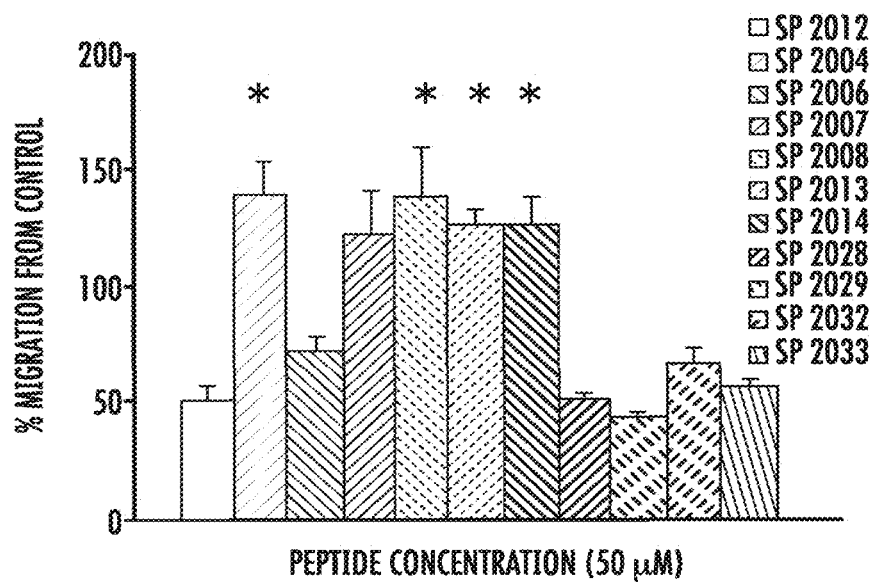
Figure 13:
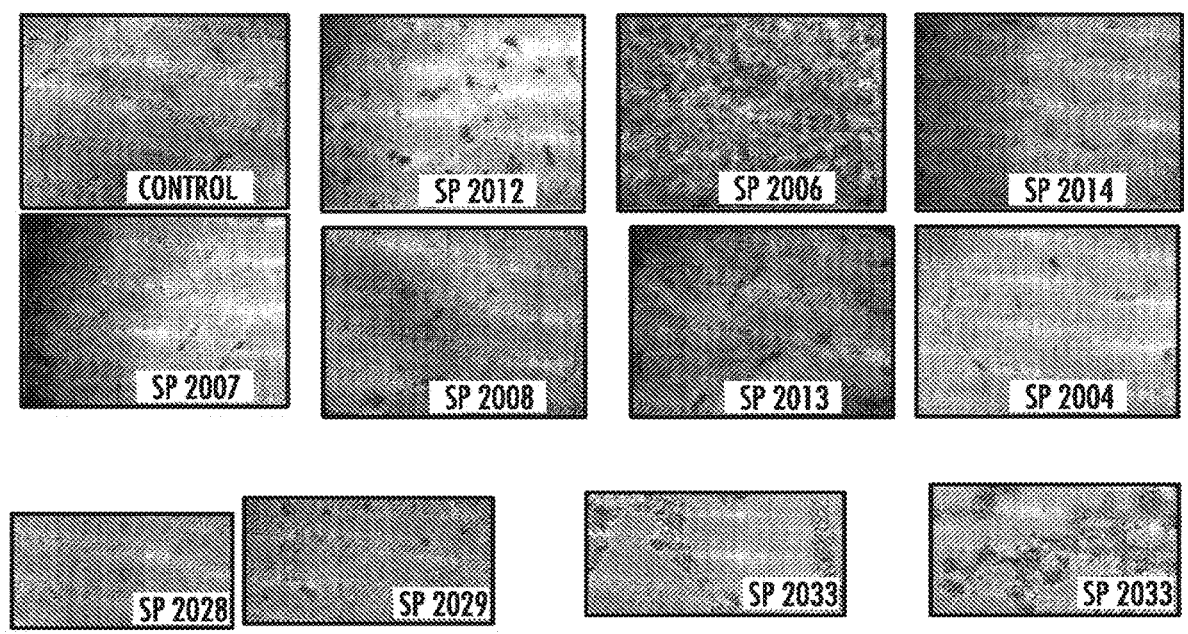

Having thus described the presently disclosed subject matter in general terms, reference will now be made to the accompanying Figures, which are not necessarily drawn to scale, and wherein:

FIG. 1 shows the results from a proliferation assay for the full length peptides with substituted Cysteines (SP2022-SP2027; SEQ ID Nos:9-14);

FIG. 2 illustrates an adhesion assay for the full length peptides with substituted Cysteines (SP2022-SP2027; SEQ ID Nos:9-14);

FIG. 3 demonstrates a migration assay for the full length peptides with substituted Cysteines (SP2022-SP2027; SEQ ID Nos:9-14);

FIGS. 4A and 4B show a wound healing assay with varied concentrations of peptide SP2012 (Panel A) and quantification of the assay (Panel B);

FIGS. 5A-5C illustrate an adhesion assay (Panel A), a migration assay at 50 µM (Panel B), and a migration assay at 5 µM (Panel C) for the full length peptides with substituted Cysteines (SP2022-SP2027; SEQ ID Nos:9-14);

FIG. 6A and FIG. 6B demonstrates a tube formation assay for the full length peptides with substituted Cysteines (SP2022-SP2027; SEQ ID Nos:9-14);

FIG. 7 shows the results from a proliferation assay for the full length peptides with Alanine and other substitutions (SP2015-SP2019; SEQ ID Nos:4-8);

FIG. 8 illustrates an adhesion assay for the full length peptides with Alanine and other substitutions (SP2016-SP2019; SEQ ID Nos:5-8);

FIG. 9 demonstrates a migration assay for the full length peptides with Alanine and other substitutions (SP2015-SP2019; SEQ ID Nos:4-8);

FIG. 10 shows a tube formation assay for the peptide SP2015 (SEQ ID No:4);

FIGS. 11A-11D illustrate the amino acid sequences of the C-terminal deletion peptides (SP2000 is SEQ ID No: 19, SP2004 is SEQ ID No: 28, SP2013 is SEQ ID No: 26, SP2008 is SEQ ID No: 25, SP2014 is SEQ ID No: 27, SP2012 is SEQ ID No. 3, SP2006 is SEQ ID No. 18, and SP2007 is SEQ ID No. 24) (Panel A), an adhesion assay with these peptides (Panel B), a migration assay (Panel C), and inhibition of adhesion for SP2006 (SEQ ID No:18) (Panel D);

FIGS. 12A and 12B demonstrate the inhibitory activity of the C-terminal deletion peptides in an adhesion assay (Panel A) and in a migration assay (Panel B);

FIG. 13 shows a tube formation assay for the C-terminal deletion peptides.

Figure 14A:
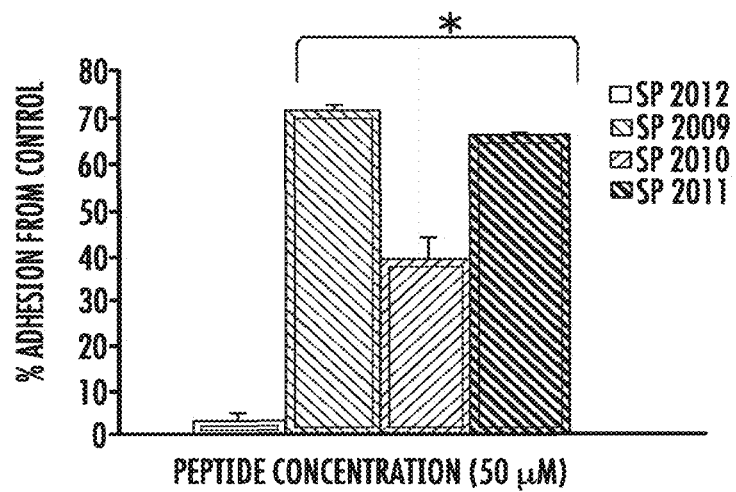
Figure 14B:
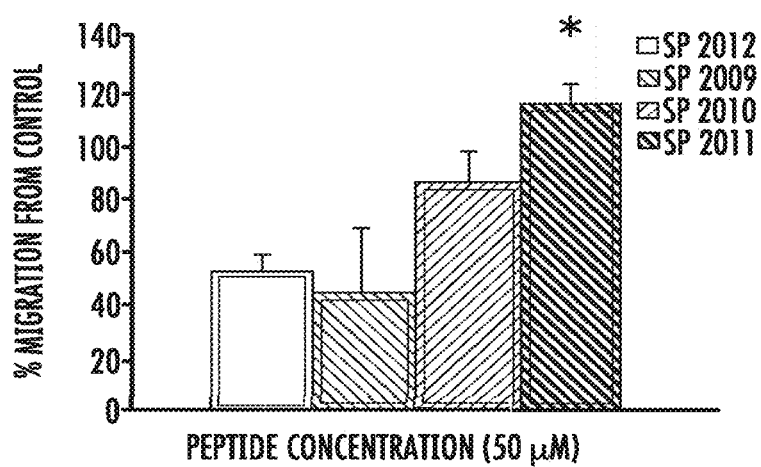
Figure 16A:
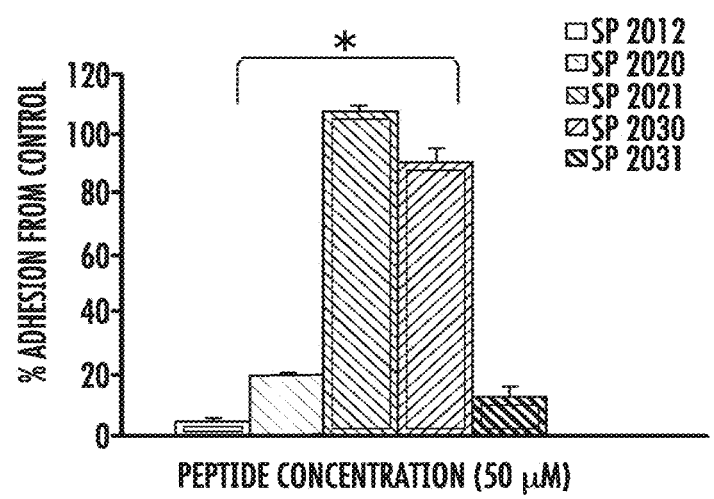
Figure 16B:
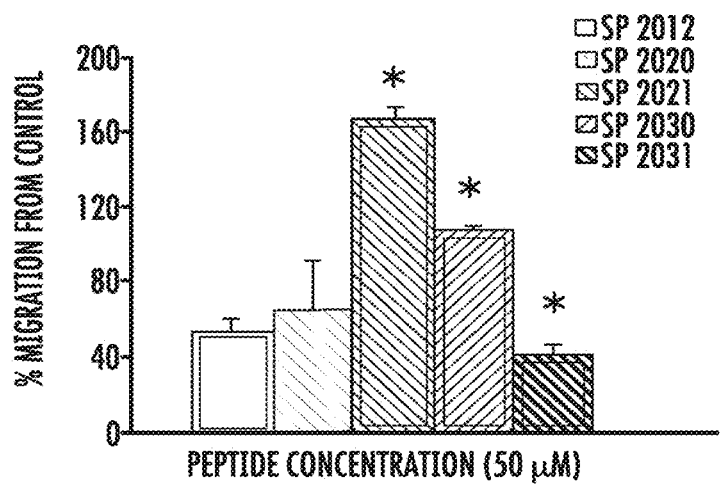
Figure 17:
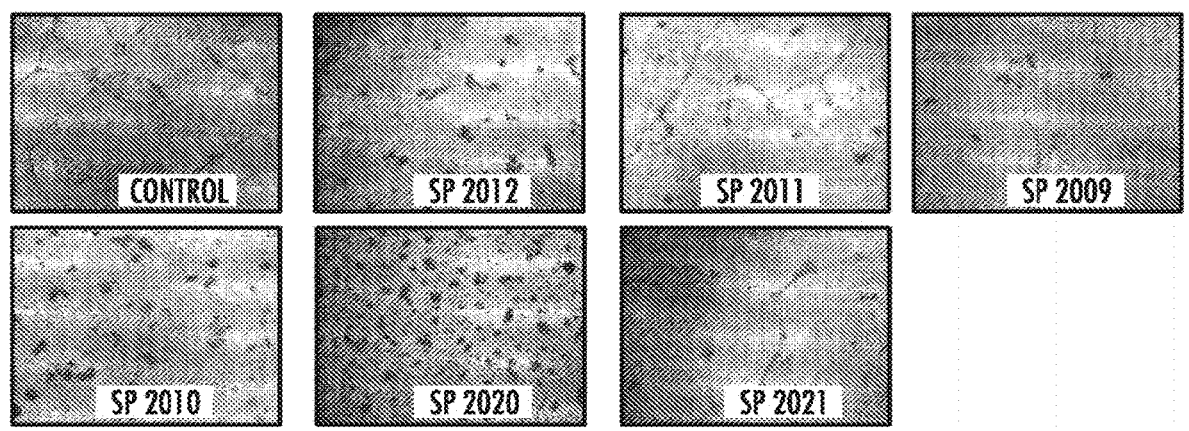
Figure 18A:
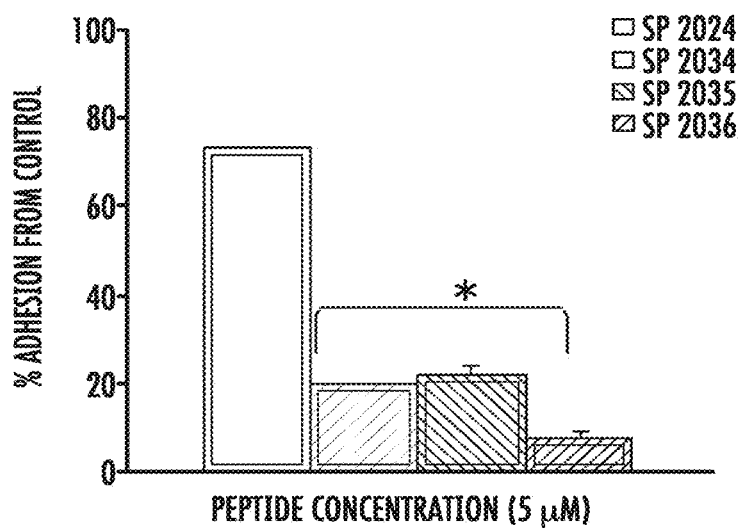
Figure 18B:
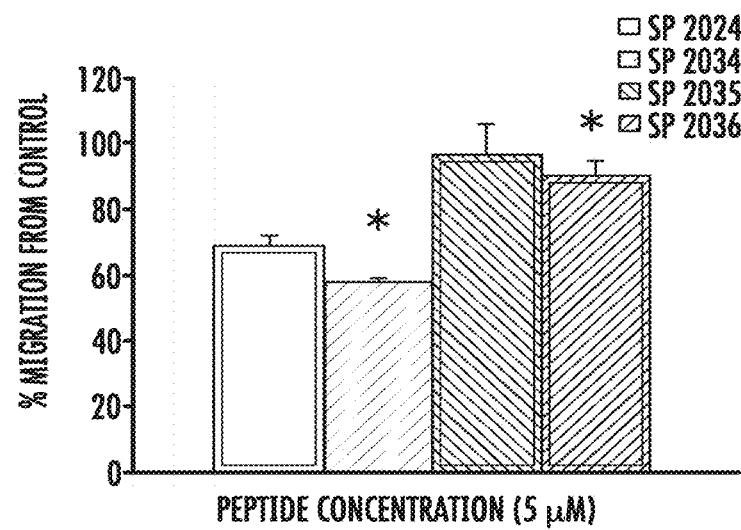
Figure 19A:
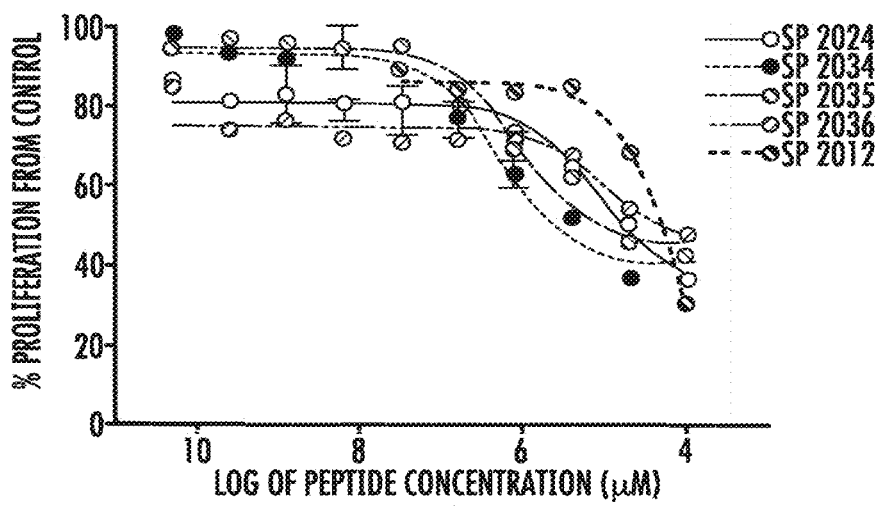
Figure 19B:
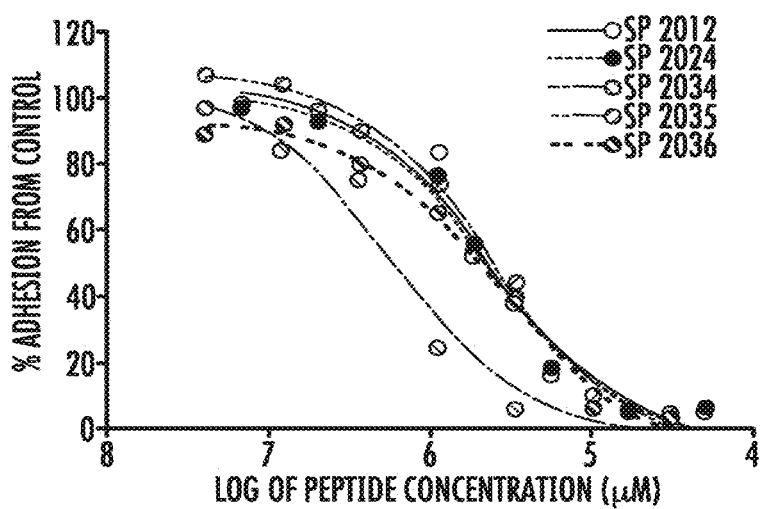
Figure 21E:
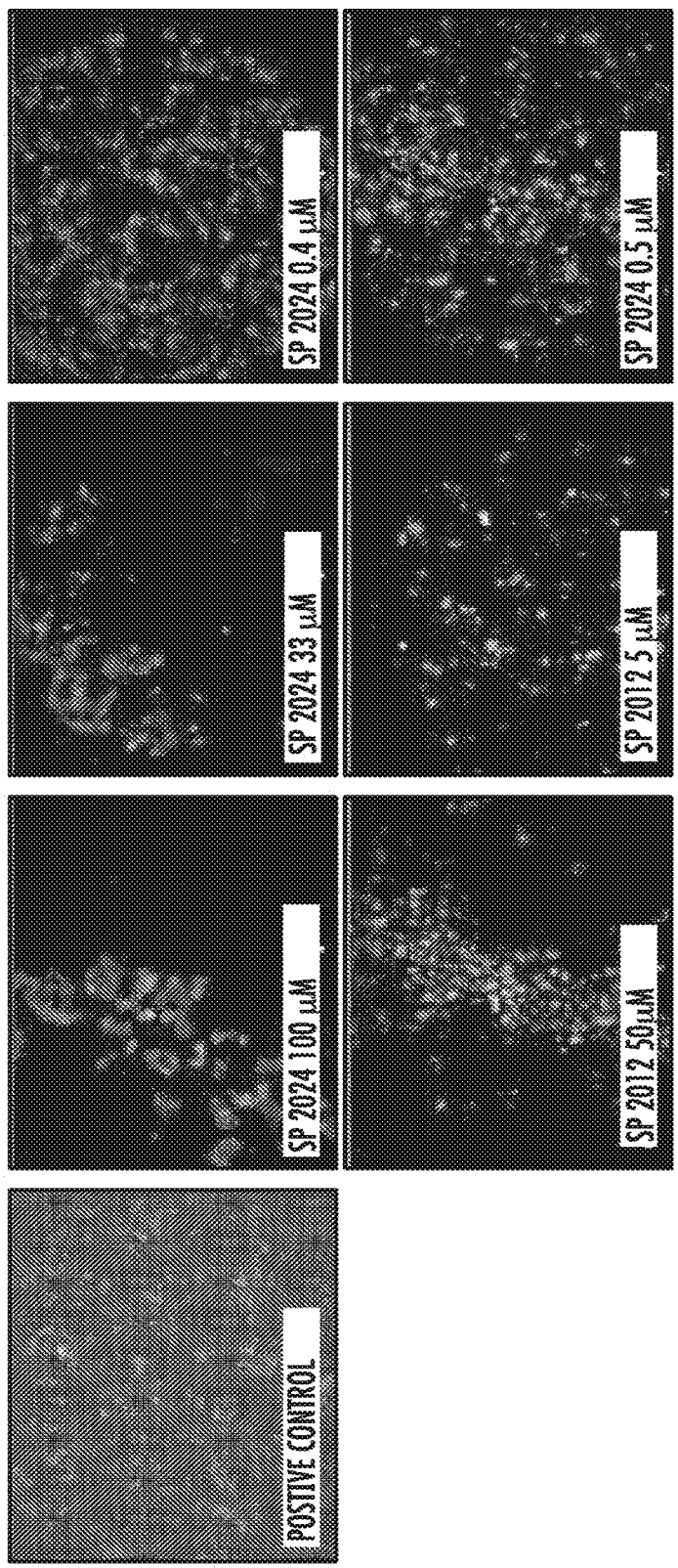
Figure 22A:
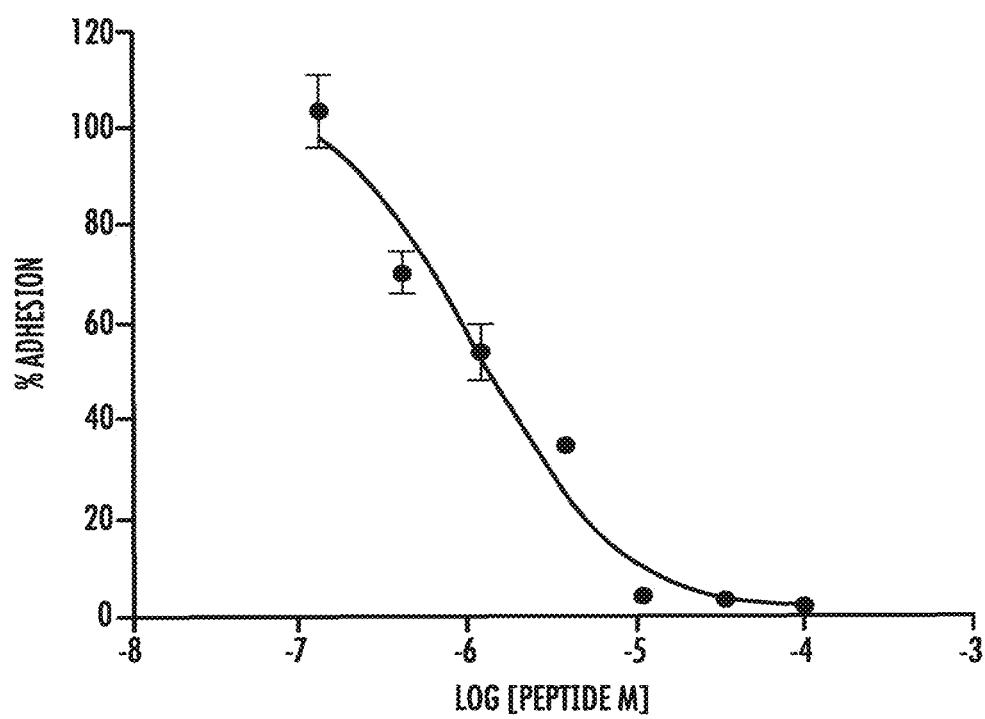
Figure 22B:
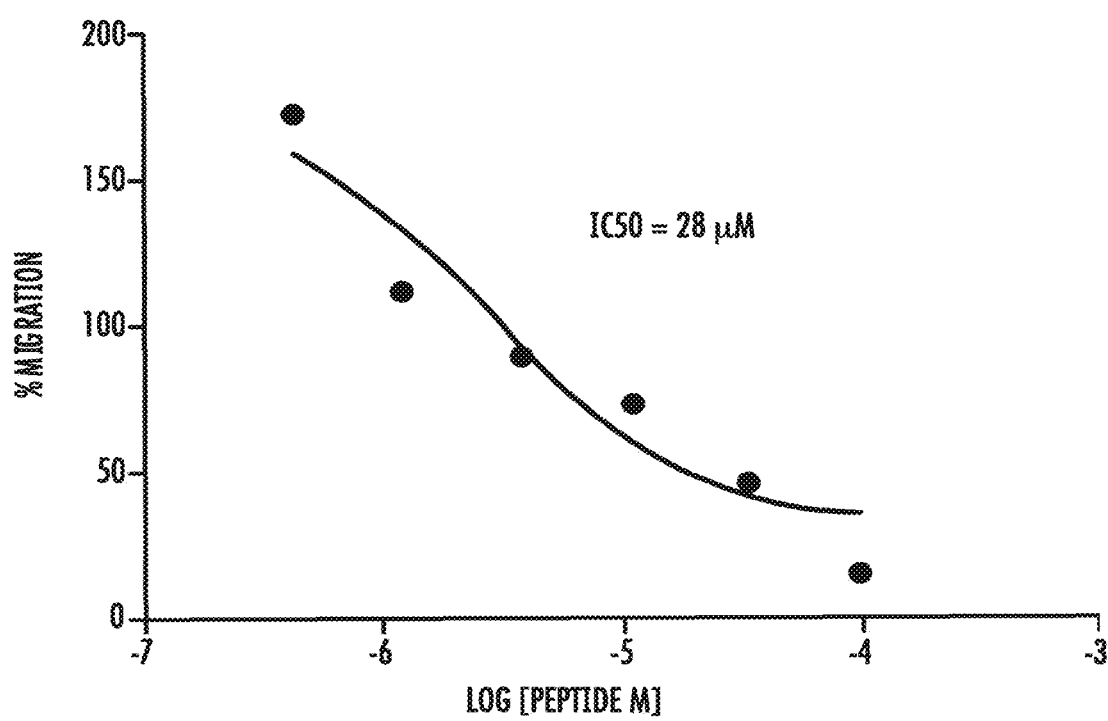
Figure 23A:
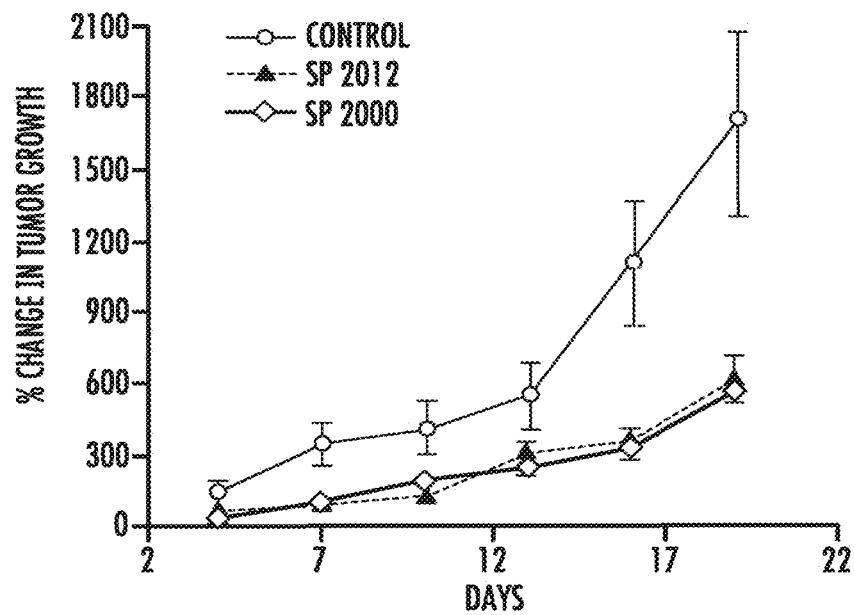
Figure 23B:
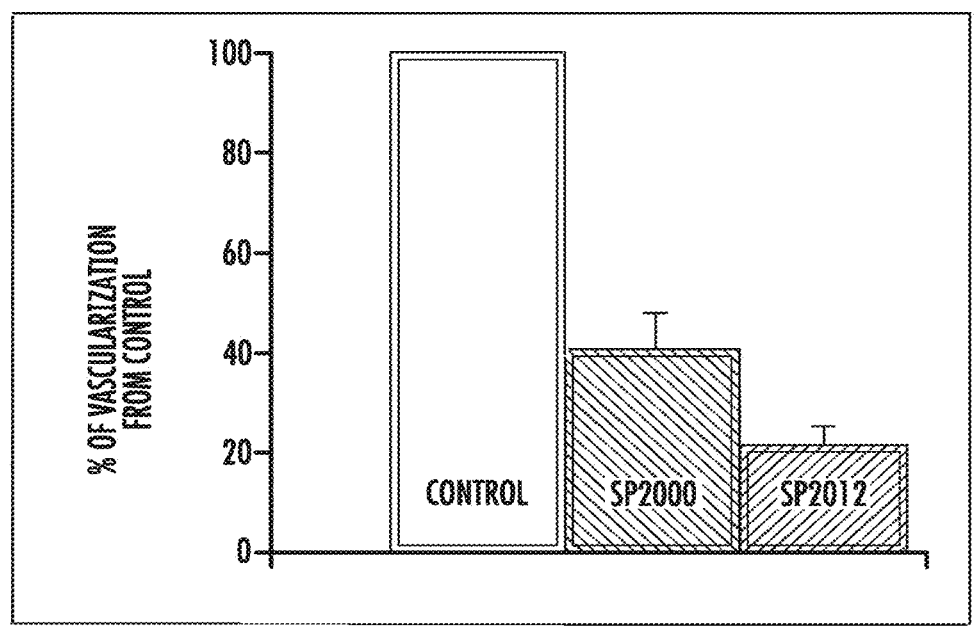
Figure 24A:
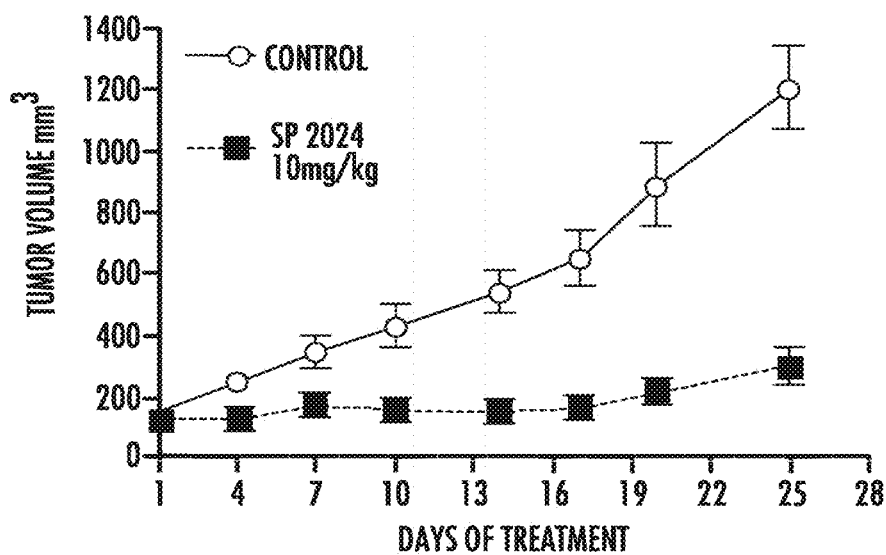
Figure 24B:
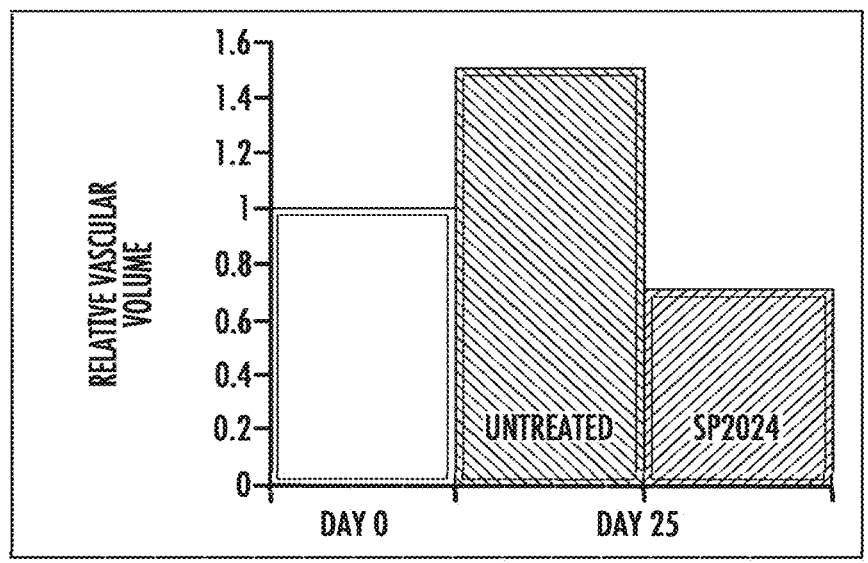
Figure 24C:
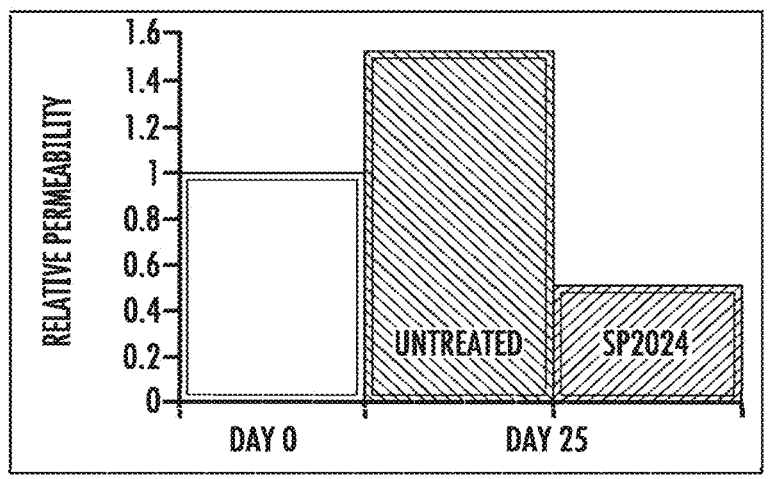
Figure 25:
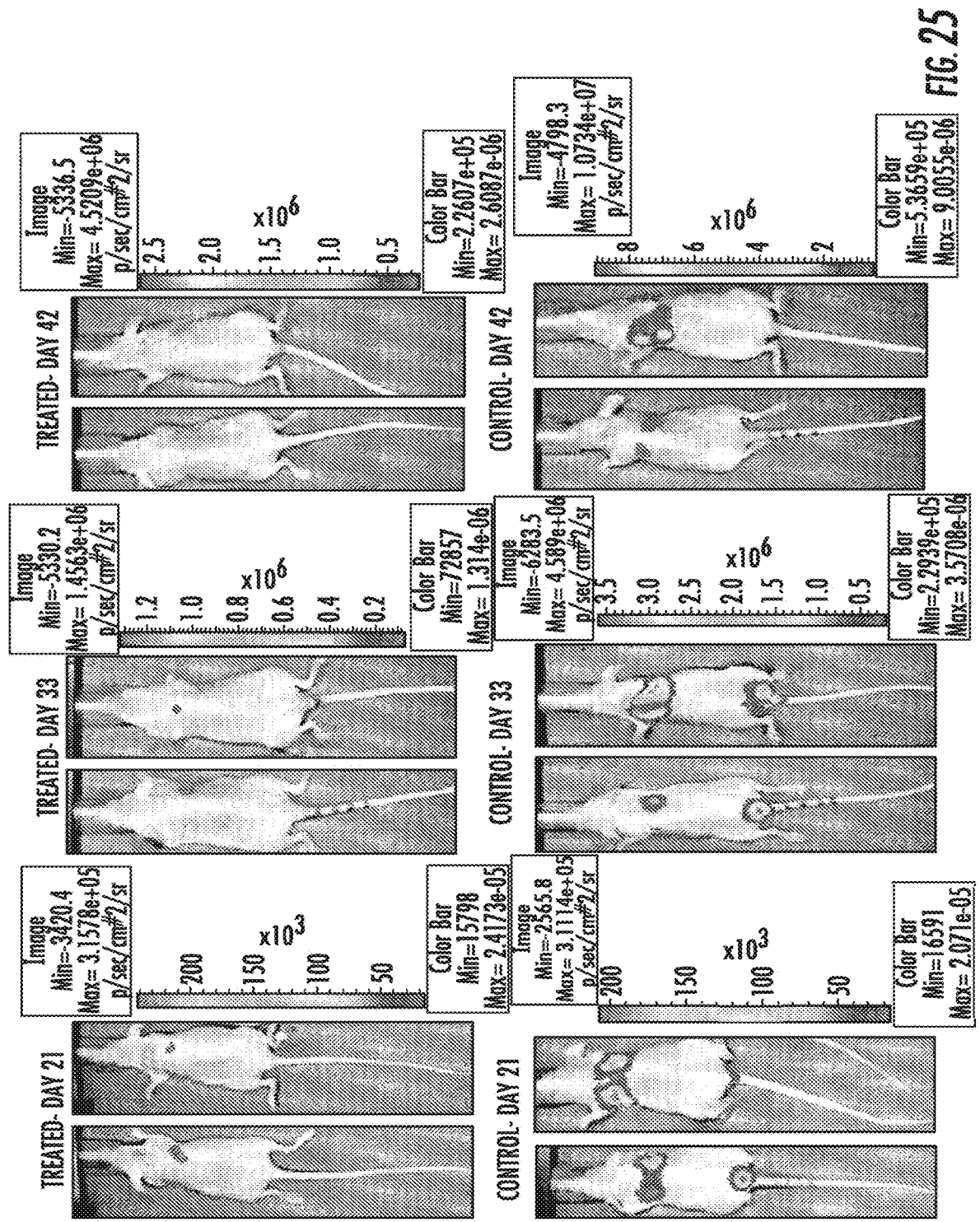
Figure 26A:
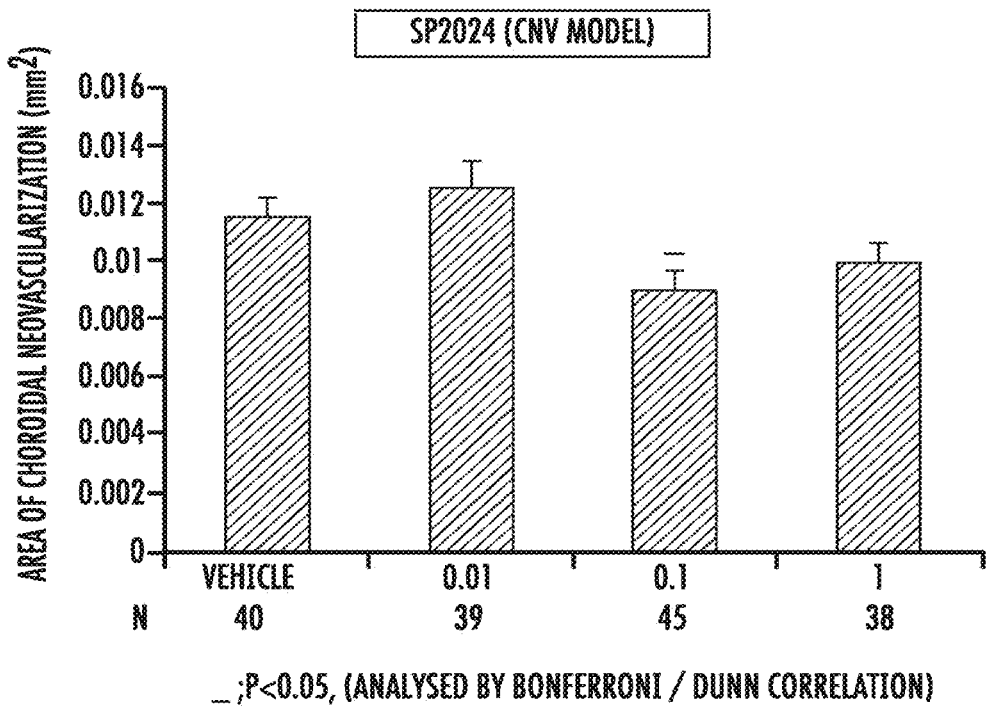
Figure 26B:
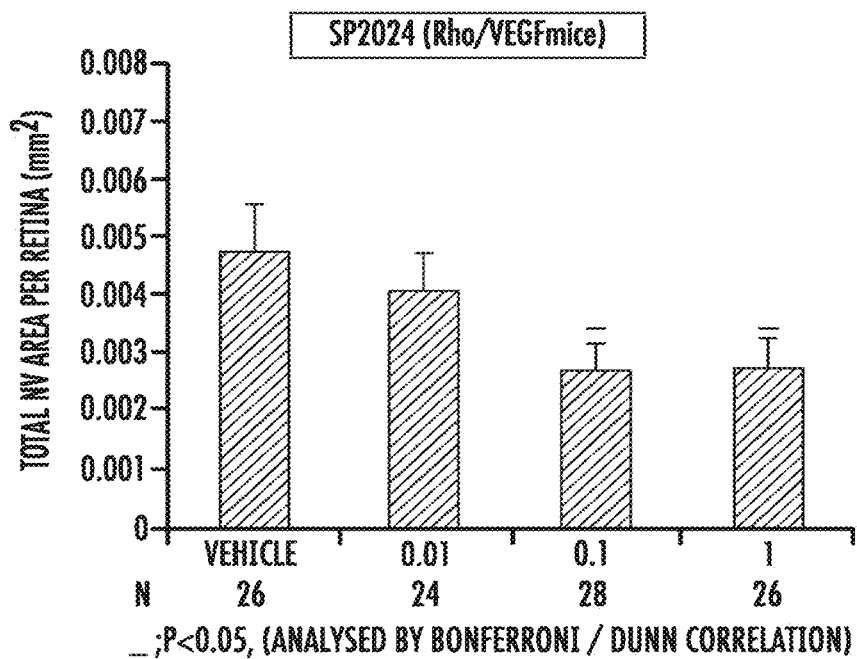
Figure 27A:
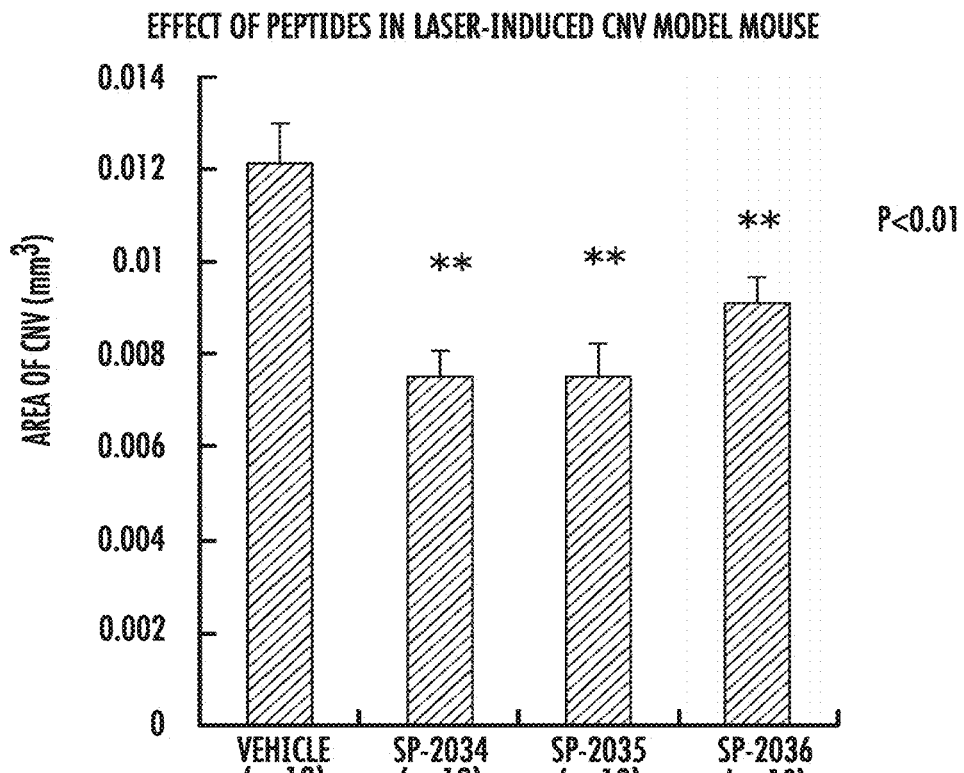
Figure 27B:
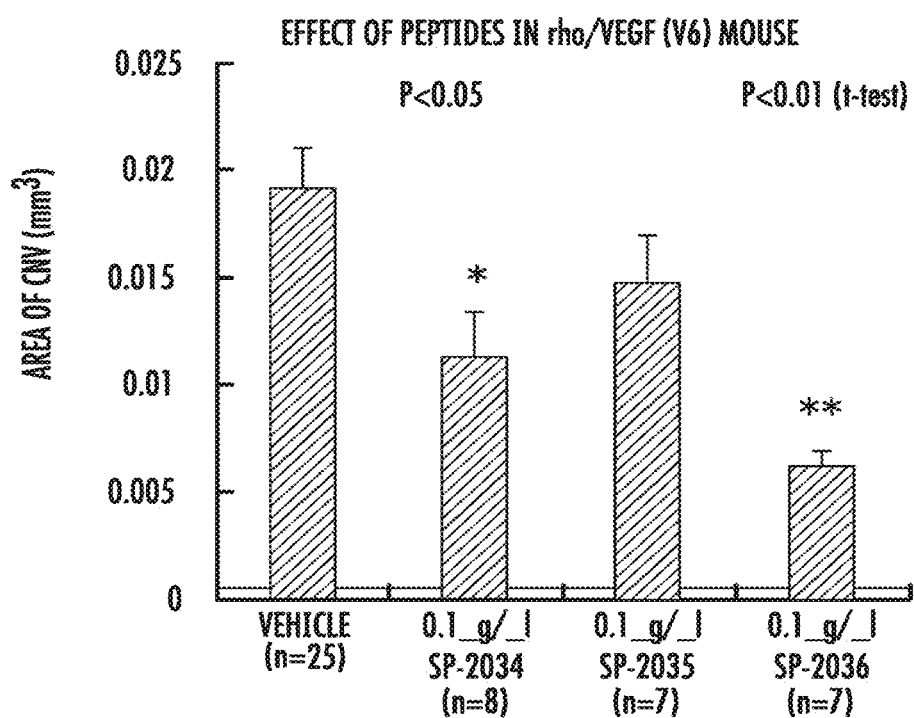

FIGS. 14A and 14B illustrate the inhibitory activity of the N-terminal deletion peptides in an adhesion assay (Panel A) and in a migration assay (Panel B);

FIGS. 15A-15D show the amino acid sequences of the peptides truncated from both the N-terminal and C-terminal ends (SP2012 is SEQ ID No: 3, SP2011 is SEQ ID No: 30, SP2010 is SEQ ID No: 29, SP2009 is SEQ ID No: 31, SP2020 is SEQ ID No. 35, and SP2021 is SEQ ID No: 32) (Panel A), adhesion assays with these peptides (Panel B), migration assays (Panel C), and proliferation assays (Panel D);

FIGS. 16A and 16B demonstrate adhesion assays (Panel A) and migration assays (Panel B) with the peptides truncated from both the N-terminal and C-terminal ends;

FIG. 17 illustrates a tube formation assay with some of the N-terminal deletion peptides and some of the peptides truncated on both ends;

FIGS. 18A and 18B show an adhesion assay (Panel A) and a migration assay (Panel B) with some of the full length peptides with other substitutions (SP2024, SP2034-SP2036; SEQ ID No:11, SEQ ID No:15-17);

FIGS. 19A and 19B demonstrate a proliferation assay (Panel A) and an adhesion assay (Panel B) with some of the full length peptides with other substitutions (SP2024, SP2034-SP2036; SEQ ID No:11, SEQ ID No:15-17);

FIGS. 20A-20E illustrate a tube formation assay with many of the peptides in the study;

FIGS. 21A-21E show the inhibitory activity of peptides SP2012 (SEQ ID No:3) and SP2024 (SEQ ID No:11) in an adhesion assay (Panel A) and migration assay (Panel C) on lymphatic endothelial cells, in an adhesion assay (Panel B) and migration assay (Panel D) on microvascular cells, and in a migration assay on breast cancer cells MDA-MB-231 (Panel E);

FIGS. 22A and 22B demonstrate the inhibitory activity of SP2024 (SEQ ID No:11) on breast cancer cells MDA-MB-231 using an adhesion assay (Panel A) and a migration assay (Panel B);

FIGS. 23A and 23B illustrate the suppression of tumor growth by SP2000 (SEQ ID No:19) and SP2012 (SEQ ID No:3) (Panel A) and the quantification of microvascular density (Panel B);

FIGS. 24A-24C show the inhibition activity of SP2024 (SEQ ID No:11) on tumor growth (Panel A), relative vascular volume (Panel B), and tumor permeability (Panel C);

FIG. 25 shows the inhibition of metastasis by SP2024 in an experimental metastasis model of breast cancer;

FIGS. 26A and 26B demonstrate the results from the injection of SP2024 (SEQ ID No:11) into a mouse eye by assaying the area of choroidal neovascularization (Panel A) and the area of retinal neovascularization (Panel B); and FIGS. 27A and 27B illustrate the results from injection of SP2034, SP2035, and SP2036 (SEQ ID Nos:15-17) into a mouse eye by assaying laser-induced choroidal neovascularization (Panel A) and the area of retinal neovascularization in the Rho/VEGF model (Panel B);

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Mimetic Peptides Derived from Collagen Type IV

Peptides generally offer many advantages over other types of therapies for certain diseases in that they are non-immunogenic, less toxic because they bind to their targets with high specificity, and are inexpensive to produce (e.g., International Publication WO 2008/085828 and International Publication WO 2007/033215, each which is incorporated herein by reference in its entirety). The presently disclosed peptides exhibit anti-angiogenic, anti-vascular permeability, anti-tumorigenesis and/or anti-lymphangiogenic properties, which could lead to an increase in overall survival in certain diseases. For example, the peptides may benefit cancer patients and may help treat ocular proliferative diseases, such as age-related macular degeneration. In general, the presently disclosed peptides are characterized by having the motif comprising the amino acid sequence LRRFSTXPXXXXNINNVXNF (SEQ ID No:1).

A. Representative Embodiments

In one embodiment, the peptide comprises the motif LRRFSTXPXXXXNINNVXNF (SEQ ID No: 1), X is any amino acid and the peptide does not comprise LRRF-STMPFMFCNINNVCNF (SEQ ID No:19), a previously disclosed peptide (Popel A. S. and Karagiannis E. D. "Peptide Inhibitors or Modifiers of Angiogenesis and Uses Thereof," PCT/WO/2008/085828; Rosca et al., 2011). X may be a natural or non-natural amino acid.

The nomenclature used herein is three-fold. First, all peptides begin with the letters SP; the peptide series is denoted by the first number and the last three numbers denote the particular peptide in the series. Thus, the presently disclosed series of peptides is labeled SP2XXX, with pentastatin 1, the parent, being labeled SP2000 (SEQ ID No:19).

The presently disclosed peptide series labeled SP2XXX were tested in angiogenesis and lymphangiogenesis assays in vitro. More particularly, proliferation, adhesion, migration, and tube formation assays were performed on endothelial, e.g., Human Umbilical Vein Endothelial Cells (HU-VECs), and other cells in vitro. Selected peptides were also tested in vivo in tumor xenograft and ocular assays. Representative embodiments of the peptide series are shown in Table 1 and are discussed in more detail below.

TABLE 1

Representative Presently Disclosed Peptides

| SEQ ID No: 3  | LRRFSTMPF M F Abu NINNV Abu NF         | SP2012 |
|---|---|---|
| SEQ ID No: 4  | LRRFSTMPA M F Abu NINNV Abu NF         | SP2015 |
| SEQ ID No: 5  | LRRFSTMPF A F Abu NINNV Abu NF         | SP2016 |
| SEQ ID No: 6  | LRRFSTMPF M A Abu NINNV Abu NF         | SP2017 |
| SEQ ID No: 7  | LRRFSTMPF Nle F Abu NINNV Abu NF       | SP2018 |
| SEQ ID No: 8  | LRRFSTMPF M 4-ClPhe Abu NINNV Abu NF   | SP2019 |
| SEQ ID No: 2  | LRRFSTMPF M F G NINNV G NF             | SP2002 |
| SEQ ID No: 9  | LRRFSTMPF M F S NINNV S NF             | SP2022 |
| SEQ ID No: 10 | LRRFSTMPF M F A NINNV A NF             | SP2023 |
| SEQ ID No: 14 | LRRFSTMPF M F V NINNV V NF             | SP2027 |
| SEQ ID No: 12 | LRRFSTMPF M F T NINNV T NF             | SP2025 |
| SEQ ID No: 13 | LRRFSTMPF M F AllyGly NINNVAllyGly NF  | SP2026 |
| SEQ ID No: 11 | LRRFSTMPF M F I NINNV I NF             | SP2024 |
| SEQ ID No: 15 | LRRFSTMPF dA F I NINNV I NF            | SP2034 |
| SEQ ID No: 16 | LRRFSTAPF M F I NINNV I NF             | SP2035 |
| SEQ ID No: 17 | LRRFSTAPF A F I NINNV I NF             | SP2036 |

For the presently disclosed subject matter, the peptides have several X residues that may be any amino acid, whether natural or non-natural (X7, X9, X10, X11, X12, and X18). By natural amino acids, it is meant those amino acids that occur in nature. By non-natural amino acids, it is meant amino acids that do not occur in nature but that can be incorporated into a polypeptide chain. Non-natural amino acids include, but are not limited to 2-aminobutyric acid (Abu), norleucine (Nle), 4-chloro phenylalanine (4-ClPhe), allylglycine (AllyGly) and other non-natural amino acids such as those detailed in Ma (2003). Amino acid analogs that are known in the art may be employed in the present invention.

A "peptide" or "protein" comprises a string of at least three amino acids linked together by peptide bonds. The terms "protein" and "peptide" may be used interchangeably. Peptide may refer to an individual peptide or a collection of peptides. Also, one or more of the amino acids in a presently disclosed peptide may be modified, for example, by the addition of a chemical entity such as a carbohydrate group, a phosphate group, a farnesyl group, an isofarnesyl group, a fatty acid group, a linker for conjugation, functionalization, or other modification, and the like. In some embodiments, the modifications of the peptide lead to a more stable peptide (e.g., greater half-life in vivo). These modifications may include cyclization of the peptide, the incorporation of D-amino acids, and the like. None of the modifications should substantially interfere with the desired biological activity of the peptide.

By "Collagen IV derived peptide" it is meant a peptide comprising a C-N-X(3)-V-C or P-F-X(2)-C or LX(2)FX(3) PFX(2)CNX(4)CNX collagen motif. If desired, the peptide includes at least about 5, 10, 20, 30, 40, 50 or more amino acids that flank the carboxy or amino terminus of the motif in the naturally occurring amino acid sequence. Type IV collagen derived peptides include, for example, pentastatin-1, tumstatin, and targeting RGD. By "alteration" is meant a change in the sequence or in a modification (e.g., a post-translational modification) of a gene or polypeptide relative to an endogenous wild-type reference sequence.

By an "isolated peptide" is meant a peptide of the invention that has been separated from components that naturally accompany it. Typically, the peptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a presently disclosed peptide of the invention. An isolated peptide may be obtained, for example, by extraction from a natural source, by expression of a recombinant nucleic acid encoding such a peptide; or by chemically synthesizing the protein. Purity can be measured by any appropriate method, for example, column chromatography, polyacrylamide gel electrophoresis, or by HPLC analysis.

By "substantially identical" is meant a peptide, a polypeptide or nucleic acid molecule exhibiting at least 50% identity to a reference amino acid sequence (for example, any one of the amino acid sequences described herein) or nucleic acid sequence. Preferably, such a sequence is at least 60%, more preferably 80% or 85%, and even more preferably 90%, 95% or even 99% identical at the amino acid level or nucleic acid to the sequence used for comparison.

Further, the presently disclosed peptides can be modified to make them less susceptible to proteolysis. For example, they can be truncated to the minimal potent sequence. Such truncation is important to limit binding to other receptors that would dilute the effective concentration, as well as lead to unexpected side effects. Such truncation also opens up the possibility to create a single multimodal peptide out of multiple short peptides, each of which targets angiogenesis, lymphangiogenesis and tumorigenesis by a different mechanism. Multimodal treatment is very important to reduce the incidence of drug resistance, because it is less likely that the tumor will be able to mount a successful resistance when attacked simultaneously from multiple fronts.

In addition, the presently disclosed peptides with different sequences can be used together in one composition or method. There may be compositions or methods where multiple types of the presently disclosed peptides allow better prevention or reduction of angiogenesis, vascular permeability, tumorigenesis or lymphangiogenesis. Therefore, instead of a composition with a single multimodal peptide, a composition may be comprised of multiple types of isolated peptides that are not covalently bound together.

Further, the presently disclosed peptides are all tri-fluoro acetate (TFA) salts. For use in humans, however, the TFA salts can be modified to acetate salts or other pharmaceutically acceptable salts.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al., "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Further, one or more of the presently disclosed peptides can be incorporated into nano or microparticles, such as those disclosed in U.S. patent application Ser. No. 13/272,042, to Green et al. for "Peptide/Particle Delivery Systems," filed Oct. 12, 2011, and International PCT Patent Application Publication No. WO/2010/132879 to Green et al. for "Multicomponent Degradable Cationic Polymers," filed May 17, 2010, both of which are commonly owned and incorporated herein by reference in their entirety.

In addition, it is possible to increase the half-lives of the peptides by conjugating the peptides to certain compounds. For example, it is possible to conjugate the peptides to catalytic antibodies to increase their half-lives.

In an embodiment, the presently disclosed subject matter provides an isolated peptide comprising the amino acid sequence LRRFSTXP INNVXNF (SEQ ID No:1), wherein X at position 7 is M, A, or G; X at position 9 is F, A, Y, or G; X at position 10 is M, A, G, dA, or Nle; X at position 11 is F, A, Y, G, or 4-ClPhe; X at position 12 and position 18 are Abu, G, S, A, V, T, I, L or AllyGly; and wherein the peptide does not comprise LRRFSTMPFMFCNINNVCNF (SEQ ID No:19).

In a further embodiment, the presently disclosed subject matter provides an isolated peptide comprising at least one of the following amino acid sequences:

LRRFSTMPFMFAbuNINNVAbuNF; (SEQ ID No: 3)

LRRFSTMPAMFAbuNINNVAbuNF; (SEQ ID No: 4)

LRRFSTMPFAFAbuNINNVAbu NF; (SEQ ID No: 5)

LRRFSTMPFMAAbuNINNVAbuNF; (SEQ ID No: 6)

LRRFSTMPFNleFAbuNINNVAbuNF; (SEQ ID No: 7)

LRRFSTMPFM4-ClPheAbuNINNVAbuNF; (SEQ ID No: 8)

LRRFSTMPFMFGNINNVGNF; (SEQ ID No: 2)

LRRFSTMPFMFSNINNVSNF; (SEQ ID No: 9)

LRRFSTMPFMFANINNVANF; (SEQ ID No: 10)

LRRFSTMPFMFVNINNVVNF; (SEQ ID No: 14)

LRRFSTMPFMFTNINNVTNF; (SEQ ID No: 12)

LRRFSTMPFMFAllyGlyNINNVAllyGlyNF; (SEQ ID No: 13)

LRRFSTMPFMFININNVINF; (SEQ ID No: 11)

LRRFSTMPFdAFININNVINF; (SEQ ID No: 15)

LRRFSTAPFMFININNVINF; (SEQ ID No: 16)
and

LRRFSTAPFAFININNVINF. (SEQ ID No: 17)

In another embodiment, the presently disclosed subject matter provides compositions and kits comprising a pharmaceutically acceptable carrier and an effective amount of at least one of the peptide sequences disclosed herein. The amount of peptide can vary widely, but generally the amount is sufficient to perform at least one method of the invention.

As used herein, "pharmaceutically acceptable carrier" is intended to include, but is not limited to, water, saline, dextrose solutions, human serum albumin, liposomes, hydrogels, microparticles and nanoparticles. The use of such media and agents for pharmaceutically active compositions is well known in the art, and thus further examples and methods of incorporating each into compositions at effective levels need not be discussed here. Such compositions also can include coatings, antibacterial and/or fungal agents, and any other ingredient that is biologically tolerable.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

In general, a presently disclosed kit contains some or all of the components, reagents, supplies, and the like to practice a method according to the presently disclosed subject matter. In a kit comprising an isolated peptide according to the presently disclosed subject matter, the kit typically comprises an effective amount of peptide to prevent, delay, reduce, or treat a disease related to angiogenesis and/or lymphangiogenesis. In one embodiment, a kit comprises at least one container (e.g. a vial, tube, or ampoule) comprising an isolated peptide of the presently disclosed subject matter. Typically, the isolated peptide or peptides will be supplied in one or more container, each container containing an effective amount of isolated peptide to allow a change in angiogenesis and/or lymphangiogenesis to occur.

B. General Terms

For clarity, other general terms are described below. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

"Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences which differ by such conservative substitutions are said to have sequence similarity. Approaches for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers and Miller, *Computer Applic. Biol. Sci.*, 4: 11-17, 1988, for example, as implemented in the program PC/GENE (Intelligenetics, Mountain View, Calif., USA).

"Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "homologous" in their various grammatical forms in the context of polynucleotides means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 85%, 90%, and even more preferably at least 95%.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 5, 10, or 15 amino acids, preferably at least about 20 amino acids, more preferably at least about 25 amino acids, and even more preferably about 35 amino acids, about 50 amino acids, about 100 amino acids, or about 150 amino acids.

II. Methods of Treating Angiogenesis- and Lymphangiogenesis-Dependent Diseases

A. Representative Embodiments

In some embodiments, the presently disclosed peptides exhibit anti-angiogenic anti-lymphangiogenic, anti-tumorigenic, and/or anti-vascular permeable properties. Angiogenesis refers to the growth of new blood vessels originating from existing blood vessels. Lymphangiogenesis refers to the formation of lymphatic vessels from pre-existing lymphatic vessels, in a method believed to be similar to blood vessel development or angiogenesis. Tumorigenesis refers to the formation of a tumor. Vascular permeability refers to the property of blood capillary walls that allows for the selective exchange of substances.

In some embodiments, the presently disclosed subject matter provides a method of inhibiting angiogenesis and/or lymphangiogenesis involving a cell. The method comprises contacting a cell with a presently disclosed isolated peptide in an amount sufficient to inhibit angiogenesis and/or lymphangiogenesis of the cell. The contacting of the cell may result in an inhibition of adhesion, migration, proliferation, and/or tube formation involving the cell. In a particular embodiment, the cell is an endothelial cell.

The method of the presently disclosed subject matter can be practiced in vivo as either a therapeutic method of treating a disease or disorder involving angiogenesis or lymphangiogenesis or as a prophylactic method to prevent angiogenesis or lymphangiogenesis. Likewise, the method can be practiced in vitro as a research tool to study the effects of angiogenesis or lymphangiogenesis on a cell. The method also can be practiced ex vivo for therapeutic or research purposes.

"Contacting" means any action that results in at least one isolated peptide of the presently disclosed subject matter physically contacting at least one cell. It thus may comprise exposing the cell(s) to the isolated peptide in an amount sufficient to result in contact of at least one isolated peptide with at least one cell. The method can be practiced in vitro or ex vivo by introducing, and preferably mixing, the isolated peptide and cells in a controlled environment, such as a culture dish or tube. The method can be practiced in vivo, in which case contacting means exposing at least one cell in a subject to at least one isolated peptide of the presently disclosed subject matter, such as administering the isolated peptide to a subject via any suitable route. According to the presently disclosed subject matter, contacting may comprise introducing, exposing, and the like, the isolated peptide at a site distant to the cells to be contacted, and allowing the bodily functions of the subject, or natural (e.g., diffusion) or man-induced (e.g., swirling) movements of fluids to result in contact of the isolated peptide and cell(s).

In some embodiments, the presently disclosed subject matter provides a method for treating a subject suffering from a disease related to angiogenesis, lymphangiogenesis, tumorigenesis, and/or vascular permeability or to prevent or delay a subject from developing a disease related to angiogenesis, lymphangiogenesis, tumorigenesis, and/or vascular permeability. The method comprises administering to the subject a presently disclosed isolated peptide in an amount sufficient to treat, delay, or prevent the disease in the subject. Representative diseases include those diseases that are angiogenesis-, lymphangiogenesis-, tumorigenesis-, and or vascular permeability-dependent. Accordingly, in some embodiments, the disease may be a cancer, such as cancer of the breast, lung, glioblastoma, renal cell, hepatic cell, head, neck, or any other cancer that relies on angiogenesis or lymphangiogenesis to occur or spread. In one embodiment, the method treats a primary tumor. In another embodiment, the method treats an established metastasized tumor. The method may inhibit angiogenesis and/or lymphangiogenesis in or surrounding a tumor. The method also may inhibit dissemination of tumor cells through the blood and/or lymphatic vasculature. Further, the method may inhibit the establishment of metastasis or inhibit further metastasis of the cancer.

In other embodiments, the disease may be related to ocular angiogenesis, such as age-related macular degeneration, macular edema, neovascular glaucoma, proliferative diabetic retinopathy, or retinopathy of prematurity. In vivo experiments described herein below illustrate the effect of selected isolated peptides of the presently disclosed subject matter in a mouse model.

In certain embodiments, the presently disclosed subject matter provides for the use of the isolated peptides in the treatment of a disease associated with angiogenesis, lymphangiogenesis, tumorigenesis, and/or vascular permeability. The use is in particular for in vivo therapeutic or prophylactic methods of inhibiting angiogenesis, lymphangiogenesis, tumorigenesis, and/or vascular permeability. Certain embodiments provide for the use of the isolated peptides in the preparation of compositions for medical use, such as pharmaceutical or therapeutic compositions. In general, use of the isolated peptides is in combining them with other substances to make medicinal compositions.

The peptides according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

B. General Terms

By "disease" is meant any condition, dysfunction or disorder that damages or interferes with the normal function of a cell, tissue, or organ.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

By "blood vessel formation" is meant the dynamic process that includes one or more steps of blood vessel development and/or maturation, such as angiogenesis, vasculogenesis, formation of an immature blood vessel network, blood vessel remodeling, blood vessel stabilization, blood vessel maturation, blood vessel differentiation, or establishment of a functional blood vessel network.

By "vasculogenesis" is meant the development of new blood vessels originating from stem cells, angioblasts, or other precursor cells.

By "blood vessel stability" is meant the maintenance of a blood vessel network.

By "neoplasia" is meant a disease that is caused by or results in inappropriately high levels of cell division, inappropriately low levels of apoptosis, or both. Solid tumors, hematological disorders, and cancers are examples of neoplasias.

A "tumor," as used herein, refers to all neoplastic cell growth and proliferation, whether malignant or benign, and all precancerous and cancerous cells and tissues.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduce" is meant a decrease in a parameter (e.g., blood vessel formation) as detected by standard art known methods, such as those described herein. As used herein, reduce includes a 10% change, preferably a 25% change, more preferably a 40% change, and even more preferably a 50% or greater change.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000). To aid in bioavailability, the compounds of the disclosure may be delivered in a nano- or micro-particles.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Cysteine Substitutions in the Full Peptide

SP2000 (SEQ ID No:19), which has the sequence LRRF-STMPFMFCNINNVCNF, was the original peptide identified by a previously disclosed Bioinformatics approach (Karagiannis and Popel, 2008). In this Example, the cysteines in SP2000 (SEQ ID No:19) were substituted to determine if the two cysteines are essential for activity (Table 2).

For the growth of cells in cell culture, human umbilical vein endothelial cells (HUVEC), microvascular endothelial cells (MEC), and lymphatic endothelial cells (LEC) were purchased from Lonza and maintained according to the manufacturer's recommendation using Endothelial Basal Media (EBM-2) supplemented with the Bullet Kit (EGM-2, Lonza). The MEC and LEC were propagated in Microvascular Endothelial Cell Growth Medium-2 (EGM-2MV, Lonza). Breast cancer cells, MDA-MB-231 were supplied by Dr. Zaver Bhujwalla (JHMI, Radiology and Oncology). The cells were propagated in RPMI-1640 medium (Gibco, Carlsbad, Calif.) supplemented with 10% FBS and antibiotics (1% penicillin/streptomycin). Cells were maintained under standard conditions of 37° C. and 5% $CO_2$ and the passage numbers of all used cells were between 2 and 7.

Peptides were synthesized using solid-phase synthesis and were supplied as TFA salts with an amidated C-terminus by two vendors (New England Peptide, Gardner, Mass. and American Peptide Company, Sunnyvale, Calif.). The purity of the peptides was >95% and the suppliers provided product characterization (MALDI-TOF and HPLC traces) as proof of MW and purity accuracy. Peptides were solubilized in 5% DMSO and water due to their hydrophobic profile. The pH of solubilized peptides was checked and found to be around pH 7. For all experiments the DMSO % was maintained at non-toxic threshold (determined by toxicity curves of DMSO on cells) with a final DMSO percentage (<0.2%) which was used as control in all experiments.

Several assays were used to test the peptides discussed in the Examples herein. A colorimetric based proliferation assay using WST-1 (Roche, 11644807001) proliferation reagent was carried out using HUVEC cells. 2000 cells/well were plated in 96-well plates and allowed to adhere overnight. On the following day, the media was exchanged with fully supplemented media containing peptides or equivalent DMSO vehicle for the controls. Three days later the media containing the peptides was replaced with serum-free EBM-2 media containing WST-1 reagent and the plates were incubated for four hours as per the manufacturer's recommendations. Changes in color, due to the formazan dye resulted from the cleavage of the tetrazolium salt WST-1 by the mitochondrial succinate-tetrazolium reductase, were read on a Victor V fluorescence plate reader (Perkin Elmer, MA) by measuring the absorbance at 450 nm. Dose response curves of percent live cells (in comparison to untreated cells but incubated in complete media with 0.2% DMSO) were created. Assays were performed in at least two independent replicates and each replicate was performed using three experimental triplicates.

The inhibitory potential of the peptides was measured using a real time migration assay system based on electrical impedance (RT-CIM, ACEA Biosciences, CA). CIM 16 well plates (Roche, 05665817001) are composed of a top and bottom chamber separated by a microporous (8 µm) polycarbonate membrane. The membrane was coated with fibronectin (20 µg/mL), and 45,000 cells/well in serum free media with or without peptides were added to the top compartment. Media with chemoattractant (i.e., fully supplemented EBM-2) was added to the bottom compartment of the chamber and the plate was incubated at 37° C. for 20 hours. The sensors integrated on the bottom side of the membrane monitor and continuously record changes in impedance as the cells move through the membrane. The RT-CIM technology allows for easy quantification of cell migration by monitoring the cell index derived from the measured impedances. Assays were performed in at least two independent replicates and each replicate was performed using two experimental duplicates.

Breast cancer cells MDA-MB-231 are not suitable for the RT-CIM type experiments due to their thin elongated phenotype, thus the inhibition of migration was investigated using a wound healing type assay. This assay was performed using the Oris Pro Migration assay (Platypus Technologies, CMA 1.101). Briefly, 20,000-25,000 cells/well in full media were added to the 96 well plate containing stoppers to block migration of cells to the center region of the wells. Cells were allowed to adhere for 4 hours, after which the stoppers were removed. Cells were washed one time with PBS and fully supplemented media, with or without compound, was added to the wells. After 18 hours, cells were stained with calcein AM (0.5 µg/mL) (Invitrogen, Calif.) and the cells that migrated to the center of the well were quantified by fluorescence intensity measured using a Victor V plate reader (Perkin Elmer) and also imaged using a Leica or Nikon microscope. The detection of the cells that migrated into the previously restricted region was possible due to the addition of a detection mask at the bottom of the plate, which obstructed from measurement cells that did not migrate.

Similar to the migration assays, the inhibition activity of the peptide in cellular adhesion was assessed using the RT-CIM technology. In this case, 25,000 cells/well were plated in 16 wells E-plates (Roche, Basel Switzerland) in the presence or absence of the peptide. The adhesion was monitored over time (3 hours) by measuring changes in the electrical impedance, which is a direct measure of the cells adhering on the electrodes. For the most active peptide, $IC_{50}$ values were calculated from dose response curves. Assays were performed in at least two independent replicates and each replicate was performed using two experimental duplicates.

The compounds also were tested for their ability to inhibit tube formation, a process critical in angiogenesis. Endothelial cells spontaneously form a network of tubes when plated on extracts of extracellular matrix. This in vitro assay combines aspects of adhesion and migration and it is routinely used in angiogenesis research (Oliveira-Ferrer et al., 2008). The ability to inhibit tube formation is a comprehensive assessment of the anti-angiogenic potential. The protocol was described by Arnaoutova et al. (2009) and it consists of plating HUVEC on top of basement membrane extract and after incubation at 37° C. the cells naturally rearrange themselves in a network of tubes. Thus, 50 µL/well of Matrigel (BD Biosciences, San Jose, Calif.) was plated in a cold 96 well plate and incubated at 37° C. for 30 min for polymerization. 15,000 cells/well were added to the top of the gel and incubated in complete media in the presence or absence of peptide for 19 hours. Images were captured using the CCD Sensicam mounted on a Nikon microscope (Eclipse T-100). Assays were performed in at least two independent replicates and each replicate was performed using three experimental replicates and one image of a randomly chosen field was acquired per well.

For primary tumor inhibition studies, $1-2\times10^6$ tumor cells were injected into 4-6 wk old female SCID mice. After the tumors reached a size of 100 mm³ the animals were randomized into groups of 10 animals each. The animals were treated with vehicle, SP2012, SP2000, or SP2024. The peptides were administered subcutaneously daily. Dosing was continued for 3 or 4 weeks and tumor sizes were measured every 3 days using calipers. The tumor volume was estimated using the formula $V=a^2b/2$ where a and b are the smaller and larger diameters.

The tail vein assay of cancer metastasis protocol from Current Protocols of Cell Biology was used to measure the effect of SP2024 on lung metastasis (Elkin and Vlodavsky, 2001). 1 mL of $5\times10^5$ cells/mL luciferase-transfected MDA-MB-231-luc-D3H2LN (Caliper Biosciences) cell suspension was slowly injected into nude mice (nude mice are easier to image because of their lack of fur). Two hours before cell inoculation vehicle or 10 mg/kg SP2024 were administered subcutaneously on a daily basis. Bioluminescence to detect metastasis was measured by IVIS imaging (Caliper Biosciences) via IP injection of 150 mg/kg D-luciferin.

MRI of vascular volume and permeability surface-area product (PSP) were determined as follows. Mice with volume-matched tumors were treated with SP2024 or vehicle and imaged 24 h post treatment. The mice were anesthetized and the tail vein was catheterized before placing the animal in the spectrometer. All imaging studies were performed on a 4.7 T Bruker Avance spectrometer, as previously described (Raman et al., 2006; Bhujwalla et al., 2001) using a home-built solenoid coil placed around the tumor. Briefly, multi-slice relaxation rate (1/T1) maps were obtained by a saturation recovery method combined with fast T1 SNAPSHOT-FLASH imaging (flip angle of 10°, echo time of 2 ms). First, an Mo map with a recovery delay of 7 s was acquired following which images of 4 slices (1 mm thick), acquired with an in-plane spatial resolution of 125 mm (128×128 matrix, 16 mm field of view, 8 averages), were obtained for three relaxation delays (100 ms, 500 ms and 1 s). These T1 recovery maps were obtained before i.v. administration of 0.2 ml of 60 mg/mL albumin-GdDTPA in saline (dose of 500 mg/kg) and repeated six times starting 3 min after i.v. injection of albumin-GdDTPA. Albumin-GdDTPA was synthesized based on the method of Ogan et al. (1988). Relaxation maps were reconstructed from data sets for three different relaxation times and the Mo dataset on a pixel-by-pixel basis. At the end of the imaging studies, the animals were sacrificed, 0.5 ml of blood was withdrawn from the inferior vena cava or tail vein, the T1 of blood was measured, and tumors were excised and fixed in 10% buffered formalin for sectioning and staining. Vascular volume and PSP maps were generated from the ratio of D(1/T1) values in the images to that of blood. The slope of D(1/T1) ratios versus time in each pixel was used to compute PSP, and the intercept of the line at zero time was used to compute vascular volume, corrected for permeability of the vessels. The detectable areas of vascular volume and permeability as well as absolute values of vascular volume and permeability were analyzed. Three-dimensional volume data were processed with an operator-independent computer program that enabled selection, mapping and display of the regions. Volume fractions of the regions were determined using the histogram analysis of the volume data. Values of vascular volume and PSP were computed for every voxel in the tumor with a routine written using Interactive Data Language (IDL, Research Systems, Boulder, Colo.). Statistical significance ($p<0.05$) within each experiment using the independent replicates was assessed using standard statistical assessments such as Student's t-test and ANOVA accompanied by Dunnett's test if different sets of data were compared to one group.

The original peptide, SP2000 (SEQ ID No:19), was substituted at the two Cysteine positions to determine what effect the elimination of the Cysteine residues would have on activity (Table 2). FIG. 1 shows the results of a proliferation assay. All of the peptides with the Cysteines substituted inhibited the proliferation of HUVECs with the most potent activity shown by SP2024 (SEQ ID No:11) (IC$_{50}$ value of 1.29 μM).

The inhibition activity of the substituted peptides in adhesion of HUVECs also was assessed and the results are shown in FIG. 2. All of the peptides showed inhibition of adhesion when compared to the control.

Migration assays were consistent with the adhesion assays and demonstrated inhibition of migration of HUVECs for all the peptides when compared to the control at a peptide concentration of 50 μM (FIG. 3).

FIG. 4 illustrates inhibition of migration with peptide SP2012 (SEQ ID No:3). Panel A shows a wound healing assay with the migration of cells in the presence or absence of peptide under constant concentration of chemoattractant (complete media). The peptide concentration was varied at 0.5 μM, 5 μM, and 50 μM. Migration of MDA-MB-231 cells into the restricted area was quantified after 17 hours of incubation (Panel B). The 50 μM and 5 μM treatments were statistically significant versus the control ($p<0.05$). Error bars depict SEM.

FIG. 5 illustrates another experiment showing the inhibition of activity in adhesion at 50 μM (Panel A) and the inhibition of activity in migration at 50 μM (Panel B) and 5 μM (Panel C). The results again show that all the peptides exhibit inhibition of adhesion and migration of HUVECs. The inhibitory activity in the adhesion assay was quite similar to that of the parent compound (SP2012; SEQ ID No:3), resulting in almost complete inhibition at 50 μM. However, the activity in migration was significantly increased from 60% in the parent compound (SP2012; SEQ ID No:3) to >90% in the modified peptides. Thus the activity was investigated at 5 μM, a much lower concentration, and it was observed that SP2022 (SEQ ID No:9) showed similar activity to the parent compound (SP2012; SEQ ID No:3) while the other compounds SP2023 through SP2027 (SEQ ID Nos:10-14) showed much greater activity. The * indicates statistical difference ($p<0.05$) in activity in comparison to SP2012. The y-axis range is reduced to 0-20% for Panel A and 0-50% for Panel B.

The peptides with the substituted cysteines were further tested using the tube formation assay (FIG. 6A and FIG. 6B). The control contained 15,000 HUVECs/well plated in complete media. Each well contained peptide plated in complete media all plated on matrigel (50 μL/well). The results showed that all of the Cysteine-substituted peptides had inhibitory activity on tube formation.

TABLE 2

Summary of Cysteine Substitutions in the Full Peptide

| Peptide No./ SEQ ID No. | Peptide sequence | Proliferation Inhibition (IC50 in uM) | Migration Inhibition (50 uM) | Adhesion Inhibition (100 uM) | Tube formation Inhibition (100u M) | MDA-MB-231 xenograft inhibition |
|---|---|---|---|---|---|---|
| SP2000/ 19 | LRRFSTMPFMFCN INNVCN | 15.5 | 80% | 95% | Complete | Active |
| SP2012/ 3 | LRRFSTMPFMFAb uNINNVAbuN | 22 | 68% (50 uM) 0% (5 uM) | 93.14% | Complete (10 uM) | Active |
| SP2002/ 2 | LRRFSTMPFMFGN INNVGNF | 31.4 | 87.9% (50 uM) | | Complete | |
| SP2022/ 9 | LRRFSTMPFMFSNI NNVSNF | 16.9 | 8.95% (5 uM) | 96.49% | | |
| SP2023/ | LRRFSTMPFMFAN INNVANF | 2.47 | 31.18% (5 uM) | 96.29% | Complete | |
| SP2024/ 11 | LRRFSTMPFMFINI NNVINF | 1.29 | 37.73% (5 uM) | 94.45% | Complete | Active |
| SP2025/ 12 | LRRFSTMPFMFTN INNVTNF | 13.5 | 18.19% (5 uM) | 96.48% | Complete | |
| SP2026/ 13 | LRRFSTMPFMF(All yGly)NINNV(AllyGl y)NF | 8.23 | 11.43% (5 uM) | 96.61% | Complete | |

TABLE 2-continued

Summary of Cysteine Substitutions in the Full Peptide

| Peptide No./ SEQ ID No. | Peptide sequence | Proliferation Inhibition (IC50 in uM) | Migration Inhibition (50 uM) | Adhesion Inhibition (100 uM) | Tube formation Inhibition (100u M) | MDA-MB-231 xenograft inhibition |
|---|---|---|---|---|---|---|
| SP2027/ 14 | LRRFSTMPFMFVN INNVVNF | 6.04 | 27.02% (5 uM) | 96.75% | Complete | |

Example 2

Alanine and Other Substitutions in the Full Peptide

With the peptide SP2012 (SEQ ID No:3) as a reference, Alanine was used to substitute for other amino acids in the SP2012 (SEQ ID No:3) sequence (Table 3). These peptides all showed inhibition of proliferation (FIG. 7) and inhibition of adhesion at 50 μM of HUVECs (FIG. 8). The inhibition of migration at 50 μM was significantly greater for the peptides with Alanine substitutions compared to SP2012 (FIG. 9). One of the peptides, SP2015 (SEQ ID No:4), was tested in the HUVEC tube formation assay (FIG. 10). SP2015 (SEQ ID No:4) showed significant inhibition of tube formation.

(SP2029 (SEQ ID No:21) vs. SP2006 (SEQ ID No:18)). Substitution of Abu in SP2028 (SEQ ID No:20) by a Threonine (SP2032; SEQ ID No:22), resulted in a reduction in activity while its replacement by Isoleucine maintained the same level of activity (SP2033; SEQ ID No. 23) thus confirming that the nature of the amino acid residue at this position is important for the inhibition of proliferation.

FIG. 11 shows the ability of the C-terminal deletions peptides to inhibit adhesion and migration of endothelial cells. Panel A lists the amino acid sequences of the peptides used in this series of experiments. Panel B illustrates an adhesion experiment at 100 μM peptide concentration in which significant inhibition can be seen for peptide SP2006 (SEQ ID No:18). Panel C shows a migration experiment at a peptide concentration of 50 μM. Again, inhibition can be

TABLE 3

Summary of Alanine Substitutions in the Full Peptide

| Peptide No./ SEQ ID No. | Peptide sequence | Proliferation Inhibition (IC50 in uM) | Migration Inhibition (50 uM) | Adhesion Inhibition (100 uM) | Tube formation Inhibition (100 uM) |
|---|---|---|---|---|---|
| SP2015/ 4 | LRRFSTMPAMF(Abu)NI NNV(Abu)NF | 16.8 19.48 | 100% | 96% | Complete |
| SP2016/ 5 | LRRFSTMPFAF(Abu)NI NNV(Abu)NF | 11.3 2.82 | 99.6% | 96% | |
| SP2017/ 6 | LRRFSTMPFMA(Abu)NI NNV(Abu)NF | 9.63 32.9 | 100% | 95.5%% | |
| SP2018/ 7 | LRRFSTMPF(Nle)F(Abu) NINNV(Abu)NF | 18.2 9.14 | 100% | 90.9%% | |
| SP2019/ 8 | LRRFSTMPFM(4-ClPhe)(Abu)NINNV(Abu) NF | 15.9 18.5 | 98% | 95.9% | |

Example 3

C-Terminal Deletions

Tables 4 and 5 list the family of peptides that were generated by eliminating residues from the C-terminus of the parent peptide (SP2012; SEQ ID No:3). Truncations that eliminated the NINNV (SEQ ID No:36) sequence showed loss of inhibitory activity in proliferation of endothelial cells. Peptides that include representative residues from this critical sequence (i.e. SP2028 (SEQ ID No:20), SP2029 (SEQ ID No:21), SP2032 (SEQ ID No:22) and SP2033 (SEQ ID No:23)) demonstrated potent activity in inhibiting proliferation, even improved activity as compared to the parent compound. The substitution of Asparagine, a hydrophilic residue, by Valine, a hydrophobic amino acid led to loss in activity (SP2028 (SEQ ID No:20) vs. SP2006 (SEQ ID No: 18)). However, if in addition the Abu residue was replaced by Threonine, the new compound regained activity seen for SP2006 (SEQ ID No:18). Panel D shows the inhibition of adhesion for SP2006 (SEQ ID No:18) at a concentration of 50 μM.

FIG. 12 again illustrates the inhibitory activity of peptides generated by deletions from the C-terminus of SP2012 in HUVEC adhesion (Panel A) and migration assays (Panel B). The same four peptides that exhibited activity in the inhibition of proliferation were also very potent in inhibiting adhesion and migration, but did not display increased activity over the parent compound SP2012 (SEQ ID No:3). In the proliferation assay they were more potent than SP2012 (SEQ ID No:3). In addition SP2006 (SEQ ID No: 18), which did not inhibit proliferation, exhibited inhibitory activity in both the adhesion and migration assays. The significance of the NINNV (SEQ ID No:36) sequence is supported by the absence of activity in the fragments which lack this region (SP2007 (SEQ ID No:24), SP2008 (SEQ ID No:25), SP2013 (SEQ ID No:26) and SP2014 (SEQ ID No:27)). These results also are in accordance with the inhibitory activity in the proliferation assay.

FIG. 13 shows the HUVEC tube formation assay for the C-terminal deletion peptides. Images shown are compared to an untreated control in complete media. Inhibition of tube formation was seen for SP2006 (SEQ ID No:18), SP2028 (SEQ ID No:20), SP2029 (SEQ ID No:21), SP2032 (SEQ ID No:22), and SP2033 (SEQ ID No:23).

TABLE 4

Summary of C-terminal Deletions

| Peptide No./ SEQ ID No. | Peptide sequence | Proliferation Inhibition (IC50 in uM) | Migration Inhibition (50 uM) | Adhesion Inhibition (100 uM) | Tube formation Inhibition (100 uM) |
| --- | --- | --- | --- | --- | --- |
| SP2004/28 | LRRFSTMPFMF-OH | Inactive | Inactive | | |
| SP2006/18 | LRRFSTMPFMFAbuNINV-OH | 56.2 | 17% | 95%% | Complete |
| SP2007/24 | LRRFSTMPFMFAbu | Inactive | Inactive | 11% | Inactive |
| SP2008/25 | LRRFSTMP | Inactive | Inactive | -0.1% | Inactive |
| SP2013/26 | LNRFSTMPF-OH | Inactive | Inactive | 0.3% | Inactive |
| SP2014/27 | LRRFSTNlePFNleF-OH | Inactive | Inactive | 2.9% | Inactive |
| SP2028/20 | LRRFSTMPFMFAbuNINN | 9.45 | 48.87% | 96.8% | Complete |
| SP2029/21 | LRRFSTMPFMFTNINV | 31.09 | 54.13% | 93.75% | Complete |
| SP2032/22 | LRRFSTMPFMFTNINN | 16.91 | 32.45% | 63% | Complete |
| SP2033/23 | LRRFSTMPFMFININN | 15.06 | 42.01% | 94% | Complete |

TABLE 5

C-terminus Truncations and Peptide Proliferation Activity

| Peptide No./SEQ ID No. | Peptide Name | Peptide sequence | Number of residues | Modification from the SP2012 | $IC_{50}$ ± 95% CI (μM) |
| --- | --- | --- | --- | --- | --- |
| SP2012/3 | SP2012 | LRRFSTMPFMFAbuNINNVAbuNF | 20 | Parent peptide for this study | 48.1 ± 23.1 |
| SP2004/28 | SP2004 | LRRFSTMPFMF | 11 | Truncated 9 residues | >100 |
| SP2006/18 | SP2006 | LRRFSTMPFMFAbuNINV | 16 | Truncated 4 residues | >100 |
| SP2007/24 | SP2007 | LRRFSTMPFMFAbu | 12 | Truncated 8 residues | >100 |
| SP2008/25 | SP2008 | LRRFSTMP | 8 | Truncated 12 residues | >100 |
| SP2013/26 | SP2013 | LNRFSTMPF | 9 | Truncated 12 residues & substituted one Arginine with Asparigine | >100 |
| SP2014/27 | SP2014 | LRRFSTXPFXF -X = NorLeu | 11 | Truncated 9 residues & | >100 |

TABLE 5-continued

C-terminus Truncations and Peptide Proliferation Activity

| Peptide No./SEQ ID No. | Peptide Name | Peptide sequence | Number of residues | Modification from the SP2012 | IC$_{50}$ ± 95% CI (μM) |
|---|---|---|---|---|---|
| | | | | substituted Methionine with NorLeucine | |
| SP2028/20 | SP2028 | LRRFSTMPFMFAbuNINN | 16 | Truncated 4 residues | 5.1 ± 2.7 |
| SP2029/21 | SP2029 | LRRFSTMPFMFTNINV | 16 | Truncated 4 residues & substituted the Abu residues with Threonine | 4.8 ± 2.8 |
| SP2032/22 | SP2032 | LRRFSTMPFMFTNINN | | Truncated 4 residues & substituted the Abu residues with Threonine | 10.3 ± 4.1 |
| SP2033/23 | SP2033 | LRRFSTMPFMFININN | 16 | Truncated 4 residues & substituted the Abu residues with Isolucine | 3.8 ± 1.7 |

Example 4

N-Terminal Deletions

The peptides generated by removing amino acids from the N-terminus are listed in Table 6. In contrast with the previous series of C-terminus truncations the peptides that lack residues from the N-terminus are virtually inactive at inhibiting proliferation of HUVEC.

FIG. 14 illustrates the inhibitory activity of compounds generated by truncations from the N-terminus in adhesion (Panel A) and migration (Panel B) of HUVECs. These compounds displayed a range of inhibitory activity in the adhesion and migration assays. For the purpose of comparison, any compound displaying an inhibitory potential of greater than 30% (in the graphs a % inhibition from control lower than 70%) was considered active. Thus in the group of truncations from the N-terminus, peptides SP2010 (SEQ ID No:29) and SP2011 (SEQ ID No:30) showed low inhibitory activity in the adhesion assay and SP2009 (SEQ ID No:31) showed inhibitory activity in the migration assay. All these compounds included the critical NINNV (SEQ ID No:36) fragment. The peptides active in adhesion inhibition contained residues which extended in both directions from the NINNV (SEQ ID No:36) sequence while SP2009 (SEQ ID No:31) which only inhibited migration included additional residues to the C-terminus of the NINNV (SEQ ID No:36) sequence. Thus the context in which the NINNV (SEQ ID No:36) region is presented seems to play a role in influencing the type of activity that a compound will demonstrate.

TABLE 6

Summary of N-terminal Deletions

| Peptide No./ SEQ ID No. | Peptide sequence | Proliferation Inhibition (IC50 in μM) | Migration Inhibition (50 μM) | Adhesion Inhibition (100 μM) | Tube formation Inhibition (100 μM) | MDA-MB-231 xenograft inhibition |
|---|---|---|---|---|---|---|
| SP2009/ 31 | NINNVAbuNF-OH | Inactive | 55% | 0% | Partial | |
| SP2010/ 29 | FMFAbuNINNVAbuNF-OH | 155 | 13% | 82.69% | Complete | |
| SP2011/ 30 | STMPFMFAbuNINNVAbuNF-OH | 51.4 | Inactive | 0% | Partial | Active |

Example 5

Deletions from Both the N- and C-Terminal Ends

Peptide fragments generated by removing residues from both termini are listed in Table 7. The proliferation, adhesion, and migration inhibitory activity suggests that shorter fragments were less active even if they retained most of the NINNV (SEQ ID No:36) sequence (SP2021 (SEQ ID No:32) and SP2030 (SEQ ID No:33). However, addition of two more residues to the N-terminus of the NINNV (SEQ ID No:36) fragment along with the replacement of Abu by Threonine (SP2031; SEQ ID No:34) restored activity to similar levels as the larger 16 amino acid C-terminus truncations. These results in conjunction with the fact that splitting the molecule in two almost equal pieces led to an inactive and active compound, SP2004 (SEQ ID No:28) and SP2020 (SEQ ID No:35) respectively, indicates that the presence of particular residues is crucial. These results suggest that the NINNV (SEQ ID No:36) sequence is critical to the inhibitory activity of our peptides; however, additional amino acid residues on either end (SP2031; SEQ ID No:34) or just at the C-terminus improve activity.

The pattern of activity in adhesion and migration inhibition by some of the fragments generated by truncations from both termini and from the N-terminal deletions is presented in FIG. 15. Panel A lists the amino acid sequences of the peptides used in this series of experiments. Panel B illustrates the adhesion assays, Panel C shows the migration assays, and Panel D illustrates the proliferation assays. Table 7 lists a summary of the results of each of these experiments.

Another experiment was performed with only the peptides truncated at both ends compared to SP2012 (SEQ ID No: 3) (FIG. 16). The SAR was similar to the one observed in inhibitory activity of proliferation; the absence of the NINNV (SEQ ID No:36) sequence led to inactivation of these compounds (SP2021 (SEQ ID No:32) and SP2030 (SEQ ID No:33)). SP2031 (SEQ ID No:34) which includes the NINNV (SEQ ID No:36) sequence along with substitution of Threonine in lieu of the Abu residue displayed robust activity across all assays; proliferation inhibition ($IC_{50}$ 4.6 µM), adhesion (>80 inhibition), and migration (>50% inhibition).

Some of the peptides with N-terminal deletions and both N-terminal and C-terminal deletions were tested in the tube formation assay (FIG. 17). SP2010 (SEQ ID No:29) and SP2020 (SEQ ID No:35) at 100 µM showed complete inhibition of tube formation.

TABLE 7

Summary of Deletions from both the N- and C-terminal Ends

| Peptide No./ SEQ ID No. | Peptide sequence | Proliferation Inhibition (IC50 in uM) | Migration Inhibition (50 uM) | Adhesion Inhibition (100 uM) | Tube formation Inhibition (100 uM) |
|---|---|---|---|---|---|
| SP2020/ 35 | F(Abu)NINNV(Abu)N | Inactive | 31.89% | 84.4% | Complete |
| SP2021/ 32 | F(Abu)NIN | Inactive | Inactive | 0% | Inactive |
| SP2030/ 33 | FAbuNINV | 144.5 | -9.5% | 0% (-1.35%) | Inactive |
| SP2031/ 34 | FTNINNVTN | 214 | 10.21% | 85% | Active |

TABLE 8

Truncations from both Termini and Peptide Proliferation Activity

| Peptide No./SEQ ID No. | Peptide Name | Peptide sequence | Number of residues | Modification from the SP2012 | $IC_{50}$ ± 95% CI (µM) |
|---|---|---|---|---|---|
| SP2012/3 | SP2012 | LRRFSTMPFMFAbuNINNVAbuNF | 20 | Parent peptide for this study | 48.1 ± 23.1 |
| SP2020/3 5 | SP2020 | FAbuNINNVAbuN | 9 | Truncated 11 residues | 9.8 ± 4.6 |
| SP2021/3 2 | SP2021 | FAbuNIN | 5 | Truncated 15 residues | >100 |
| SP2030/3 3 | SP2030 | FAbuNINV | 6 | Truncated 14 residues | >100 |
| SP2031/3 4 | SP2031 | FTNINNVTN | 9 | Truncated 11 residues & substituted | 4.7 ± 1.5 |

TABLE 8-continued

Truncations from both Termini and Peptide Proliferation Activity

| Peptide No./SEQ ID No. | Peptide Name | Peptide sequence | Number of residues | Modification from the SP2012 | IC$_{50}$ ± 95% CI (μM) |
|---|---|---|---|---|---|
| | | | | the Abu residues with Threonine | |

Example 6

Substitutions and Second Generation Substitutions in the Full Length Peptide The truncation studies demonstrated that the Abu positions (in SP2012; SEQ ID No:3) are important in maintaining strong activity in the inhibition of proliferation of endothelial cells thus additional substitutions were introduced at these positions (12 and 18). These substitutions are presented in Table 9. The inhibitory activity of these peptides was not affected when the Abu was substituted by Serine (SP2022; SEQ ID No:9), Threonine (SP2025; SEQ ID No:12), AllyGly (SP2026; SEQ ID No:13) or Valine (SP2027; SEQ ID No:14) thus hydrophilicity at these locations is not crucial. Hydrophobic residues such as Alanine or Isoleucine increased the activity dramatically, 2.8 and 6.5 times, respectively.

One of the most active full length peptides, SP2024 (SEQ ID No:11), which contains Isoleucines instead of Abu residues present in the parent peptide (SP2012; SEQ ID No:3) was modified to generate additional 2$^{nd}$ generation peptides. These compounds are illustrated in Table 10. Two of these peptides (SP2034 (SEQ ID No:15) and SP2035 (SEQ ID No:16) demonstrated submicromolar activity in proliferation (IC$_{50}$ 0.54±0.19 and 0.94±0.38 μM respectively), a remarkable increase in activity from the parent peptide, SP2012 (SEQ ID No:3) (IC$_{50}$ 48.1±23.1 μM). It is interesting to note that substitution of the second Methionine in position 10 (SP2034; SEQ ID No:15) with the non-natural amino acid d-Alanine or Alanine led to considerable increases in activity, while the additional substitution of the Methionine at position 7 resulted in a 10-fold loss of activity compared to substitution of Methionine at position 10 (SP2036; SEQ ID No:17).

The introduction of methionine substitutions led to significant increases in activity in adhesion inhibition as illustrated in FIGS. 18 and 19. The parent compound (SP2012; SEQ ID No:3) exhibited an IC$_{50}$ in adhesion inhibition of 2.39±1.55 μM, which was not affected by the introduction of the Isoleucine in lieu of the Abu residues at positions 12 and 18 (SP2024 (SEQ ID No:11); IC$_{50}$ 2.35±1.3 μM). The IC$_{50}$ was not affected by further substitutions of either one Methionine (position 10) or both (position 7 and 10) with Alanine (SP2035 (SEQ ID No:16); IC$_{50}$ 2.51±0.88 μM and SP2036 (SEQ ID No:17); IC$_{50}$ 2.75±1.22 μM). However, this activity was increased four times by the introduction of D-Alanine in lieu of the Methionine at position 7 (SP2034 (SEQ ID No:15); IC$_{50}$ 0.55±0.37 μM). Similarly the inhibition of proliferation was increased from the parent SP2012 (SEQ ID No:3; IC$_{50}$ 48.1±23.1 μM) by one order of magnitude in SP2024 (SEQ ID No:11; IC$_{50}$ 7.45±5.7 μM) and even further by two order of magnitudes from SP2012 (SEQ ID No:3) to SP2034 (SEQ ID No:15) and SP2035 (SEQ ID No:16) with IC$_{50}$ 0.54±0.19 μM and IC$_{50}$ 0.98±0.38 μM respectively.

Since the ability to inhibit tube formation is a comprehensive assessment of the anti-angiogenic potential, the activity of these peptides on HUVEC tube formation was determined (FIG. 20). The inhibition of tube formation was tested at a high dose, 100 μM, so that the inhibition was obvious thus eliminating the need for quantification. Based on the results from adhesion and migration it was expected that in the group of C-terminus truncation peptides SP2028 (SEQ ID No:20), SP2029 (SEQ ID No:21), SP2032 (SEQ ID No:22) and SP2033 (SEQ ID No:23) would have activity in the inhibition of tube formation. Surprisingly, SP2006 (SEQ ID No:18) also was active at inhibiting tube formation, even though it was inactive in the migration assay. The compound had 18% activity in inhibiting migration which was below the threshold of at least 70% activity. However SP2006 (SEQ ID No:18) had strong activity in the adhesion assay thus it supports its activity in inhibition of tube formation. On the other hand the N-terminus truncated SP2011 (SEQ ID No:30) showed no activity in tube formation as expected because it was inactive in the migration assay and it only had minimal activity in adhesion. Both SP2009 (SEQ ID No:31) and SP2010 (SEQ ID No:29) displayed activity in inhibiting tube formation as expected and were active at inhibiting adhesion or migration, respectively.

The group of peptides generated by truncations from both ends included two active compounds (SP2020 (SEQ ID No:35) and SP2031 (SEQ ID No:34)) and two inactive compounds (SP2021 (SEQ ID No:32) and SP2031 (SEQ ID No:34)). All compounds in the substitution and 2$^{nd}$ generation substitution group were very active at inhibiting tube formation which is expected as their potency in migration and adhesion was either increased or not affected by the substitutions.

TABLE 9

Amino Acid Substitutions and Peptide Activity in Proliferation
Table 9 Amino acid substitutions and peptide activity in proliferation

| Peptide No./SEQ ID No. | Peptide Name | Peptide sequence | Modification from the SP2012 | IC$_{50}$ ± 95% CI (μM) |
|---|---|---|---|---|
| SP2012/3 | SP2012 | LRRFSTMPFMFAbuNINNVAbuNF | Parent peptide for this study | 48.1 ± 23.1 |

TABLE 9-continued

Amino Acid Substitutions and Peptide Activity in Proliferation
Table 9 Amino acid substitutions and peptide activity in proliferation

| Peptide No./SEQ ID No. | Peptide Name | Peptide sequence | Modification from the SP2012 | IC$_{50}$ ± 95% CI (μM) |
|---|---|---|---|---|
| SP2022/9 | SP 2022 | LRRFSTMPFMF S NINNV S NF | Abu residues replaced by Serine | 44.9 ± 29.4 |
| SP2023/10 | SP 2023 | LRRFSTMPFMF A NINNV A NF | Abu residues replaced by Alanine | 17.3 ± 6.0 |
| SP2024/11 | SP 2024 | LRRFSTMPFMF I NINNV I NF | Abu residues replaced by Isoleucine | 7.45 ± 5.7 |
| SP2025/12 | SP 2025 | LRRFSTMPFMF T NINNVT NF | Abu residues replaced by Threonine | 63.8 ± 35.0 |
| SP2026/13 | SP 2026 | LRRFSTMPFMF(AllyGly)NINNV(AllyGly)NF | Abu residues replaced by AllyGly | 47.3 ± 29.2 |
| SP2027/14 | SP 2027 | LRRFSTMPFMF V NINNV V NF | Abu residues replaced by Valine | 33.9 ± 17.9 |

TABLE 10

Inhibition of HUVEC Proliferation by SP2024, SP2034, SP2035, and SP2036

| Peptide No./SEQ ID No. | Peptide Name | Peptide sequence | Modification from the original sequence SP2000 | IC$_{50}$ ± 95% CI (μM) CI |
|---|---|---|---|---|
| SP2024/11 | SP 2024 | LRRFSTMPFM FI NINNVI NF | Cysteines replaced by Isolucine | 7.45 ± 5.7 |
| SP2034/15 | SP 2034 | LRRFSTMPFdA FI NINNVINF | Second Methionine replaced by dAlanine | 0.54 ± 0.19 |
| SP2035/16 | SP 2035 | LRRFSTMPFA FI NINNVINF | Second Methionine replaced by Alanine | 0.94 ± 0.38 |
| SP2036/17 | SP 2036 | LRRFSTAPFA FI NINNVINF | Both Methionine replaced by Alanine | 9.97 ± 8.3 |

TABLE 11

Summary of Activity for All Compounds

| Peptide No./SEQ ID No. | Peptide Name | Peptide sequence | Activity in Proliferation | Activity in Adhesion | Activity in Migration | Activity in Tube formation |
|---|---|---|---|---|---|---|
| SP2024/11 | SP2012 | LRRFSTMPFMFAbuNINNVAbuNF | Yes | Yes | Yes | Yes |
| SP2004/28 | SP2004 | LRRFSTMPFMF | No | No | No | No |
| SP2006/18 | SP2006 | LRRFSTMPFMFAbuNINV | No | Yes | No | Yes |
| SP2007/24 | SP2007 | LRRFSTMPFMFAbu | No | No | No | No |
| SP2008/25 | SP2008 | LRRFSTMP | No | No | No | No |
| SP2013/26 | SP2013 | LNRFSTMPF | No | No | No | No |
| SP2014/27 | SP2014 | LRRFSTXPFXF -X = NorLeu | No | No | No | No |

TABLE 11-continued

Summary of Activity for All Compounds

| Peptide No./SEQ ID No. | Peptide Name | Peptide sequence | Activity in Proliferation | Activity in Adhesion | Activity in Migration | Activity in Tube formation |
|---|---|---|---|---|---|---|
| SP2028/20 | SP2028 | LRRFSTMPFMFAbuNINN | Yes | Yes | Yes | Yes |
| SP2029/21 | SP2029 | LRRFSTMPFMFTNINV | Yes | Yes | Yes | Yes |
| SP2032/22 | SP2032 | LRRFSTMPFMFTNINN | Yes | Yes | Yes | Yes |
| SP2033/23 | SP2033 | LRRFSTMPFMFININN | Yes | Yes | Yes | Yes |
| SP2009/31 | SP2009 | NINNVAbuNF | No | No | Yes | Yes |
| SP2010/29 | SP2010 | FMFAbuNINNVAbuNF | No | Yes | No | Yes |
| SP2011/30 | SP2011 | STMPFAbuNINNVAbuNF | No | Yes | No | No |
| SP2020/35 | SP2020 | FAbuNINNVAbuN | Yes | Yes | Yes | Yes |
| SP2021/32 | SP2021 | FAbuNIN | No | No | No | No |
| SP2030/33 | SP2030 | FAbuNINV | No | No | No | No |
| SP2031/34 | SP2031 | FTNINNVTN | Yes | Yes | Yes | Yes |
| SP2022/9 | SP2022 | LRRFSTMPFMF S NINNV S NF | Yes | Yes | Yes | Yes |
| SP2023/10 | SP2023 | LRRFSTMPFMF A NINNV A NF | Yes | Yes | Yes | Yes |
| SP2024/11 | SP2024 | LRRFSTMPFMF I NINNV I NF | Yes | Yes | Yes | Yes |
| SP2025/12 | SP2025 | LRRFSTMPFMF T NINNVT NF | Yes | Yes | Yes | Yes |
| SP2026/13 | SP2026 | LRRFSTMPFMF(AllyGly)NINNV(AllyGly)NF | Yes | Yes | Yes | Yes |
| SP2027/14 | SP2027 | LRRFSTMPFMF V NINNV V NF | Yes | Yes | Yes | Yes |
| SP2034/15 | SP2034 | LRRFSTMPFdA FI NINNVINF | Yes | Yes | Yes | Yes |
| SP2035/16 | SP2035 | LRRFSTMPFA FI NINNVINF | Yes | Yes | Yes | Yes |
| SP2036/17 | SP2036 | LRRFSTAPFA FI NINNVINF | Yes | Yes | Yes | Yes |

The structure-activity relationship of anti-angiogenic peptides whose original peptide (SP2000; SEQ ID No:19) was derived from the α5 fibril of type IV collagen was analyzed (Summary in Table 11). The potent cysteine-free peptide (SP2012; SEQ ID No:3), the parent peptide for this study, was tested in vitro and in vivo xenograft mouse model of triple negative breast cancer, a form of cancer which is not amendable to conventional chemotherapeutic and hormonal treatments (Avraamides, et al., 2008).

The presently disclosed subject matter provides a small family of peptides which were screened in a series of in vitro assays: proliferation, adhesion, migration and tube formation with macrovascular endothelial cells (HUVEC) commonly used in angiogenesis studies. Selected peptides also were tested using microvascular endothelial cells (MEC), lymphatic endothelial cells (LEC) and MDA-MB-231 breast cancer cells and showed similarity of responses for these cell types. The proliferation inhibition activity was retained when most of the sequence was preserved (SP2028; SEQ ID No:20) or when specific substitutions were introduced. Shorter fragments that still maintained activity included the NINNV (SEQ ID No:36) sequence which was coupled with additional amino acids on both sides for optimal activity (SP2009 (SEQ ID No:31) vs. SP2020 (SEQ ID No:35)). The in vitro activity was improved by two orders of magnitude in comparison to that of the parent peptide, when the length was maintained and certain substitutions were introduced (SP2034; SEQ ID No:15). Overall adhesion and migration profiles were similar; generally a compound active at inhibiting adhesion would also be active at inhibiting migration. Similarly the activity in the inhibition of adhesion and migration was maintained if the NINNV (SEQ ID No:36) sequence was conserved (SP2004 (SEQ ID No:28) vs. SP2028 (SEQ ID No:20)). However, the addition of amino acids to this sequence seemed to play a different role: if the NINNV (SEQ ID No:36) region was flanked with residues from the C-terminus (SP2009; SEQ ID No:31) the compound was active in migration and not adhesion while if it was flanked with residues from the N-terminus (SP2006; SEQ ID No:18) the activity was reversed, i.e. the compound was active in adhesion but not migration. Despite the similarities in the activity profiles of adhesion and migration there were a few exceptions, e.g. SP2006 (SEQ ID No:18), SP2010 (SEQ ID No:29), SP2011 (SEQ ID No:30) compounds which are active in adhesion but not in migration and compound SP2009 (SEQ ID No:31) which was active in migration but not adhesion.

Inhibition of tube formation correlates very well with activity in either inhibition of adhesion or migration; if a compound was active in either of those two assays it consistently demonstrated activity in the inhibition of tube formation. High concentrations of peptides were used to assess the activity in this assay so that the inhibition was complete and there was no need for quantification of the effects. Also, two different phenotypes were observed in the inhibition by these compounds; one in which the cells were clumped (e.g., FIG. 23, panel B), and the other in which the cells were less clumped and formed fragile and short tubes (e.g., FIG. 23, panel A). The clumped profile was observed with all the compounds that inhibited adhesion while the short tubes profile was associated with compounds which were active in migration. In the compounds that were active in both, adhesion and migration, the clump profile predominated however. Live-dead staining of cells treated with the compounds (results not shown) have indicated that cells which were at the bottom of the clump were dead while cells which were in contact with other cells were still alive but could not rearrange due to their inability to migrate.

In summary, a structure-activity relationship study has been presented herein for a family of anti-angiogenic peptides. A number of amino acids and amino acid sequences which were important for in vitro activity of these compounds has been found. A short sequence, NINNV (SEQ ID No:36), was found to be important in the activity of this peptide in inhibiting proliferation, adhesion, migration and tube formation in HUVEC. The results were qualitatively similar to those in MEC and LEC. These appear to be the only known peptides that exhibit anti-lymphangiogenic activity. Through specific and directed substitutions, compounds were created which exhibited a significant (in some cases, two orders of magnitude) increase in activity over the activity of parent peptide.

Example 7

Inhibitory Activity of Peptides on Multiple Cell Types

Even though HUVEC remain the most common cells used in angiogenesis assays, they are derived from veins, and thus there are questions whether they are the most appropriate model for studying angiogenesis. It has been shown that many of the in vitro assays with HUVEC and microvascular endothelial cells (MEC) exhibit qualitatively similar behaviors (Avraamides, et al., 2008). FIG. 21 shows the inhibition activity of the parent peptide SP2012 (SEQ ID No:3) and SP2024 (SEQ ID No:11) in an adhesion assay (Panel A) and in a migration assay (Panel C) on lymphatic endothelial cells (LEC). This figure also shows the inhibition activity of the parent peptide SP2012 (SEQ ID No:3) and SP2024 (SEQ ID No:11) in an adhesion assay (Panel B) and in a migration assay (Panel D) on microvascular cells (MEC) and migration inhibition on breast cancer cells MDA-MB-231 (Panel E). These results demonstrate that these peptides are quite active at inhibiting adhesion and migration of MEC. Further, the activity of these two peptides at inhibiting the adhesion and migration of lymphatic endothelial cells (LEC) and the MDA-MB-231 breast cancer cells also was strong. Thus these peptides possess inhibitory activity towards multiple cell types thus potentially inhibiting the growth of blood and lymphatic vessels and also tumor growth and metastasis.

FIG. 22 again demonstrates the inhibitory activity of SP2024 (SEQ ID No:11) on breast cancer cells MDA-MB-231. Panel A shows inhibition of cell adhesion by the SP2024 (SEQ ID No:11) peptide and Panel B demonstrates inhibition of cell migration.

Example 8

Inhibitory Activity of Peptides In Vivo

For the tumor xenograft assay, animals were housed and treated according to the approved animal protocol of the Institutional Care and Use Committee at Johns Hopkins Medical Institution (JHMI). Orthotopic breast tumors were initiated in SCID mice using MDA-MB-231 cells. $2 \times 10^6$ cells per 100 µL aliquot of single cell suspension were injected in the breast mammary fat pad. Tumors reached volumes of 75 mm$^3$ to 100 mm$^3$ in approximately 14-21 days. Mice were randomized and arranged in groups (8 mice per group) with similar tumor volumes (no statistical difference among averages) and treatment was commenced. Peptides were administered once per day intraperitoneally (i.p.) at doses of 10 mg/kg (subcutaneous delivery was also tested with certain peptides). Paclitaxel was administered at 5 mg/kg once a week, and to maintain the daily treatment regime PBS was administered on the non-treatment days. Tumors were measured every fourth day using calipers and the tumor volume was calculated using the formula $V=ab^2/2$, where a is the larger diameter and b is the smaller diameter.

A Matrigel plug assay was performed to evaluate the inhibitory effect of the peptides in angiogenesis and lymphangiogenesis in vivo. Basement Membrane Matrix (Matrigel, growth factor reduced, high concentration, LDEV-free, BD Biosciences) containing VEGFA (380 ng/mL) and heparin (10 unit) was mixed with or without the peptides making total volume of 400 µL. The final concentration of the peptides was 25 µM. DMSO contents were controlled identically within all experimental groups. The Matrigel mixtures were subcutaneously injected on both flanks on the abdominal side of athymic nude mice under anesthesia (25% xylazine+25% acepromazine (vol/vol) in PBS giving a concentration of 50 mg/kg of ketamine and 5 mg/kg of acepromazine). Animals were housed and treated according to the approved animal protocol of the Institutional Care and Use Committee at Johns Hopkins Medical Institution (JHMI). After 10 days mice were euthanized and the gels were removed and weighed. At the end of the study, a few mice were infused intravenously with 200 µL of FITC (fluorescein isothiocyanate)-Dextran (20 mg/mL; Santa Cruz Biotechnology, Santa Cruz, Calif.) and 1 h later, Matrigel plugs were surgically removed and placed in 10% formalin (BD Biosciences, San Diego, Calif.) for 16 hours, then washed in PBS, homogenized, and quantified in a 96-well fluorescent plate reader. Representative sections were imaged using a Nikon microscope to show the amount of vascular invasion into the gel. Quantification of vessels was performed by using immunohistochemistry.

The ocular laser-induced choroidal neovascularization (NV) model of wet age-related macular degeneration was used for testing. 5-6-week-old female pathogen-free C57BL/6 mice were anesthetized with ketamine hydrochloride (100 mg/kg body weight) and pupils were dilated. Laser photocoagulation (75-µm spot size, 0.1-sec duration, 120 mW) was performed in the 9, 12, and 3 o'clock positions of the posterior pole of each eye with the slit lamp delivery system of an OcuLight GL diode laser (Index, Mountain View, Calif.) and a handheld cover slip as a contact lens to view the retina. Production of a tissue bubble by the laser, which indicates rupture of Bruch's membrane, is an important factor in obtaining choroidal NV; therefore, only burns in which a bubble is produced are included in the study. Immediately after laser-induced rupture of Bruch's membrane, mice (n=15 for each dose) were given an intravitreous injection of 1 μl of phosphate-buffered saline (PBS) containing 0.1 μg of peptide, 0.1 μg scrambled peptide. At day 7 the mice that received the naked peptides were dosed again whereas the mice that received the particles were administered PBS. Intravitreous injections were done under a dissecting microscope with a Harvard Pump Microinjection System and pulled glass micropipettes. After 14 days, the mice were perfused with 1 mL of PBS containing 50 mg/mL of fluorescein-labeled dextran ($2 \times 10^6$ Daltons average molecular weight; Sigma-Aldrich, St. Louis, Mo.) and choroidal flat mounts were examined by fluorescence microscopy. Images were captured with a Nikon Digital Still Camera DXM1200 (Nikon Instruments Inc., New York, N.Y.). Image analysis software (Image-Pro Plus; Media Cybernetics, Silver Spring, Md.) was used to measure the total area of choroidal NV at each rupture site with the investigator masked with respect to treatment group.

The ocular Rho/VEGF transgenic mice model of wet age-related macular degeneration also was used to test some of the peptides. Transgenic mice in which the rhodopsin promoter drives expression of VEGF in photoreceptors have the onset of VEGF production at P7 and develop extensive NV along the outer surface of the retina by P21 (Okamoto et al., 1997; Tobe et al., 1998). Mice hemizygous for the transgene (n=15 for each dose) were given an intraocular injection of 1 μl of PBS containing 0.01, 0.1, or 1 μg of peptide or scramble peptide in one eye at P7 and P14 and at P21 the mice were anesthetized, perfused with fluorescein-labeled dextran, and the total area of neovascularization on the outer surface of the retina was measured on retinal flat mounts by image analysis as above.

Some of the peptides were tested in vivo using the tumor xenograft assay in mice. FIG. 23 shows the suppression of tumor growth by peptides SP2000 (SEQ ID No:19) and SP2012 (SEQ ID No:3) (Panel A). In this experiment, the control group (PBS with 10% DMSO) and the experimental groups (10 mg/kg of peptide to mouse weight) were tested. Measurements were performed every fourth day. Error bars depict SEM. As can be seen from the graph, tumor growth was inhibited by SP2000 (SEQ ID No:19) and SP2012 (SEQ ID No:3). Panel B shows the quantification of microvascular density after the completion of the treatment at 21 days. All groups were statistically different from one another (p<0.05)

FIG. 24 demonstrates the inhibition of breast cancer cells MDA-MB-231 by the peptide SP2024 (SEQ ID No:11). Panel A shows that SP2024 (SEQ ID No:11) inhibited tumor growth significantly over the control. Panel B demonstrates that SP2024 (SEQ ID No:11) reduced relative vascular volume and Panel C showed that the peptide reduced tumor permeability-surface area product compared to the control as measured by MRI.

FIG. 25 demonstrates that SP2024 (SEQ ID No:11) inhibits lung metastasis in an experiment with luciferase-transfected MDA-MB-231 cells injected into nude mice, as measured with a Xenogen IVIS system. FIG. 26 shows the results from the injection of SP2024 (SEQ ID No:11) (0.01, 0.1, or 1 μg) into the mouse eye. Both the area of choroidal neovascularization (Panel A) and the area of retinal neovascularization (Panel B) generally decreased as the amount of SP2024 (SEQ ID No:11) was increased.

Several other peptides, SP2034, SP2035 and SP2036 (SEQ ID Nos: 15-17), also were tested in vivo. FIG. 27 shows that the injection of SP2034, SP2035, or SP2036 (SEQ ID Nos: 15-17) (0.1 μg) into a mouse eye inhibited laser-induced choroidal neovascularization (Panel A) and the area of retinal neovascularization in the Rho/VEGF model (Panel B). In this case, 0.1 μg of SP2036 (SEQ ID No:17) administered directly into the eye inhibited VEGF mediated angiogenesis by about 70%.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Abraham S, Guo F, Li L S, Rader C, Liu C, Barbas C F, 3rd, et al. (2007) Synthesis of the next generation therapeutic antibodies that combine cell targeting and antibody-catalyzed prodrug activation. *Proc Natl Acad Sci USA;* 104: 5584-9.

Arnaoutova I, George J, Kleinman H K, Benton G (2009) The endothelial cell tube formation assay on basement membrane turns 20: state of the science and the art. *Angiogenesis;* 12: 267-74.

Avraamides, C. J.; Garmy-Susini, B.; Varner, J. A. Integrins in angiogenesis and lymphangiogenesis. *Nat. Rev. Cancer,* 2008, 8(8), 604-617.

Bhujwalla Z M, Artemov D, Natarajan K, Ackerstaff E, Solaiyappan M. Vascular differences detected by MRI for metastatic versus nonmetastatic breast and prostate cancer xenografts. Neoplasia 2001; 3:143-53.

Bhutia, S. K.; Maiti, T. K. Targeting tumors with peptides from natural sources. *Trends Biotechnol.,* 2008, 26(4), 210-217.

Bradley, D. A.; Daignault, S.; Ryan, C. J.; Dipaola, R. S.; Smith, D. C.; Small, E.; Gross, M. E.; Stein, M. N.; Chen, A.; Hussain, M. Cilengitide (EMD 121974, NSC 707544) in asymptomatic metastatic castration resistant prostate cancer patients: a randomized phase II trial by the prostate cancer clinical trials consortium. *Invest. New Drugs.*

Carmeliet, P. Angiogenesis in life, disease and medicine. *Nature,* 2005, 438(7070), 932-936.

Carmeliet, P.; Jain, R. K. Angiogenesis in cancer and other diseases. *Nature,* 2000, 407(6801), 249-257.

Carmeliet P, Jain R K. Molecular mechanisms and clinical applications of angiogenesis. Nature. 2011 May 19; 473 (7347):298-307. Eikesdal, H. P.; Sugimoto, H.; Birrane, G.; Maeshima, Y.; Cooke, V. G.; Kieran, M.; Kalluri, R. Identification of amino acids essential for the antiangiogenic activity of tumstatin and its use in combination antitumor activity. *Proc. Natl. Acad. Sci. USA,* 2008, 105(39), 15040-15045.

Elkin M and Vlodaysky I. Tail vein assay of cancer metastasis. *Curr Protoc Cell Biol Chapter* 19: Unit 19 12, 2001.

Folkman, J. Tumor angiogenesis: therapeutic implications. *N. Engl. J. Med,* 1971, 285(21), 1182-1186.

Folkman J (2002) Role of angiogenesis in tumor growth and metastasis. *Semin Oncol;* 29: 15-8.

Folkman, J., Angiogenesis. *Annu. Rev. Med.,* 2006, 57, 1-18.

Gautier B, Goncalves V, Diana D, Di Stasi R, Teillet F, Lenoir C, et al. (2010) Biochemical and structural analysis of the binding determinants of a vascular endothelial growth factor receptor peptidic antagonist. *J Med Chem;* 53: 4428-40.

Gentilucci L, De Marco R, Cerisoli L (2010) Chemical modifications designed to improve peptide stability: incorporation of non-natural amino acids, pseudo-peptide bonds, and cyclization. *Curr Pharm Des;* 16: 3185-203.

Haviv, F.; Bradley, M. F.; Kalvin, D. M.; Schneider, A. J.; Davidson, D. J.; Majest, S. M.; McKay, L. M.; Haskell, C. J.; Bell, R. L.; Nguyen, B.; Marsh, K. C.; Surber, B. W.; Uchic, J. T.; Ferrero, J.; Wang, Y. C.; Leal, J.; Record, R. D.; Hodde, J.; Badylak, S. F.; Lesniewski, R. R.; Henkin, J. Thrombospondin-1 mimetic peptide inhibitors of angiogenesis and tumor growth: design, synthesis, and optimization of pharmacokinetics and biological activities. *J. Med. Chem.,* 2005, 48(8), 2838-2846.

Holopainen T, Bry M, Alitalo K, Saaristo A. Perspectives on lymphangiogenesis and angiogenesis in cancer. J Surg Oncol. 2011 May 1; 103(6):484-8. Hruby V J, Sharma S D, Toth K, Jaw J Y, al-Obeidi F, Sawyer T K, et al. (1993) Design, synthesis, and conformation of superpotent and prolonged acting melanotropins. *Ann N Y Acad Sci;* 680: 51-63.

Karagiannis, E. D.; Popel, A. S. Identification of novel short peptides derived from the alpha 4, alpha 5, and alpha 6 fibrils of type IV collagen with anti-angiogenic properties. *Biochem. Biophys. Res. Commun.,* 2007, 354(2), 434-439.

Karagiannis E D, Popel A S. A systematic methodology for proteome-wide identification of peptides inhibiting the proliferation and migration of endothelial cells. Proc Natl Acad Sci USA. 2008 Sep. 16; 105(37):13775-80.

Kenny, L. M.; Coombes, R. C.; Oulie, I.; Contractor, K. B.; Miller, M.; Spinks, T. J.; McParland, B.; Cohen, P. S.; Hui, A. M.; Palmieri, C.; Osman, S.; Glaser, M.; Turton, D.; Al-Nahhas, A.; Aboagye, E. O. Phase I trial of the positron-emitting Arg-Gly-Asp (RGD) peptide radioligand 18F-AH111585 in breast cancer patients. *J. Nucl. Med.,* 2008, 49(6), 879-886.

Koskimaki, J. E.; Karagiannis, E. D.; Rosca, E. V.; Vesuna, F.; Winnard, P. T. Jr.; Raman, V.; Bhujwalla, Z. M.; Popel, A. S., Peptides derived from type IV collagen, CXC chemokines, and thrombospondin-1 domain-containing proteins inhibit neovascularization and suppress tumor growth in MDA-MB-231 breast cancer xenografts. *Neoplasia,* 2009, 11(12), 1285-1291.

Koskimaki, J. E.; Karagiannis, E. D.; Tang, B. C.; Hammers, H.; Watkins, D. N.; Pili, R.; Popel, A. S. Pentastatin-1, a collagen IV derived 20-mer peptide, suppresses tumor growth in a small cell lung cancer xenograft model. *BMC Cancer,* 2010, 10, 29.

Lee E, Rosca E V, Pandey N B, Popel A S (2011) Small peptides derived from somatotropin conserved domain-containing proteins inhibit blood and lymphatic endothelial cell proliferation, migration, adhesion and tube formation. *Int j Biochem Cell Biol;* in press:

Leung, D. W.; Cachianes, G.; Kuang, W. J.; Goeddel, D. V.; Ferrara, N. Vascular endothelial growth factor is a secreted angiogenic mitogen. *Science,* 1989, 246(4935), 1306-1309.

Li M, Oliver E, Kitchens K M, Vere J, Alkan S S, Tamiz A P (2008) Structure-activity relationship studies of permeability modulating peptide AT-1002. *Bioorg Med Chem Lett;* 18: 4584-6.

Ma J. S., Unnatural amino acids in drug discovery. CHIMICA OGGI chemistry today, 2003, 65-68. Mirochnik, Y.; Aurora, A.; Schulze-Hoepfner, F. T.; Deabes, A.; Shifrin, V.; Beckmann, R.; Polsky, C.; Volpert, O. V. Short pigment epithelial-derived factor-derived peptide inhibits angiogenesis and tumor growth. *Clin. Cancer Res.,* 2009, 15(5), 1655-1663.

Nabors, L. B.; Fiveash, J. B.; Markert, J. M.; Kekan, M. S.; Gillespie, G. Y.; Huang, Z.; Johnson, M. J.; Meleth, S.; Kuo, H.; Gladson, C. L.; Fathallah-Shaykh, H. M. A phase 1 trial of ABT-510 concurrent with standard chemoradiation for patients with newly diagnosed glioblastoma. *Arch. Neurol.,* 67(3), 313-319.

Ogan M D, Schmiedl U, Moseley M E, Grodd W, Paajanen H, Brasch R C., Albumin labeled with Gd-DTPA. An intravascular contrast-enhancing agent for magnetic resonance blood pool imaging: preparation and characterization. Invest Radiol. 1988 December; 23(12):961.

Okamoto N, Tobe T, Hackett S F, Ozaki H, Vinores M A, LaRochelle W, Zack D J, Campochiaro P A: Transgenic mice with increased expression of vascular endothelial growth factor in the retina: a new model of intraretinal and subretinal neovascularization, Am. J. Pathol. 1997, 151: 281-291.

Pernot M, Vanderesse R, Frochot C, Guillemin F, Barberi-Heyob M (2011) Stability of peptides and therapeutic success in cancer. *Expert Opin Drug Metab Toxicol;* 7: 793-802.

Raman V, Artemov D, Pathak A P, Winnard Jr P T, McNutt S, Yudina A, Bogdanov Jr A, Bhujwalla Z M. Characterizing vascular parameters in hypoxic regions: A combined magnetic resonance and optical imaging study of a human prostate cancer model. Cancer Res 2006; 66:9929-36

Reardon, D. A.; Fink, K. L.; Mikkelsen, T.; Cloughesy, T. F.; O'Neill, A.; Plotkin, S.; Glantz, M.; Ravin, P.; Raizer, J. J.; Rich, K. M.; Schiff, D.; Shapiro, W. R.; Burdette-Radoux, S.; Dropcho, E. J.; Wittemer, S. M.; Nippgen, J.; Picard, M.; Nabors, L. B. Randomized phase II study of cilengitide, an integrin-targeting arginine-glycine-aspartic acid peptide, in recurrent glioblastoma multiforme. *J. Clin. Oncol.,* 2008, 26(34), 5610-5617.

Reichert, J. Development trends for peptide therapeutics Periodical [Online], 2008, p. http://www.peptidetherapeutics.org/PTF_Summary_2008.pdf.

Rivera C G, Rosca E V, Pandey N B, Koskimaki J E, Bader J S, Popel A S (2011) Novel peptide specific QSAR analysis applied to collagen IV peptides with antiangiogenic activity. *J Med Chem;* in press:

Rosca E V, Koskimaki J E, Pandey N B, Rivera C G, Tamiz A P, Popel A S (2011) Anti-angiogenic peptides for cancer therapeutics. *Current Pharmaceutical Biotechnology;* 12: 1101-16.

Rosca E V, Koskimaki J E, Pandey N B, Wolff A C, Popel A S (2011) Development of a biomimetic peptide derived from collagen IV with anti-angiogenic activity in breast cancer. *Cancer Biology & Therapy;* 12:808-17. Saladin, P. M.; Zhang, B. D.; Reichert, J. M. Current trends in the clinical development of peptide therapeutics. *IDrugs,* 2009, 12(12), 779-784.

Senger, D. R.; Galli, S. J.; Dvorak, A. M.; Perruzzi, C. A.; Harvey, V. S.; Dvorak, H. F. Tumor cells secrete a vascular permeability factor that promotes accumulation of ascites fluid. *Science,* 1983, 219(4587), 983-985.

Tobe T, Okamoto N, Vinores M A, Derevjanik N L, Vinores S A, Zack D J, Campochiaro P A: Evolution of neovascularization in mice with overexpression of vascular endothelial growth factor in photoreceptors, Invest. Ophthalmol. Vis. Sci. 1998, 39:180-188.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. An isolated peptide consisting of the amino acid sequence LRRFSTAPFAFININNVINF (SEQ ID NO: 17), or a pharmaceutically acceptable salt thereof.

2. A pharmaceutical composition comprising the peptide of claim 1, and a pharmaceutically acceptable carrier.

3. A method for treating breast cancer or macular degeneration comprising administering an effective amount of the pharmaceutical composition of claim 2.

4. The method of claim 3, wherein the pharmaceutical composition is administered locally or systemically.

5. The method of claim 4, wherein the pharmaceutical composition is administered parenterally.

6. The method of claim 4, wherein the pharmaceutical composition is administered by intraocular delivery.

7. The method of claim 3, wherein the macular degeneration is age-related macular degeneration.

8. The method of claim 3, wherein the method treats angiogenesis in or surrounding a tumor.

9. The method of claim 8, wherein the tumor is a primary tumor or an established metastasized tumor.

10. The method of claim 8, wherein the method inhibits the establishment of metastasis or inhibits further metastasis of the tumor.

11. The method of claim 8, wherein the method inhibits dissemination of tumor cells through the blood.

* * * * *

SEQUENCE LISTING

<160> NUMBER OF SEQ ID NOS: 36

<210> SEQ ID NO 1
<211> LENGTH: 20
<212> TYPE: PRT
<213> ORGANISM: Artificial Sequence
<220> FEATURE:
<223> OTHER INFORMATION: Based on human Collagen Type IV protein
<220> FEATURE:
<221> NAME/KEY: MISC_FEATURE
<222> LOCATION: (1)..(20)
<223> OTHER INFORMATION: X is any natural or non-natural amino acid

<400> SEQUENCE: 1

Leu Arg Arg Phe Ser Thr Xaa Pro Xaa Xaa Xaa Xaa Asn Ile Asn Asn
1               5                   10                  15

Val Xaa Asn Phe
            20

<210> SEQ ID NO 2
<211> LENGTH: 20
<212> TYPE: PRT
<213> ORGANISM: Artificial Sequence
<220> FEATURE:
<223> OTHER INFORMATION: Artificial sequence based on human Collagen
      Type IV protein

<400> SEQUENCE: 2

Leu Arg Arg Phe Ser Thr Met Pro Phe Met Phe Gly Asn Ile Asn Asn
1               5                   10                  15

Val Gly Asn Phe
            20

<210> SEQ ID NO 3
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(20)
<223> OTHER INFORMATION: X is 2-aminobutyric acid (Abu)

<400> SEQUENCE: 3

Leu Arg Arg Phe Ser Thr Met Pro Phe Met Phe Xaa Asn Ile Asn Asn
1               5                   10                  15

Val Xaa Asn Phe
            20

<210> SEQ ID NO 4
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(20)
<223> OTHER INFORMATION: X is 2-aminobutyric acid (Abu)

<400> SEQUENCE: 4

Leu Arg Arg Phe Ser Thr Met Pro Ala Met Phe Xaa Asn Ile Asn Asn
1               5                   10                  15

Val Xaa Asn Phe

<210> SEQ ID NO 5
<211> LENGTH: 20
<212> TYPE: PRT
<213> ORGANISM: Artificial Sequence
<220> FEATURE:
<223> OTHER INFORMATION: Artificial sequence based on the human
     Collagen Type IV protein
<220> FEATURE:
<221> NAME/KEY: MISC_FEATURE
<222> LOCATION: (1)..(20)
<223> OTHER INFORMATION: X is 2-aminobutyric acid (Abu)

<400> SEQUENCE: 5

Leu Arg Arg Phe Ser Thr Met Pro Phe Ala Phe Xaa Asn Ile Asn Asn
1               5                   10                  15

Val Xaa Asn Phe
            20

<210> SEQ ID NO 6
<211> LENGTH: 20
<212> TYPE: PRT
<213> ORGANISM: Artificial Sequence
<220> FEATURE:
<223> OTHER INFORMATION: Artificial sequence based on the human
     Collagen Type IV protein
<220> FEATURE:
<221> NAME/KEY: MISC_FEATURE
<222> LOCATION: (1)..(20)
<223> OTHER INFORMATION: X is 2-aminobutyric acid (Abu)

<400> SEQUENCE: 6

Leu Arg Arg Phe Ser Thr Met Pro Phe Met Ala Xaa Asn Ile Asn Asn
1               5                   10                  15

Val Xaa Asn Phe
            20

<210> SEQ ID NO 7
<211> LENGTH: 20
<212> TYPE: PRT
<213> ORGANISM: Artificial Sequence
<220> FEATURE:
<223> OTHER INFORMATION: Artificial sequence based on the human
     Collagen Type IV protein
<220> FEATURE:
<221> NAME/KEY: MISC_FEATURE
<222> LOCATION: (1)..(20)
<223> OTHER INFORMATION: X at position 10 is Norleucine (Nle), X at
     position 12 is 2-aminobutyric acid (Abu), and X at position 18 is
     2-aminobutyric acid (Abu)

<400> SEQUENCE: 7

Leu Arg Arg Phe Ser Thr Met Pro Phe Xaa Phe Xaa Asn Ile Asn Asn
1               5                   10                  15

Val Xaa Asn Phe
            20

<210> SEQ ID NO 8
<211> LENGTH: 20
<212> TYPE: PRT
<213> ORGANISM: Artificial Sequence
<220> FEATURE:
<223> OTHER INFORMATION: Artificial sequence based on the human
     Collagen Type IV protein
<220> FEATURE:
<221> NAME/KEY: MISC_FEATURE
<222> LOCATION: (1)..(20)
<223> OTHER INFORMATION: X at position 11 is 4-chlorinated phenylalanine (4-ClPhe), X at position 12 is 2-aminobutyric acid
(Abu), and X at position 18 is 2-aminobutyric acid (Abu)

<400> SEQUENCE: 8

Leu Arg Arg Phe Ser Thr Met Pro Phe Met Xaa Xaa Asn Ile Asn Asn
1               5                   10                  15

Val Xaa Asn Phe
            20

<210> SEQ ID NO 9
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 9

Leu Arg Arg Phe Ser Thr Met Pro Phe Met Phe Ser Asn Ile Asn Asn
1               5                   10                  15

Val Ser Asn Phe
            20

<210> SEQ ID NO 10
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 10

Leu Arg Arg Phe Ser Thr Met Pro Phe Met Phe Ala Asn Ile Asn Asn
1               5                   10                  15

Val Ala Asn Phe
            20

<210> SEQ ID NO 11
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 11

Leu Arg Arg Phe Ser Thr Met Pro Phe Met Phe Ile Asn Ile Asn Asn
1               5                   10                  15

Val Ile Asn Phe
            20

<210> SEQ ID NO 12
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 12

Leu Arg Arg Phe Ser Thr Met Pro Phe Met Phe Thr Asn Ile Asn Asn
1               5                   10                  15

Val Thr Asn Phe
            20

<210> SEQ ID NO 13
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(20)
<223> OTHER INFORMATION: X is allylglycine (AllyGly)

<400> SEQUENCE: 13

Leu Arg Arg Phe Ser Thr Met Pro Phe Met Phe Xaa Asn Ile Asn Asn
1               5                   10                  15

Val Xaa Asn Phe
            20

<210> SEQ ID NO 14
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 14

Leu Arg Arg Phe Ser Thr Met Pro Phe Met Phe Val Asn Ile Asn Asn
1               5                   10                  15

Val Val Asn Phe
            20

<210> SEQ ID NO 15
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(20)
<223> OTHER INFORMATION: X is D-alanine

<400> SEQUENCE: 15

Leu Arg Arg Phe Ser Thr Met Pro Phe Xaa Phe Ile Asn Ile Asn Asn
1               5                   10                  15

Val Ile Asn Phe
            20

<210> SEQ ID NO 16
<211> LENGTH: 20
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 16

Leu Arg Arg Phe Ser Thr Ala Pro Phe Met Phe Ile Asn Ile Asn Asn
1               5                   10                  15

Val Ile Asn Phe
            20

<210> SEQ ID NO 17
<211> LENGTH: 20

```
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 17

Leu Arg Arg Phe Ser Thr Ala Pro Phe Ala Phe Ile Asn Ile Asn Asn
1               5                   10                  15

Val Ile Asn Phe
            20

<210> SEQ ID NO 18
<211> LENGTH: 16
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(20)
<223> OTHER INFORMATION: X is 2-aminobutyric acid (Abu)
<220> FEATURE:
<221> NAME/KEY: MISC_FEATURE
<222> LOCATION: (1)..(16)
<223> OTHER INFORMATION: X is 2-aminobutyric acid (Abu)

<400> SEQUENCE: 18

Leu Arg Arg Phe Ser Thr Met Pro Phe Met Phe Xaa Asn Ile Asn Val
1               5                   10                  15

<210> SEQ ID NO 19
<211> LENGTH: 20
<212> TYPE: PRT
<213> ORGANISM: Homo sapiens

<400> SEQUENCE: 19

Leu Arg Arg Phe Ser Thr Met Pro Phe Met Phe Cys Asn Ile Asn Asn
1               5                   10                  15

Val Cys Asn Phe
            20

<210> SEQ ID NO 20
<211> LENGTH: 16
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(16)
<223> OTHER INFORMATION: X is 2-aminobutyric acid (Abu)

<400> SEQUENCE: 20

Leu Arg Arg Phe Ser Thr Met Pro Phe Met Phe Xaa Asn Ile Asn Asn
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 21
```

```
Leu Arg Arg Phe Ser Thr Met Pro Phe Met Phe Thr Asn Ile Asn Val
1               5                   10                  15
```

<210> SEQ ID NO 22
<211> LENGTH: 16
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 22

```
Leu Arg Arg Phe Ser Thr Met Pro Phe Met Phe Thr Asn Ile Asn Asn
1               5                   10                  15
```

<210> SEQ ID NO 23
<211> LENGTH: 16
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 23

```
Leu Arg Arg Phe Ser Thr Met Pro Phe Met Phe Ile Asn Ile Asn Asn
1               5                   10                  15
```

<210> SEQ ID NO 24
<211> LENGTH: 12
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(12)
<223> OTHER INFORMATION: X is 2-aminobutyric acid (Abu)

<400> SEQUENCE: 24

```
Leu Arg Arg Phe Ser Thr Met Pro Phe Met Phe Xaa
1               5                   10
```

<210> SEQ ID NO 25
<211> LENGTH: 8
<212> TYPE: PRT
<213> ORGANISM: Homo sapiens

<400> SEQUENCE: 25

```
Leu Arg Arg Phe Ser Thr Met Pro
1               5
```

<210> SEQ ID NO 26
<211> LENGTH: 9
<212> TYPE: PRT
<213> ORGANISM: Homo sapiens

<400> SEQUENCE: 26

```
Leu Asn Arg Phe Ser Thr Met Pro Phe
1               5
```

<210> SEQ ID NO 27
<211> LENGTH: 11
<212> TYPE: PRT
<213> ORGANISM: Artificial Sequence
<220> FEATURE:
<223> OTHER INFORMATION: Artificial sequence based on the human
      Collagen Type IV protein

```
<220> FEATURE:
<221> NAME/KEY: MISC_FEATURE
<222> LOCATION: (1)..(11)
<223> OTHER INFORMATION: X is norleucine (Nle)

<400> SEQUENCE: 27

Leu Arg Arg Phe Ser Thr Xaa Pro Phe Xaa Phe
1               5                   10

<210> SEQ ID NO 28
<211> LENGTH: 11
<212> TYPE: PRT
<213> ORGANISM: Homo sapiens

<400> SEQUENCE: 28

Leu Arg Arg Phe Ser Thr Met Pro Phe Met Phe
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(12)
<223> OTHER INFORMATION: X is 2-aminobutyric acid (Abu)

<400> SEQUENCE: 29

Phe Met Phe Xaa Asn Ile Asn Asn Val Xaa Asn Phe
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(16)
<223> OTHER INFORMATION: X is 2-aminobutyric acid

<400> SEQUENCE: 30

Ser Thr Met Pro Phe Met Phe Xaa Asn Ile Asn Asn Val Xaa Asn Phe
1               5                   10                  15

<210> SEQ ID NO 31
<211> LENGTH: 8
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(8)
<223> OTHER INFORMATION: X is 2-aminobutyric acid

<400> SEQUENCE: 31

Asn Ile Asn Asn Val Xaa Asn Phe
1               5

<210> SEQ ID NO 32
<211> LENGTH: 5
<212> TYPE: PRT
```

```
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(5)
<223> OTHER INFORMATION: X is 2-aminobutyric acid

<400> SEQUENCE: 32

Phe Xaa Asn Ile Asn
1               5

<210> SEQ ID NO 33
<211> LENGTH: 6
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(6)
<223> OTHER INFORMATION: X is 2-aminobutyric acid (Abu)

<400> SEQUENCE: 33

Phe Xaa Asn Ile Asn Val
1               5

<210> SEQ ID NO 34
<211> LENGTH: 9
<212> TYPE: PRT
<213> ORGANISM: Artificial Sequence
<220> FEATURE:
<223> OTHER INFORMATION: Artificial sequence based on the human
      Collagen Type IV protein

<400> SEQUENCE: 34

Phe Thr Asn Ile Asn Asn Val Thr Asn
1               5

<210> SEQ ID NO 35
<211> LENGTH: 9
<212> TYPE: PRT
<213> ORGANISM: Artificial Sequence
<220> FEATURE:
<223> OTHER INFORMATION: Artificial sequence based on the human
      Collagen Type IV protein
<220> FEATURE:
<221> NAME/KEY: MISC_FEATURE
<222> LOCATION: (1)..(9)
<223> OTHER INFORMATION: X is 2-aminobutyric acid (Abu)

<400> SEQUENCE: 35

Phe Xaa Asn Ile Asn Asn Val Xaa Asn
1               5

<210> SEQ ID NO 36
<211> LENGTH: 5
<212> TYPE: PRT
<213> ORGANISM: Artificial Sequence
<220> FEATURE:
<223> OTHER INFORMATION: NINNV fragment based on the human Collagen
      Type IV protein

<400> SEQUENCE: 36

Asn Ile Asn Asn Val
1               5
```